(12) United States Patent
Lee et al.

(10) Patent No.: US 9,666,812 B2
(45) Date of Patent: May 30, 2017

(54) NITROGEN-CONTAINING HETEROCYCLIC COMPOUND AND ORGANIC ELECTRONIC DEVICE USING SAME

(71) Applicant: LG CHEM, LTD., Seoul (KR)

(72) Inventors: Dong Hoon Lee, Daejeon (KR); Tae Yoon Park, Daejeon (KR); Sung Kil Hong, Daejeon (KR); Boonjae Jang, Daejeon (KR); Minseung Chun, Daejeon (KR); Dong Sik Kim, Daejeon (KR); Minyoung Kang, Uijeongbu-si (KR)

(73) Assignee: LG CHEM, LTD., Seoul (KR)

( * ) Notice: Subject to any disclaimer, the term of this patent is extended or adjusted under 35 U.S.C. 154(b) by 331 days.

(21) Appl. No.: 14/391,363

(22) PCT Filed: Apr. 12, 2013

(86) PCT No.: PCT/KR2013/003071
§ 371 (c)(1),
(2) Date: Oct. 8, 2014

(87) PCT Pub. No.: WO2013/154378
PCT Pub. Date: Oct. 17, 2013

(65) Prior Publication Data
US 2015/0123089 A1 May 7, 2015

(30) Foreign Application Priority Data
Apr. 13, 2012 (KR) ........................ 10-2012-0038395

(51) Int. Cl.
*H01L 51/50* (2006.01)
*H01L 51/00* (2006.01)
(Continued)

(52) U.S. Cl.
CPC ........ *H01L 51/0072* (2013.01); *C07D 235/02* (2013.01); *C07D 235/20* (2013.01);
(Continued)

(58) Field of Classification Search
CPC ............... H01L 51/5012; H01L 51/006; H01L 51/0068; H01L 51/0072; H01L 51/5088;
(Continued)

(56) References Cited

U.S. PATENT DOCUMENTS

2003/0165715 A1  9/2003  Yoon et al.
2007/0069203 A1  3/2007  Lee et al.
(Continued)

FOREIGN PATENT DOCUMENTS

CN  101870681 A  10/2010
CN  102276514 A  12/2011
(Continued)

OTHER PUBLICATIONS

P.R. Srinivasan, et al.: "Preparation and Properties of Polybenzimidazoles Containing Cardo Groups", Journal of Polymer Sciences, Polymer Chemistry Ed., 1982, vol. 20, pp. 3095-3105.
(Continued)

*Primary Examiner* — Gregory Clark
(74) *Attorney, Agent, or Firm* — Dentons US LLP

(57) ABSTRACT

The present application provides a new nitrogen-containing heterocyclic compound and an organic electronic device using the same.

20 Claims, 2 Drawing Sheets

(51) Int. Cl.
*C09K 11/06* (2006.01)
*C07D 401/14* (2006.01)
*C07D 405/14* (2006.01)
*C07D 235/20* (2006.01)
*C07D 409/14* (2006.01)
*C07D 235/02* (2006.01)
*C09B 57/00* (2006.01)

(52) U.S. Cl.
CPC ......... *C07D 401/14* (2013.01); *C07D 405/14* (2013.01); *C07D 409/14* (2013.01); *C09B 57/00* (2013.01); *C09K 11/06* (2013.01); *H01L 51/0052* (2013.01); *H01L 51/0058* (2013.01); *H01L 51/0067* (2013.01); *H01L 51/0068* (2013.01); *H01L 51/0073* (2013.01); *H01L 51/0074* (2013.01); *C09K 2211/1011* (2013.01); *C09K 2211/1029* (2013.01); *C09K 2211/1044* (2013.01); *H01L 51/006* (2013.01); *H01L 51/0077* (2013.01); *H01L 51/5012* (2013.01); *H01L 51/5056* (2013.01); *H01L 51/5072* (2013.01); *H01L 51/5088* (2013.01); *H01L 51/5092* (2013.01); *Y02E 10/549* (2013.01)

(58) Field of Classification Search
CPC .............. H01L 51/5056; H01L 51/0074; H01L 51/5092; H01L 51/0067; H01L 51/0058; H01L 51/0052; H01L 51/0073
See application file for complete search history.

(56) References Cited

U.S. PATENT DOCUMENTS

| 2007/0108892 | A1 | 5/2007 | Bae et al. |
| 2008/0233387 | A1 | 9/2008 | Kambe et al. |
| 2010/0001262 | A1 | 1/2010 | Kim et al. |
| 2010/0071769 | A1 | 3/2010 | Bae et al. |
| 2010/0253208 | A1 | 10/2010 | Cheng et al. |

FOREIGN PATENT DOCUMENTS

| EP | 2161319 A2 | 3/2010 | |
| JP | 1995-310071 A | 11/1995 | |
| JP | 07310071 | * 11/1995 | ............. C09K 11/06 |
| JP | 2000-095766 A | 4/2000 | |
| JP | 2001-097961 A | 4/2001 | |
| JP | 2002-151268 A | 5/2002 | |
| JP | 2002-513404 A | 5/2002 | |
| JP | 2004-352655 A | 12/2004 | |
| JP | 2004352655 A | 12/2004 | |
| JP | 2005-515233 A | 5/2005 | |
| JP | 2005-232159 A | 9/2005 | |
| JP | 2008-521243 A | 6/2008 | |
| JP | 2008-252084 A | 10/2008 | |
| JP | 2009-514812 A | 4/2009 | |
| JP | 2009-545156 A | 12/2009 | |
| JP | 2010-511696 A | 4/2010 | |
| KR | 10-2010-0121267 A | 11/2010 | |
| KR | 10-2011-0047803 A | 5/2011 | |
| WO | 98/38170 A1 | 9/1998 | |
| WO | 2010/121267 A1 | 10/2010 | |
| WO | 2010/128745 A1 | 11/2010 | |
| WO | WO 2011/136484 | * 11/2011 | ........... C07D 211/61 |

OTHER PUBLICATIONS

"Using a double-doping strategy to prepare a bilayer device architecture for high-efficiency red PhOLEDs", Kao, et al. Journal of Materials Chemistry, vol. 21, No. 6, pp. 1846-1851.
Joel M. Kauffman et al. "Synthesis and Photophysical Properties of Fluorescent 2-Aryl-1,3-dialkylbenzimidazolium Ions and a 1-Alkyl-2-arylbenzimidazole with Excited State Intramolecular Proton-Transfer" Journal of Heterocyclic Chemistry, vol. 31, Issue 4, pp. 957-965 Jul./Aug. 1994.
"Naphthylendi (hteroarene), III. Synthese undspektroskopisches Verhalten von 2,2;-Naphthylendibenzazolen", Leibigs Annalen der Chemie, vol. 1984, issue 6, pp. 1129-1136, Jun. 12, 1984.
Chia-Ming Yang et al. "Electron Mobility and Electroluminescence Efficiency of Blue Conjugated Polymers" Synthetic Metals, Jan. 14, 2008, pp. 25-28.
Korean Office Action issued Aug. 27, 2014 in corresponding Korean Application No. 10-2013-0040288.
Taiwan Office Action issued May 13, 2014 in corresponding Taiwanese Application No. 102113024.

* cited by examiner

NITROGEN-CONTAINING HETEROCYCLIC COMPOUND AND ORGANIC ELECTRONIC DEVICE USING SAME

This application is a National Stage Application of International Patent Application No. PCT/KR2013/003071, filed on Apr. 12, 2013, which claims the benefit of Korean Patent Application No. 10-2012-0038395, filed on Apr. 13, 2012, in the Korean Intellectual Property Office, all of which are incorporated herein by reference in their entirety.

TECHNICAL FIELD

The present invention relates to a new nitrogen-containing heterocyclic compound and an organic electronic device using the same.

BACKGROUND ART

An organic electronic device means a device that requires exchanging of electric charges between electrodes using holes and/or electrons and organic materials. The organic electronic device may be largely divided into the following two categories according to an operation principle. First, there is an electronic device in which an exiton is formed in an organic material layer by a photon that flows from an external light source to the device, the exiton is separated into electrons and holes, and the electrons and the holes are respectively transferred to different electrodes and used as a current source (voltage source). Second, there is an electronic device in which holes and/or electrons are injected into an organic material semiconductor forming an interface with the electrode by applying a voltage or a current to two or more electrodes, and the device is operated by the injected electrons and holes.

Examples of the organic electronic device include an organic light emitting device, an organic solar cell, an organic photoconductor (OPC), an organic transistor and the like, and all of the devices require a hole injection or transporting material, an electron injection or transporting material, or a light emitting material in order to drive the device. Hereinafter, an organic light emitting device will be mainly described in detail, but in the organic electronic devices, the hole injection or transporting material, the electron injection or transporting material or the light emitting material are operated on the basis of a similar principle.

In general, an organic light emitting phenomenon refers to a phenomenon that converts electric energy into light energy by using an organic material. The organic light emitting device using the organic light emitting phenomenon has a structure which typically includes an anode, a cathode, and an organic material layer that is disposed therebetween. Herein, the organic material layer frequently has a multi-layered structure that includes different materials in order to enhance efficiency and stability of the organic light emitting device, and may include, for example, a hole injection layer, a hole transporting layer, a light emitting layer, an electron transporting layer, an electron injection layer and the like. In the structure of the organic light emitting device, if a voltage is applied between two electrodes, holes are injected from an anode and electrons are injected from a cathode into the organic material layer, and when the injected holes and electrons meet each other, an exciton is formed, and light is emitted when the exciton falls to a bottom state. It is known that this organic light emitting device has properties such as self-light emission, high brightness, high efficiency, low driving voltage, a wide viewing angle, high contrast, a high speed responsiveness and the like.

In the organic light emitting device, the material that is used as the organic material layer may be classified into a light emitting material and an electric charge transporting material, for example, a hole injection material, a hole transporting material, an electron transporting material, an electron injection material, and the like, according to a function thereof. Further, the light emitting material may be classified into blue, green, and red light emitting materials and yellow and orange light emitting materials required for implementing better natural colors, according to the emission color. Meanwhile, when only one material is used as a light emitting material, due to interaction between molecules, there are problems in that the maximum light emitting wavelength moves to the long wavelength, the color purity is lowered, or efficiency of the device is lowered due to a reduced effect of light emission, and thus in order to increase light emission efficiency through increasing color purity and energy transfer, a host/dopant system may be used as the light emitting material.

In order to allow the organic light emitting device to sufficiently show the above-described excellent properties, a material constituting the organic material layer in the device, for example, a hole injection material, a hole transporting material, a light emitting material, an electron transporting material, an electron injection material and the like need to be supported by stable and efficient materials above anything else, but the development of a stable and efficient organic material layer material for organic light emitting device has not been sufficiently achieved. Therefore, there is a continuous need for developing a new material, and the necessity for developing the aforementioned material is similarly applied to the above-described other organic electronic devices.

DETAILED DESCRIPTION OF THE INVENTION

Technical Problem

The present inventors have found out a nitrogen-containing heterocyclic compound having a new structure. In addition, the present inventors have found out that when an organic material layer of an organic electronic device is formed by using the new nitrogen-containing heterocyclic compound, effects such as an increase in efficiency of the device, a drop in driving voltage, an increase in stability and the like may be shown.

Thus, the present application has been made in an effort to provide a nitrogen-containing heterocyclic compound and an organic electronic device using the same.

Technical Solution

The present application provides a new nitrogen-containing heterocyclic compound.

Further, the present application provides an organic electronic device including a first electrode, a second electrode, and an organic material layer having one or more layers disposed between the first electrode and the second electrode, in which one or more layers of the organic material layer include a new nitrogen-containing heterocyclic compound.

Advantageous Effects

The new nitrogen-containing heterocyclic compound according to the present application may be used as a material of an organic material layer of an organic electronic device including an organic light emitting device, and the organic electronic device including the organic light emitting device using the same shows excellent properties in terms of efficiency, driving voltage, service life, and the like. In particular, the new nitrogen-containing heterocyclic compound according to the present application has excellent thermal stability, a deep HOMO level, a high triplet state, and hole stability, and thus shows excellent properties. The new nitrogen-containing heterocyclic compound may be used either alone or in a mixture of impurities in organic electronic devices including an organic light emitting device, and may improve light efficiency, and life properties of the device due to thermal stability of the compound.

DESCRIPTION OF SYMBOLS OF MAIN PARTS OF DRAWINGS

Figure 1:
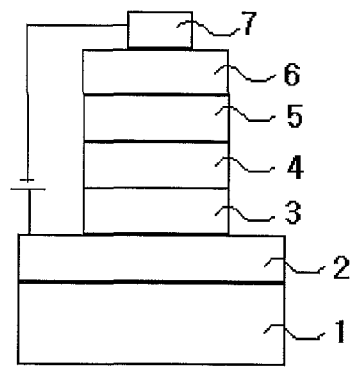
FIGS. 1 to 5 are cross-sectional views exemplifying a structure of an organic electronic device according to the present application.

1 Substrate
2 Anode
3 Hole injection layer
4 Hole transporting layer
5 Light emitting layer
6 Electron transporting layer
7 Cathode

BEST MODE

An exemplary embodiment of the present application provides a nitrogen-containing heterocyclic compound represented by the following Formula 1.

[Formula 1]

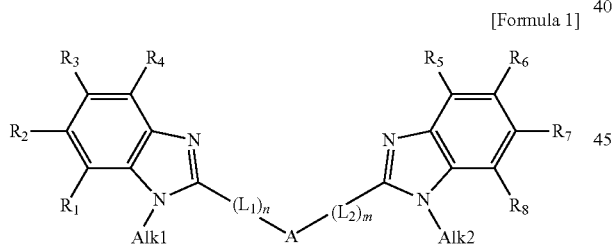

In Formula 1,
$R_1$ to $R_8$ are the same as or different from each other, and are each independently hydrogen; deuterium; a halogen group; a nitrile group; a nitro group; a hydroxy group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted alkylamine group; a substituted or unsubstituted aralkylamine group; a substituted or unsubstituted arylamine group; a substituted or unsubstituted heteroarylamine group; a substituted or unsubstituted aryl group; a substituted or unsubstituted fluorenyl group; a substituted or unsubstituted carbazole group; or a substituted or unsubstituted heterocyclic group including one or more of N, O, and S atoms, or two or more adjacent groups of $R_1$ to $R_8$ form a monocyclic or polycyclic ring, Alk1 and Alk2 are the same as or different from each other, and are each independently a substituted or unsubstituted alkyl group; or a substituted or unsubstituted cycloalkyl group;

$L_1$ and $L_2$ are the same as or different from each other, and are each independently a direct bond; oxygen; sulfur; substituted or unsubstituted nitrogen; substituted or unsubstituted phosphorus; a substituted or unsubstituted arylene group; a substituted or unsubstituted alkenylene group; a substituted or unsubstituted fluorenylene group; a substituted or unsubstituted carbazolylene group; or a substituted or unsubstituted heteroarylene group including one or more of N, O, and S atoms, and n is an integer from 1 to 3, m is an integer from 1 to 3, and when n and m are each present as two or more, the substituents in the parenthesis are each independently the same as or different from each other, A is selected from the following structures,

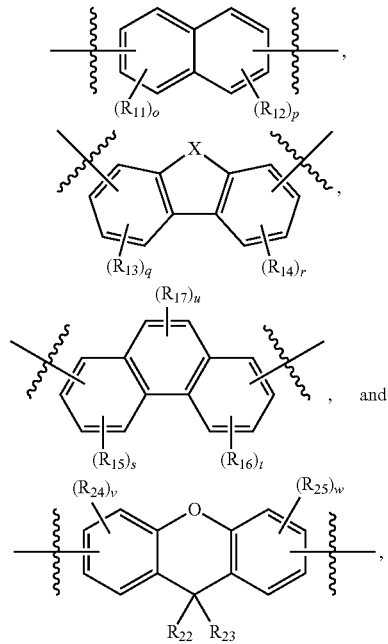

o, p, q, r, s, t, v, and w are each an integer from 0 to 3, and u is an integer from 0 to 2, X is —O—, —S—, or —C($R_{20}$)($R_{21}$)—, $R_{11}$ to $R_{17}$, $R_{20}$, $R_{21}$, $R_{24}$, and $R_{25}$ are the same as or different from each other, and are each independently hydrogen; deuterium; a halogen group; a nitrile group; a nitro group; a hydroxy group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted alkylamine group; a substituted or unsubstituted aralkylamine group; a substituted or unsubstituted arylamine group; a substituted or unsubstituted heteroarylamine group; a substituted or unsubstituted aryl group; a substituted or unsubstituted fluorenyl group; a substituted or unsubstituted carbazole group; or a substituted or unsubstituted heterocyclic group including one or more of N, O, and S atoms, and $R_{22}$ and $R_{23}$ are the same as or different from each other, and are each independently hydrogen; or a substituted or unsubstituted alkyl group.

Another exemplary embodiment of the present application provides a nitrogen-containing heterocyclic compound represented by the following Formula 2.

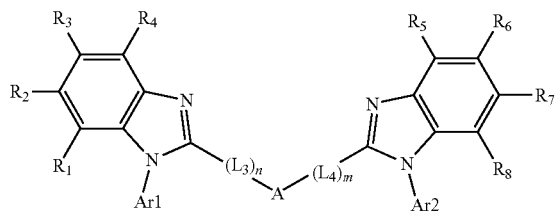

[Formula 2]

In Formula 2, $R_1$ to $R_8$, A, n, and m are the same as those defined in Formula 1, Ar1 and Ar2 are the same as or different from each other, and are each independently a substituted or unsubstituted aryl group; or a substituted or unsubstituted heterocyclic group;

$L_3$ and $L_4$ are the same as or different from each other, and are each independently oxygen; sulfur; substituted or unsubstituted nitrogen; substituted or unsubstituted phosphorus; a substituted or unsubstituted arylene group; a substituted or unsubstituted alkenylene group; a substituted or unsubstituted fluorenylene group; a substituted or unsubstituted carbazolylene group; or a substituted or unsubstituted heteroarylene group including one or more of N, O, and S atoms.

In Formula 2, when $L_3$ and $L_4$ are a direct bond, Tg is low, and thus there is a problem in that device properties deteriorate. The problem may be solved by introducing $L_3$ and $L_4$ to increase Tg, rather than a direct bond. In particular, when A is phenanthrene, a better effect may be obtained by improving Tg.

In Formulas 1 and 2, specific examples of A may be represented as follows.

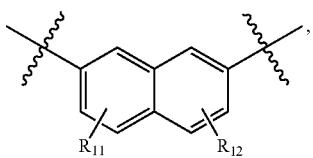

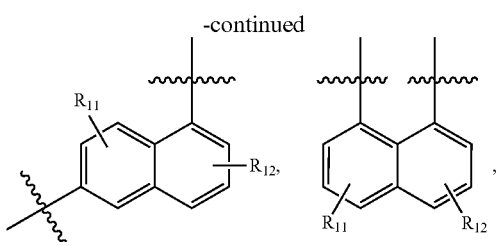

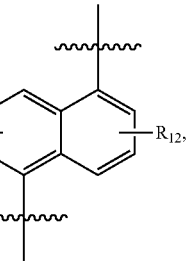 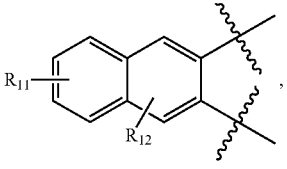

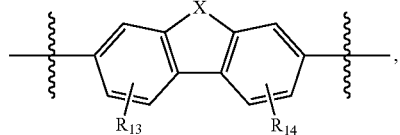

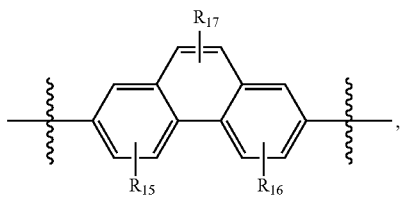

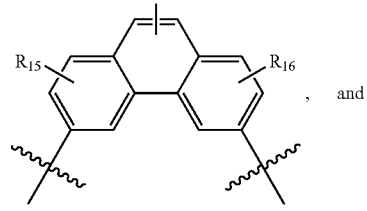

, and

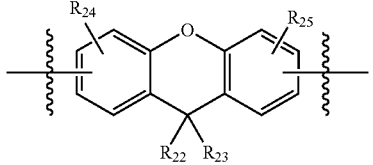

$R_{11}$ to $R_{17}$ and $R_{22}$ to $R_{25}$ are the same as those defined in Formula 1.

According to an exemplary embodiment of the present application, the new nitrogen-containing heterocyclic compound represented by Formula 1 may be represented by any one of the following Formulas 1-1 to 1-5.

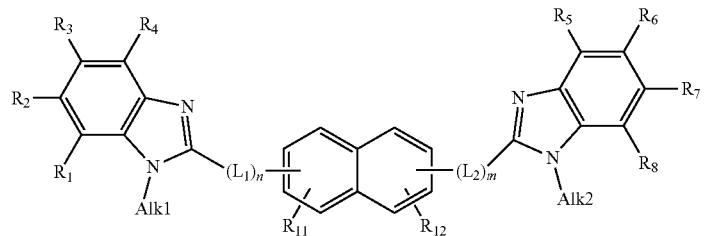
[Formula 1-1]
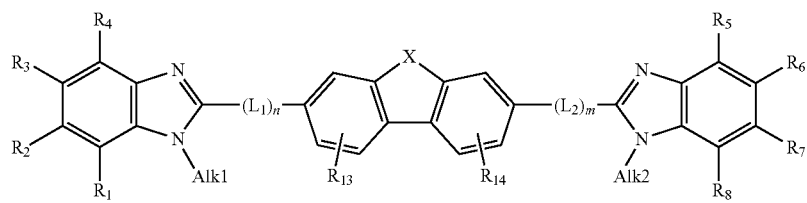
[Formula 1-2]
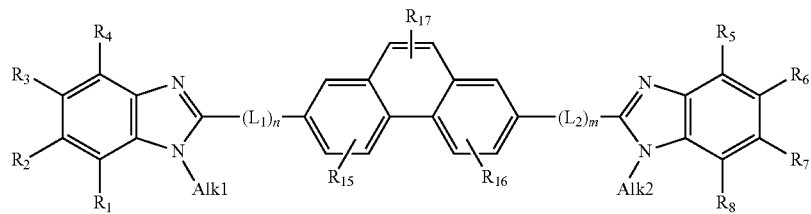
[Formula 1-3]
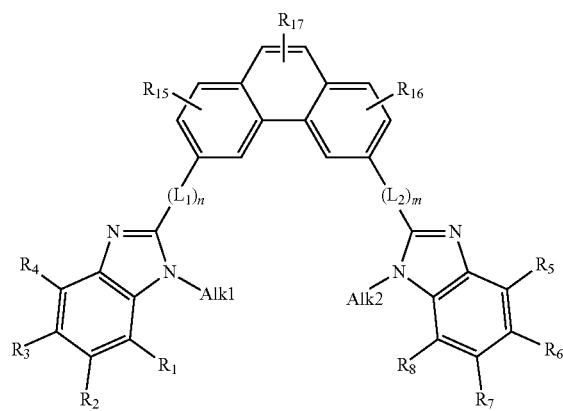
[Formula 1-4]
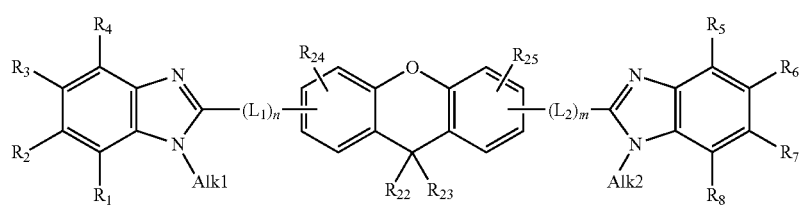
[Formula 1-5]

In Formulas 1-1 to 1-5, $R_1$ to $R_8$, $R_{11}$ to $R_{17}$, $R_{22}$ to $R_{25}$, $L_1$, $L_2$, Alk1, Alk2, n, m, and X are the same as those defined above.

According to an exemplary embodiment of the present application, the new nitrogen-containing heterocyclic compound represented by Formula 2 may be represented by any one of the following Formulas 2-1 to 2-5.

In the present application, it is preferred that the alkyl group has a carbon number of 1 to 30 and does not cause a steric hindrance. Specific examples thereof include a methyl group, an ethyl group, a propyl group, an isopropyl group, a butyl group, a t-butyl group, a pentyl group, a hexyl group, a heptyl group and the like, but are not limited thereto.

[Formula 2-1]

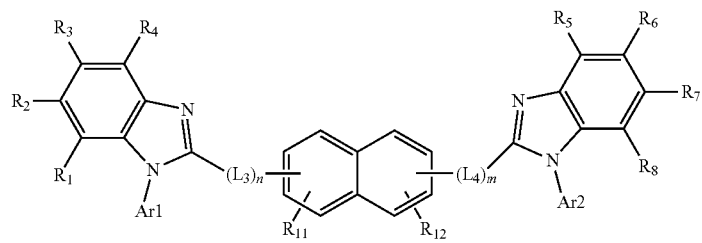

[Formula 2-2]

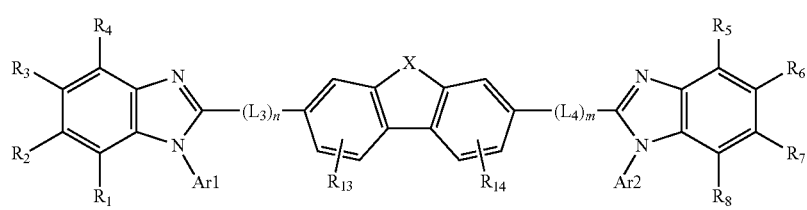

[Formula 2-3]

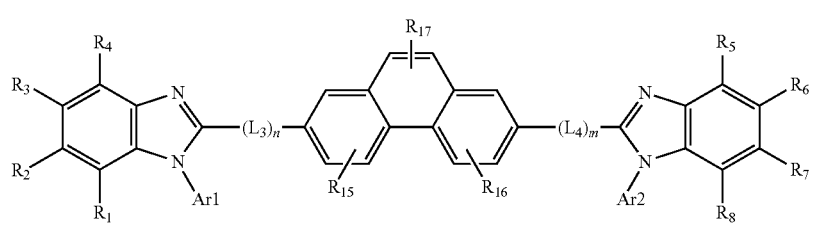

[Formula 2-4]

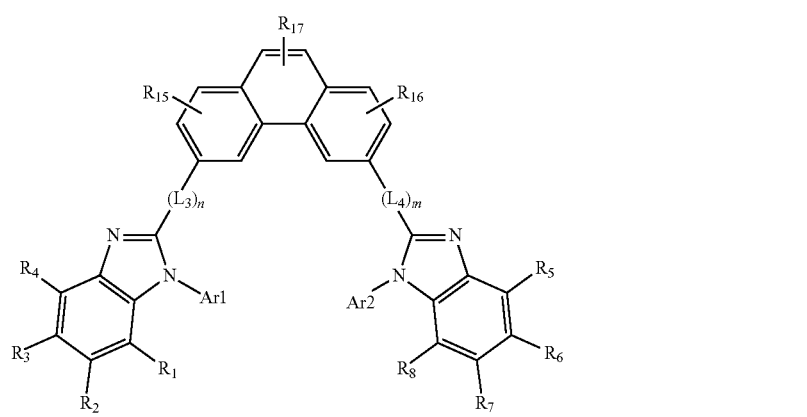

[Formula 2-5]

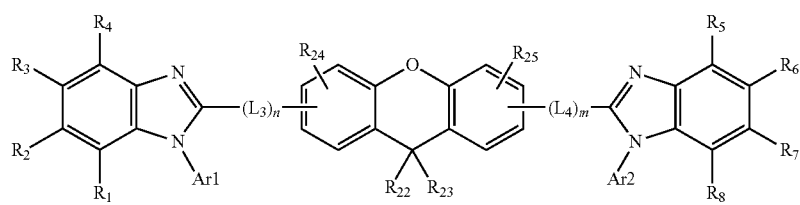

In Formulas 2-1 to 2-5, $R_1$ to $R_8$, $R_{11}$ to $R_{17}$, $R_{22}$ to $R_{25}$, $L_3$, $L_4$, Ar1, Ar2, n, m, and X are the same as those defined above.

Examples of the substituents will be described below, but are not limited thereto.

In the present application, the alkoxy group may be a straight chain or branched chain. The carbon number of the alkoxy group is not particularly limited, but is preferably from 1 to 30, which is a range that does not cause a steric hindrance. The number of carbon atoms of the alkoxy group does not affect the conjugate length of the compound, but only affects the method of applying the compound to the organic electronic device, for example, a vacuum deposition method or a solution coating method. Therefore, the carbon number of the alkoxy group is not particularly limited.

In the present application, the alkenyl group may be a straight chain or branched chain, and is preferably an alkenyl group having from 2 to 40 carbon atoms, and specifically, the alkenyl group is preferably an alkenyl group in which an aryl group, such as a stylbenyl group, a styrenyl group and the like, is substituted, but is not limited thereto.

In the present specification, the aryl group may be monocyclic or polycyclic, and the number of carbon atoms thereof is not particularly limited, but is preferably 6 to 60. Examples of a monocyclic aryl group include a phenyl group, a biphenyl group, a terphenyl group, a stilbene group, and the like, and examples of a polycyclic aryl group include a naphthyl group, an anthracenyl group, a phenanthrenyl group, a pyrenyl group, a perylenyl group, a tetracenyl group, a chrysenyl group, a fluorenyl group, an acenaphthacenyl group, a triphenylene group, a fluoranthrene group, and the like, but the scope of the present application is not limited to these examples.

In the present application, the heterocyclic group is a heterocyclic group including at least one of O, N, and S as a heteroatom, and the carbon number thereof is not particularly limited, but is preferably from 2 to 60. Examples of the heterocyclic group include a thiophene group, a furan group, a pyrrole group, an imidazole group, a triazole group, an oxazole group, an oxadiazole group, a triazole group, a pyridyl group, a bipyridyl group, a triazine group, an acrydyl group, a pyridazine group, a quinolinyl group, an isoquinoline group, an indole group, a carbazole group, a benzoxazole group, a benzimidazole group, a benzothiazolyl group, a benzocarbazolyl group, a benzthiophene group, a dibenzothiophene group, a benzfuranyl group, a dibenzofuranyl group and the like, but are not limited thereto.

In the present specification, the cycloalkyl group may be monocyclic or polycyclic, and the number of carbon atoms is not particularly limited, but is preferably from 3 to 60. Examples of the cycloalkyl group include a cyclopentyl group and a cyclohexyl group.

In the present specification, examples of a halogen group include fluorine, chlorine, bromine, or iodine.

In the present application, the fluorenyl group is a structure in which two cyclic organic compounds are linked to each other through one atom, and examples thereof include

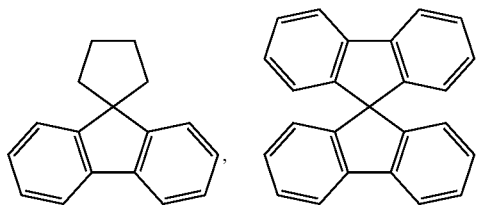

and the like.

In the present application, the fluorenyl group includes a structure of an open fluorenyl group, and the open fluorenyl group herein is a structure in which the link of one cyclic compound is broken in a structure in which two cyclic organic compounds are linked to each other through one atom, and examples thereof include

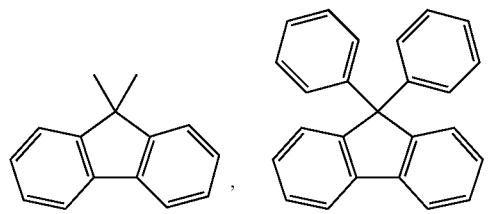

and the like.

In the present application, examples of the arylamine group include a substituted or unsubstituted monocyclic diarylamine group, a substituted or unsubstituted polycyclic diarylamine group, or a substituted or unsubstituted monocyclic and polycyclic diarylamine group.

In the present application, the aryl group in the aryloxy group, the arylthioxy group, the arylsulfoxy group, and the aralkylamine group is the same as the above-described examples of the aryl group.

In the present application, the alkyl group in the alkylthioxy group, the alkylsulfoxy group, the alkylamine group, and the aralkylamine group is the same as the above-described examples of the alkyl group.

In the present application, the heteroaryl group in the heteroarylamine group may be selected from the above-described examples of the heterocyclic group.

In the present application, the aralkyl group in the aralkylamine group is an alkyl group substituted with an aryl group, the aryl group is the same as the above-described examples, and the alkyl group is the same as the above-described examples.

In the present application, the term "substituted or unsubstituted" means being substituted or unsubstituted with at least one substituent of deuterium; a halogen group; a nitrile group; a nitro group; a hydroxy group; an alkyl group; a cycloalkyl group; an alkoxy group; an aryloxy group; an alkylthioxy group; an arylthioxy group; an alkylsulfoxy group; an arylsulfoxy group; an alkenyl group; a silyl group; a boron group; an alkylamine group; an aralkylamine group; an arylamine group; an aryl group; a fluorenyl group; a carbazole group; and a heterocyclic group including one or more of N, O, and S atoms. Herein, the term "unsubstituted" means having no substituent other than hydrogen.

In the present application, an arylene group, an alkenylene group, a fluorenylene group, a carbazolylene group, and a heteroarylene group are a divalent group of an aryl group, an alkenyl group, a fluorenyl group, and a carbazole group, respectively. Except that these groups are each a divalent group, the above-described description of an aryl group, an alkenyl group, a fluorenyl group, and a carbazole group may be applied to these groups.

In the present application, oxygen means a divalent oxygen atom.

In the present application, sulfur means a divalent sulfur atom.

In the present application, the substituted or unsubstituted nitrogen means that in a secondary amine group, the other substituent is hydrogen, or selected from deuterium; a halogen group; a nitrile group; a nitro group; a hydroxy group; an alkyl group; a cycloalkyl group; an alkoxy group; an aryloxy group; an alkylthioxy group; an arylthioxy group; an alkylsulfoxy group; an arylsulfoxy group; an alkenyl group; a silyl group; a boron group; an alkylamine group; an aralkylamine group; an arylamine group; an aryl group; a fluorenyl group; a carbazole group; and a heterocyclic group including one or more of N, O, and S atoms.

In the present application, the substituted or unsubstituted phosphorus means that in a divalent phosphorus atom, the other substituent is hydrogen, or selected from deuterium; a halogen group; a nitrile group; a nitro group; a hydroxy group; an alkyl group; a cycloalkyl group; an alkoxy group; an aryloxy group; an alkylthioxy group; an arylthioxy group; an alkylsulfoxy group; an arylsulfoxy group; an alkenyl group; a silyl group; a boron group; an alkylamine group; an aralkylamine group; an arylamine group; an aryl group; a fluorenyl group; a carbazole group; and a heterocyclic group including one or more of N, O, and S atoms.

In the present application, the substituted arylene group means that a phenyl group, a biphenyl group, a naphthalene group, a fluorenyl group, a pyrenyl group, a phenanthrenyl group, a perylene group, a tetracenyl group, an anthracenyl group, and the like are substituted with another substituent.

In the present application, the substituted heteroarylene group means that a pyridyl group, a thiophenyl group, a triazine group, a quinoline group, a phenanthroline group, an imidazole group, a thiazole group, an oxazole group, a carbazole group, and a condensed heterocyclic group thereof, for example, a benzoquinoline group, a benzimidazole group, a benzoxazol group, a benzothiazolyl group, a benzocarbazolyl group, a dibenzothiophenyl group, and the like are substituted with another substituent.

According to an exemplary embodiment of the present application, Alk1 and Alk2 may be the same substituted or unsubstituted alkyl group; and substituted or unsubstituted cycloalkyl group.

According to an exemplary embodiment of the present application, Ar1 and Ar2 may be the same substituted or unsubstituted aryl group; and substituted or unsubstituted heterocyclic group. The present application provides the new nitrogen-containing heterocyclic compound represented by Formula 1 or 2. Such a compound may be used as an organic material layer in an organic electronic device due to structural specificity thereof.

In an exemplary embodiment of the present application, Alk1 and Alk2 in Formula 1 are each a substituted or unsubstituted alkyl group, and may be methyl, ethyl, propyl, or isopropyl.

In another exemplary embodiment of the present application, Ar1 and Ar2 in Formula 2 may be a polycyclic aryl group having two or more rings, or a substituted aryl group. For example, Ar1 and Ar2 may be biphenyl, naphthyl, anthracenyl, and the like. In Formula 2, when a polycyclic aryl having more abundant electrons, for example, a group such as biphenyl, naphthyl, and the like is introduced as compared to the case where Ar1 or Ar2 is a monocyclic aryl, electron mobility is further increased. This contributes to the improvement in efficiency of the device, and thus a further excellent effect may be obtained.

In another exemplary embodiment of the present application, $L_1$ and $L_2$ in Formula 1 are each a direct bond, a substituted or unsubstituted arylene group, or a substituted or unsubstituted heteroarylene group, and may be specifically a phenylene group, a biphenylene group, or a pyridine group.

In another exemplary embodiment of the present application, $L_3$ and $L_4$ in Formula 2 are each a substituted or unsubstituted arylene group, or a substituted or unsubstituted heteroarylene group, and may be specifically a phenylene group, a biphenylene group, or a pyridine group.

In Formulas 1-2 and 2-2, X is —O—, —S—, or —C($R_{20}$)($R_{21}$)—. Herein, $R_{20}$ and $R_{21}$ are the same as those defined above. In an exemplary embodiment, $R_{20}$ and $R_{21}$ may be a substituted or unsubstituted alkyl group; or a substituted or unsubstituted aryl group, and may be specifically a methyl group; or an alkyl-substituted or unsubstituted phenyl group.

In another exemplary embodiment, $R_3$ and $R_6$ in Formula 1 or 2 are a substituted or unsubstituted aryl group, and specifically, a substituted or unsubstituted phenyl group, and $R_1$, $R_2$, $R_4$, $R_5$, $R_7$, and $R_8$ are hydrogen.

In another exemplary embodiment, $R_1$ to $R_8$ in Formula 1 or 2 are hydrogen.

In the exemplary embodiments, when at least two of $R_1$ to $R_8$ form a monocyclic or polycyclic ring, the monocyclic or polycyclic ring may be a substituted or unsubstituted aliphatic or aromatic ring. The aliphatic or aromatic ring may be monocyclic or polycyclic. The aliphatic ring may be a cycloalkane. The aromatic ring includes benzene, naphthalene, anthracene, phenanthrene, and the like.

In another exemplary embodiment, $R_1$ and $R_2$ in Formula 1 or 2 form a substituted or unsubstituted aromatic ring.

In another exemplary embodiment, $R_3$ and $R_4$ in Formula 1 or 2 form a substituted or unsubstituted aromatic ring.

In another exemplary embodiment, $R_5$ and $R_6$ in Formula 1 or 2 form a substituted or unsubstituted aromatic ring.

In another exemplary embodiment, $R_7$ and $R_8$ in Formula 1 or 2 form a substituted or unsubstituted aromatic ring.

In another exemplary embodiment, $R_1$ and $R_2$ in Formula 1 or 2 form a substituted or unsubstituted aromatic ring, and $R_7$ and $R_8$ form a substituted or unsubstituted aromatic ring.

In another exemplary embodiment, $R_3$ and $R_4$ in Formula 1 or 2 form a substituted or unsubstituted aromatic ring, and $R_5$ and $R_6$ form a substituted or unsubstituted aromatic ring.

In another exemplary embodiment, $R_1$ and $R_2$ in Formula 1 or 2 form a substituted or unsubstituted aromatic ring, $R_3$ and $R_4$ form a substituted or unsubstituted aromatic ring, $R_5$ and $R_6$ form a substituted or unsubstituted aromatic ring, and $R_7$ and $R_8$ form a substituted or unsubstituted aromatic ring.

In the present application, when A is

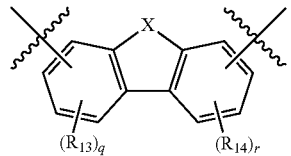

and X is —C($R_{20}$)($R_{21}$)—, $R_{20}$ and $R_{21}$ do not form a spiro structure with the structure. When $R_{20}$ and $R_{21}$ form a spiro structure, the electron mobility is decreased, and thus the device efficiency may be adversely affected (Chia-Ming Yang et al., Synthetic Metals, 158 (2008) 25-28). In the present application, $R_{20}$ and $R_{21}$ are each preferably an alkyl group, and may be, for example, a methyl group.

In the present application, when A is

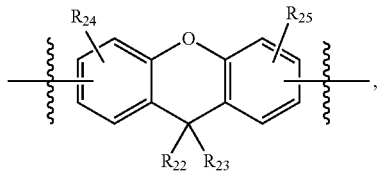

$R_{22}$ and $R_{23}$ are preferably an alkyl group, and may be, for example, a $C_{1-6}$ alkyl group, and more specifically, a methyl group.

Preferred specific examples of the compound according to the present application include the following compounds, but are not limited thereto.

[Formula 3-1]
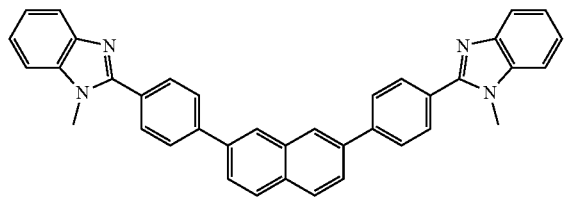
[Formula 3-2]
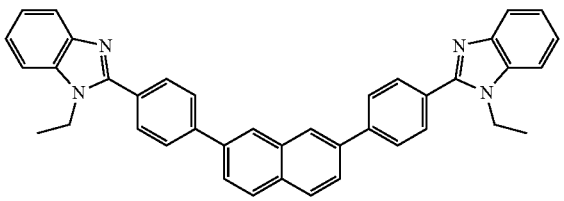
[Formula 3-3]
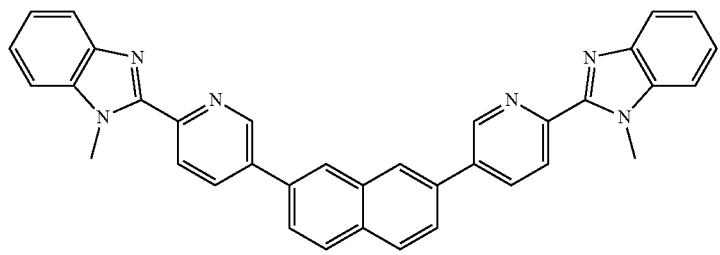
[Formula 3-4]
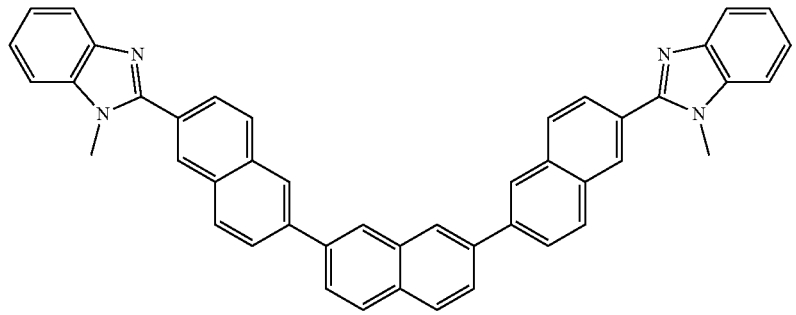
[Formula 3-5]
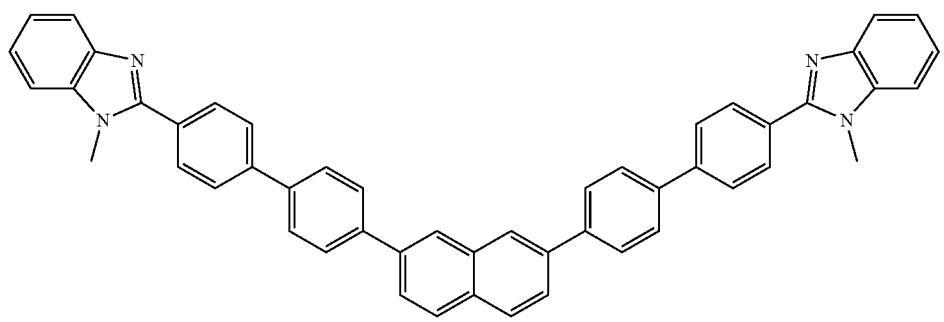
[Formula 3-6]
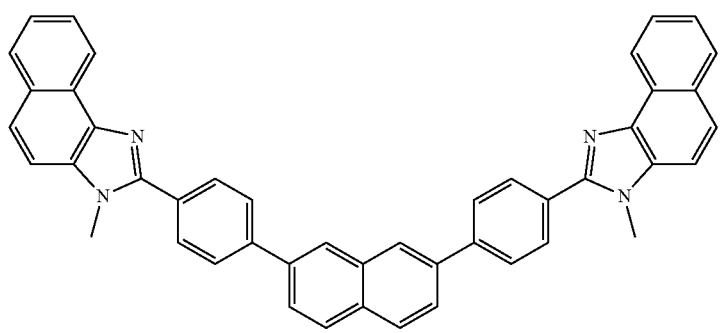

[Formula 3-7]
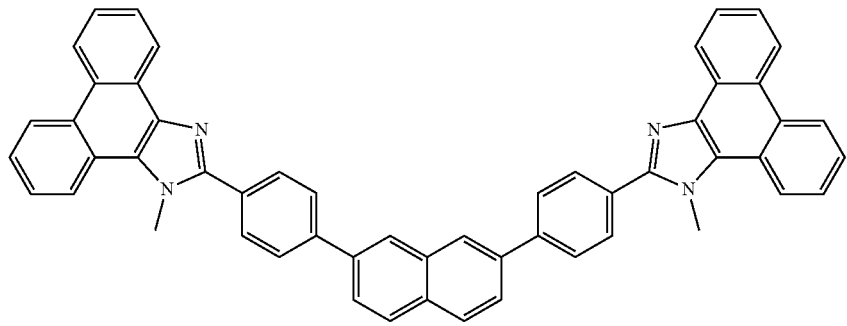
[Formula 3-8]
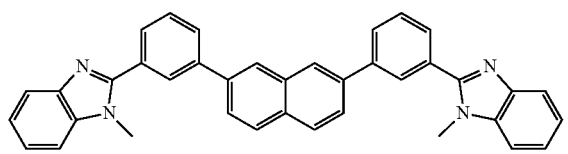
[Formula 3-9]
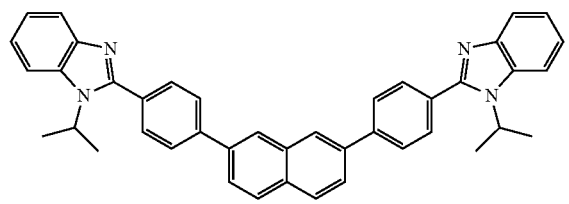
[Formula 3-10]
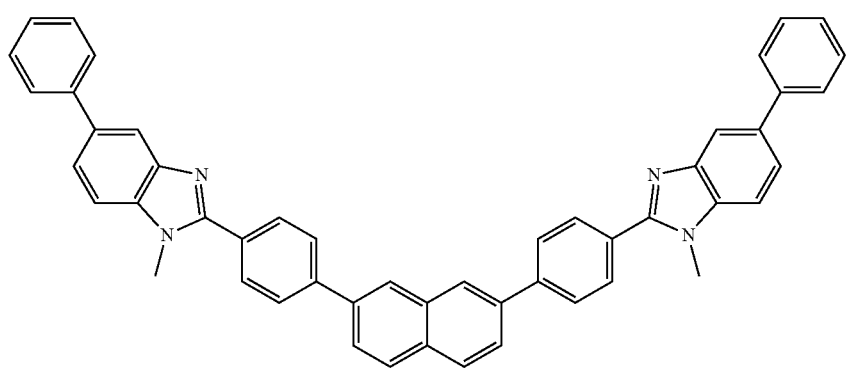
[Formula 3-11]
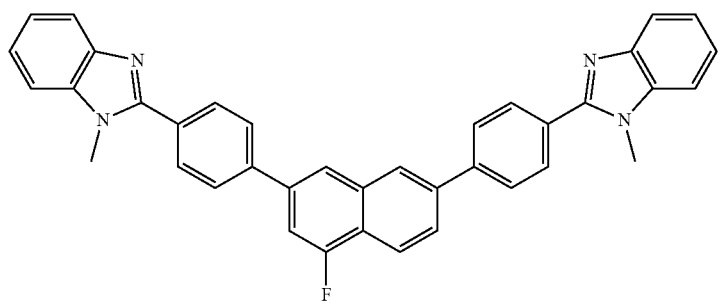
[Formula 3-12]
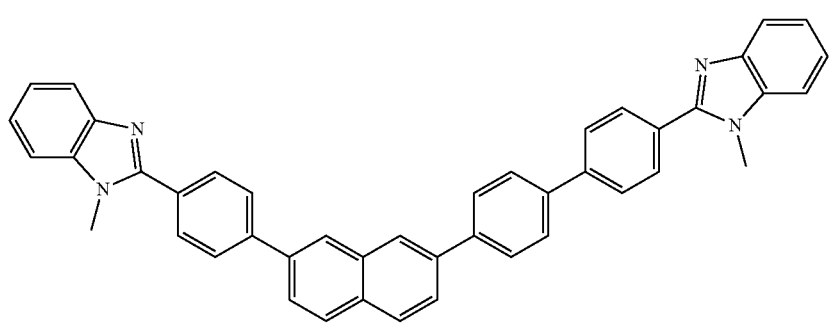

-continued
[Formula 3-13]
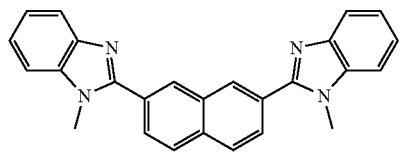
[Formula 3-14]
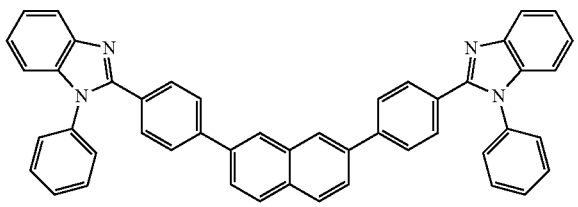
[Formula 3-15]
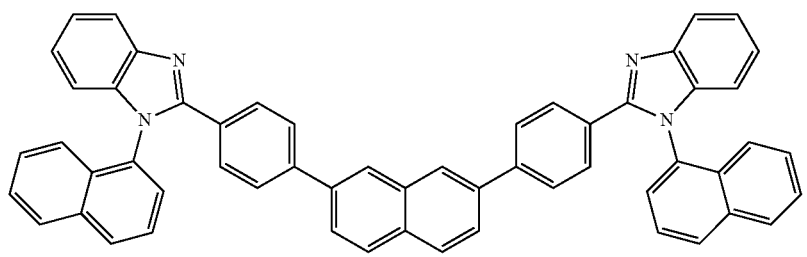
[Formula 4-1]
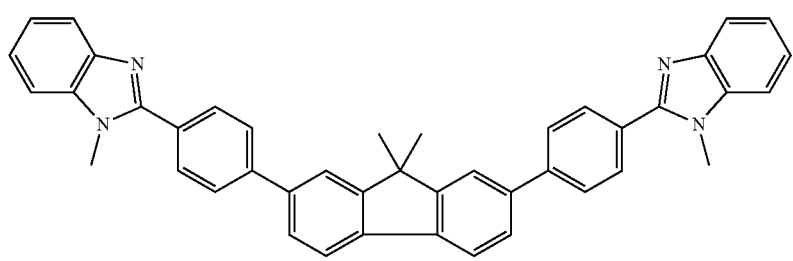
[Formula 4-2]
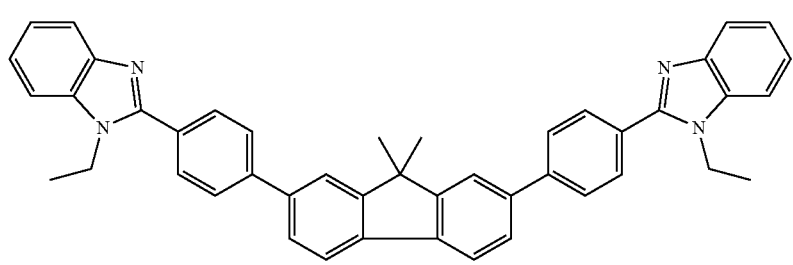
[Formula 4-3]
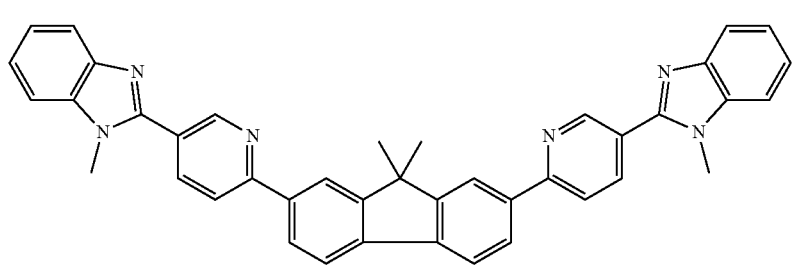
[Formula 4-4]
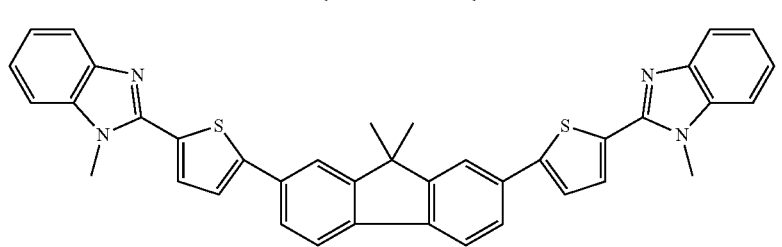

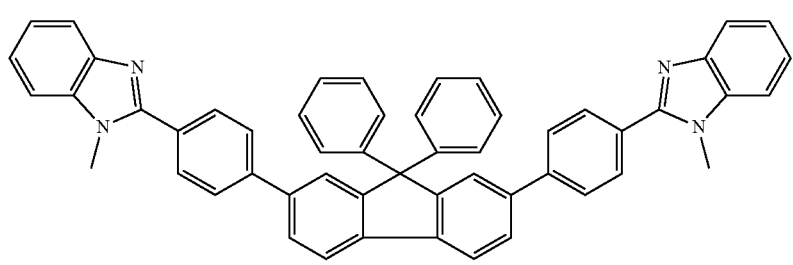
[Formula 4-5]
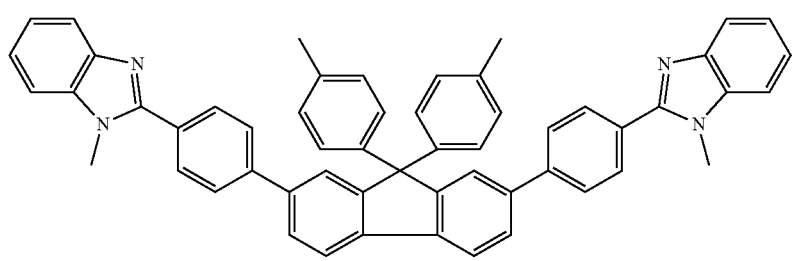
[Formula 4-6]
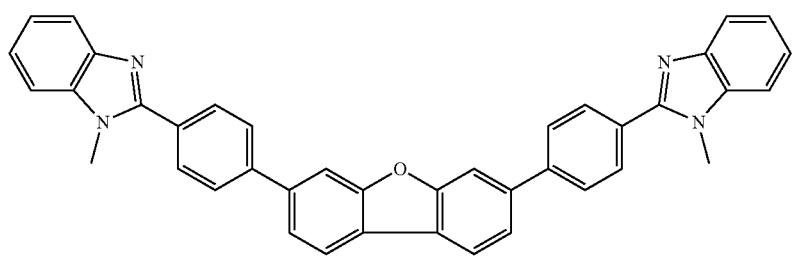
[Formula 4-7]
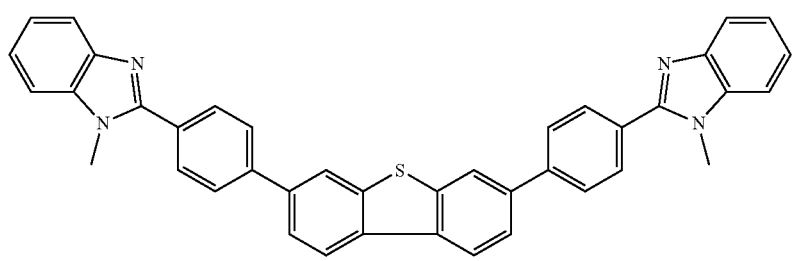
[Formula 4-8]
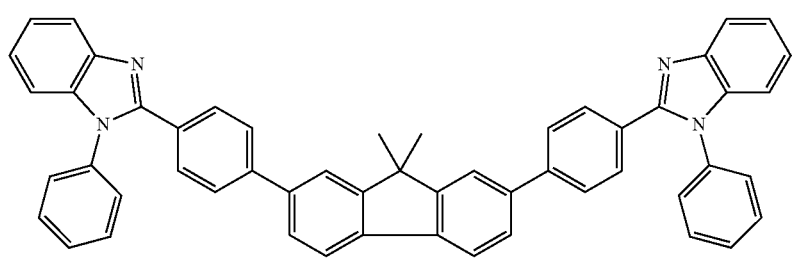
[Formula 4-9]

[Formula 4-10]
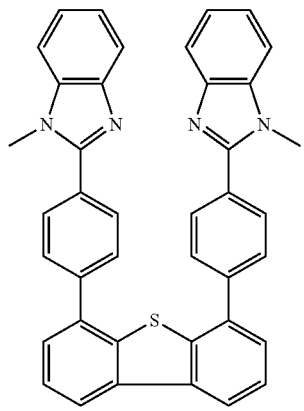
[Formula 4-11]
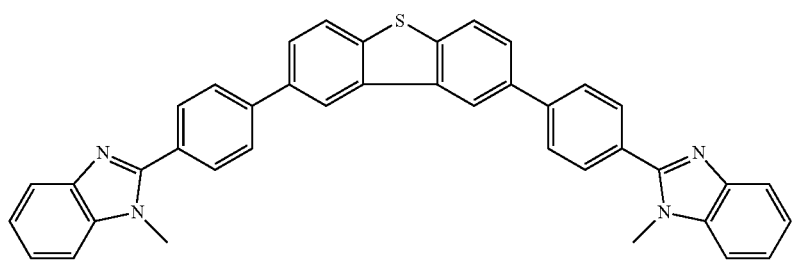
[Formula 4-12]
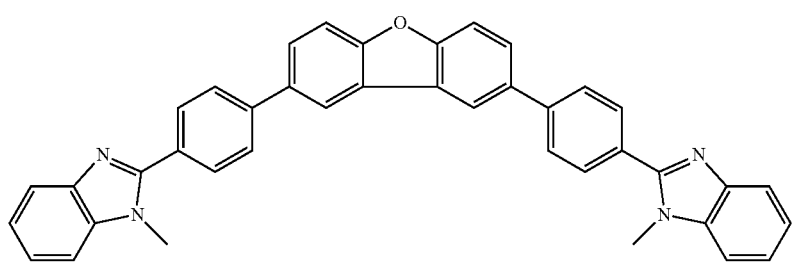
[Formula 4-13]
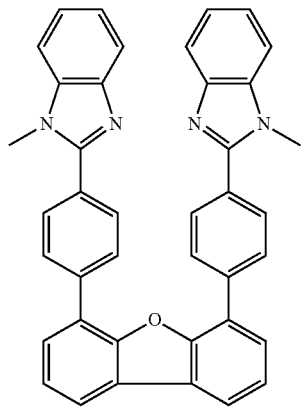
[Formula 5-1]
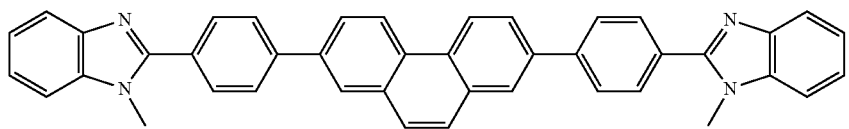

-continued
[Formula 5-2]
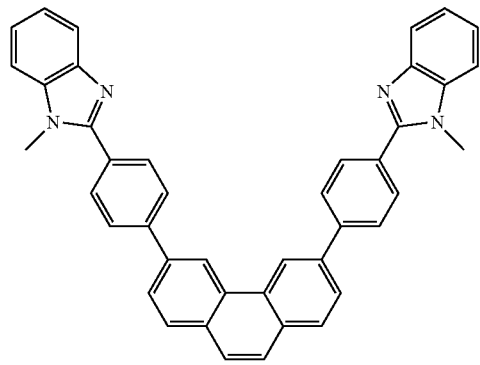
[Formula 5-3]
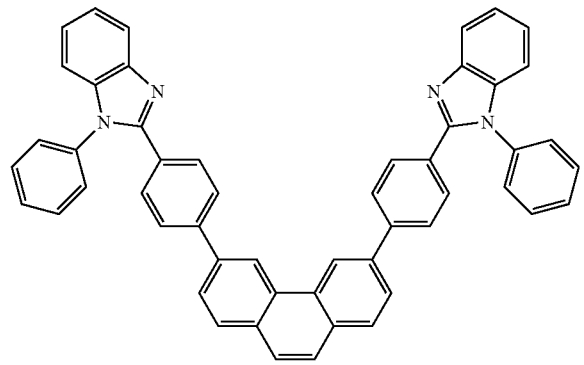
[Formula 6-1]
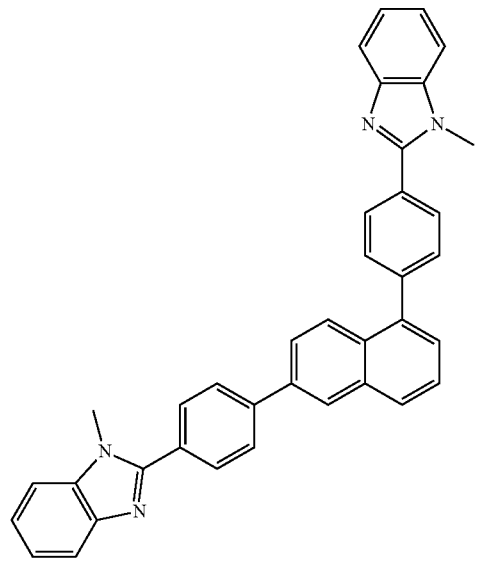
[Formula 6-2]
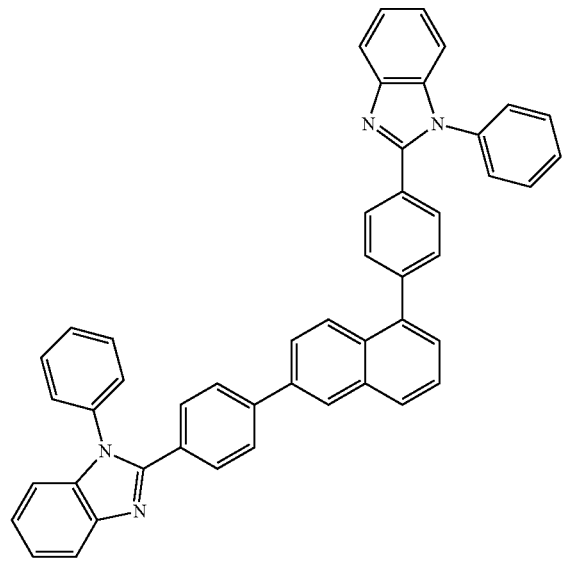
[Formula 6-3]
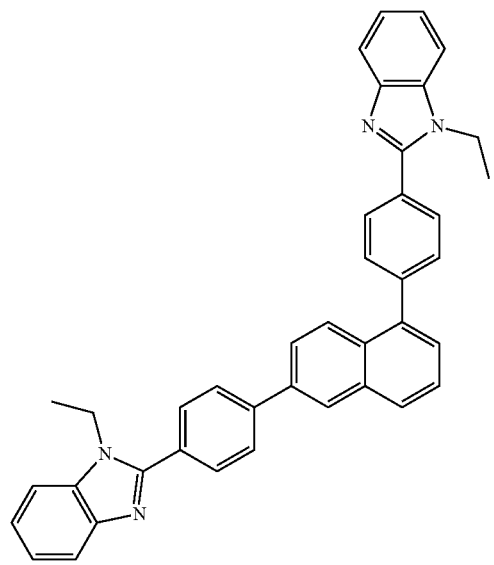
[Formula 6-4]
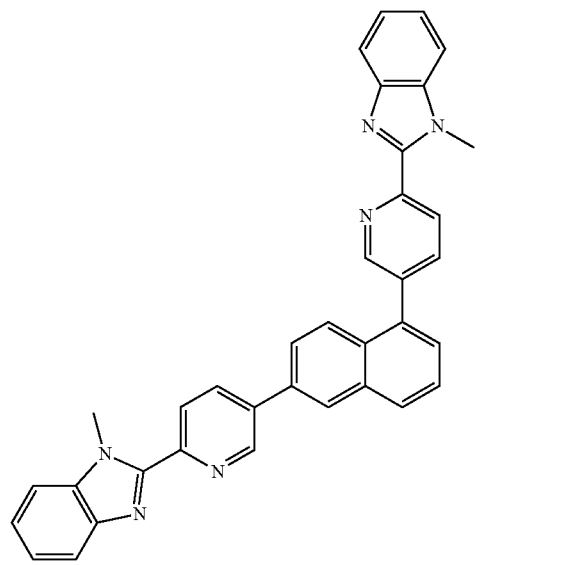

-continued
[Formula 6-5]
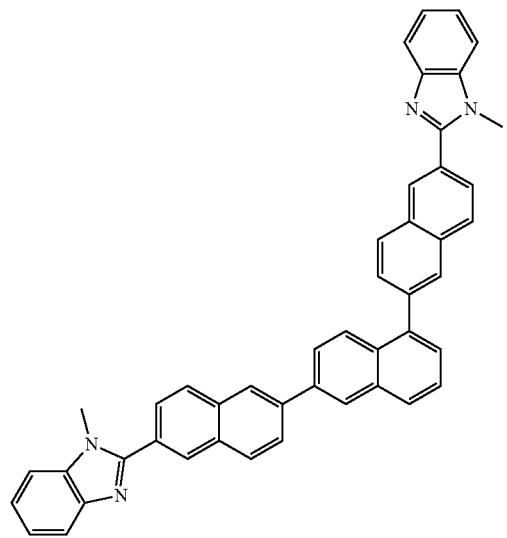
[Formula 6-6]
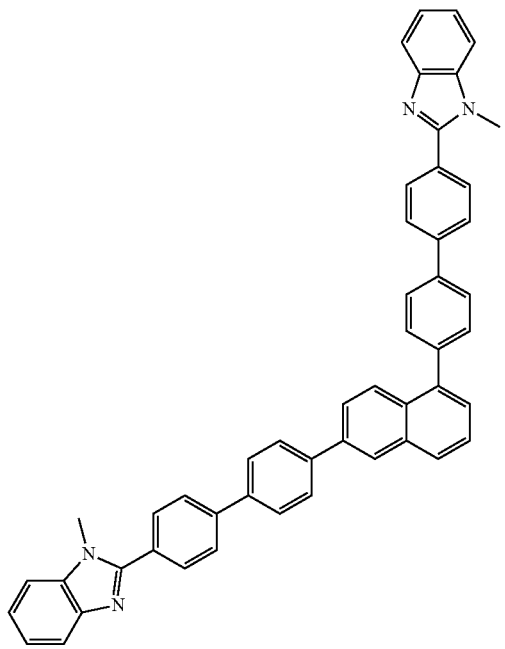
[Formula 6-7]
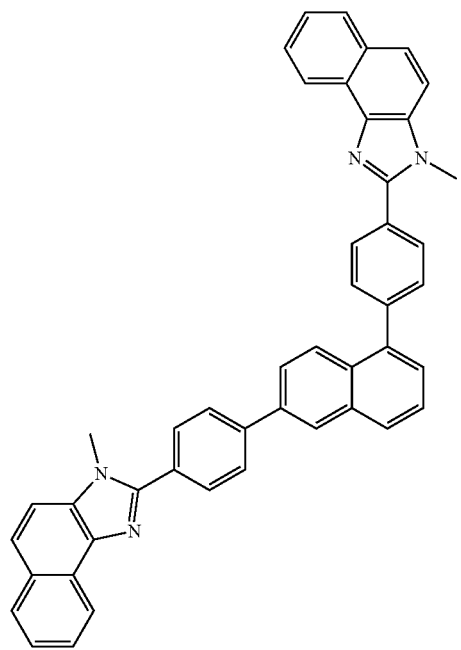
[Formula 6-8]
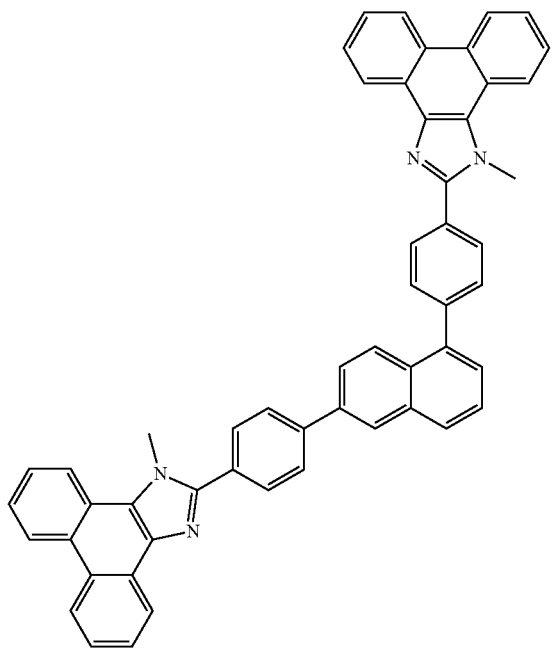

-continued
[Formula 6-9]
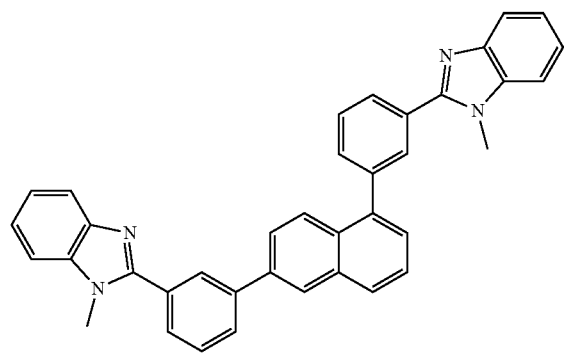
[Formula 6-10]
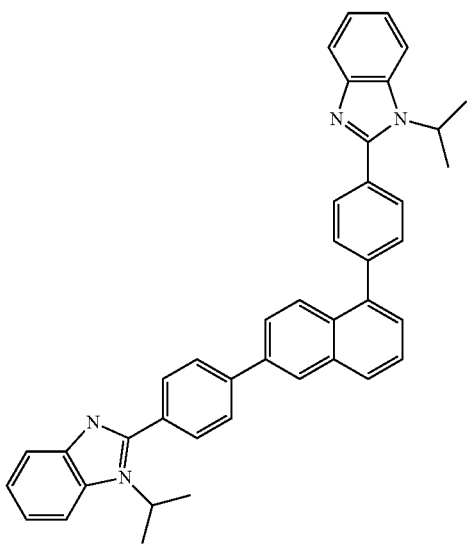
[Formula 6-11]
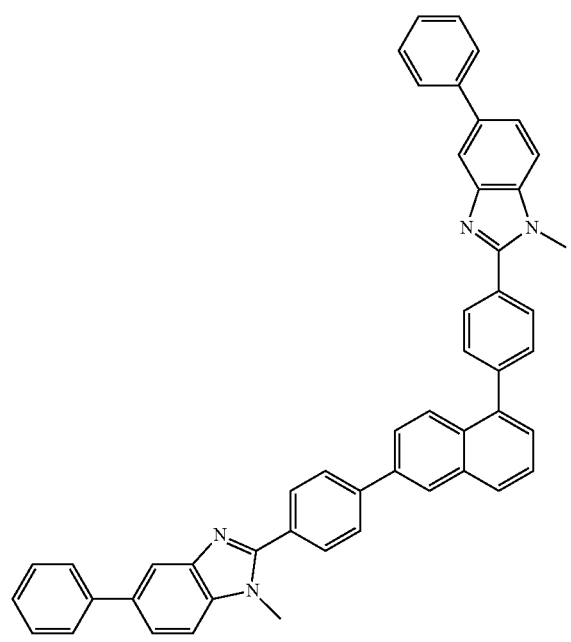
[Formula 6-12]
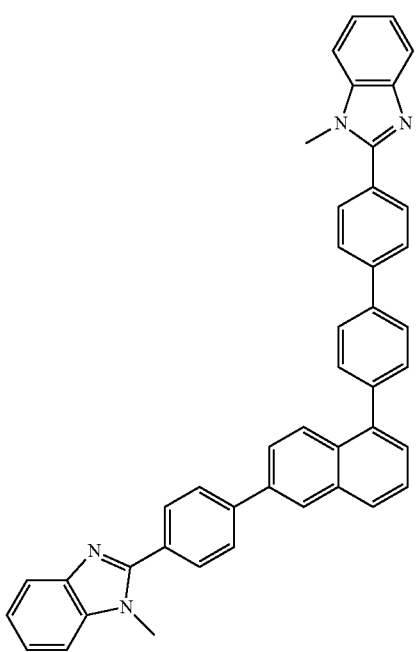

[Formula 6-13]
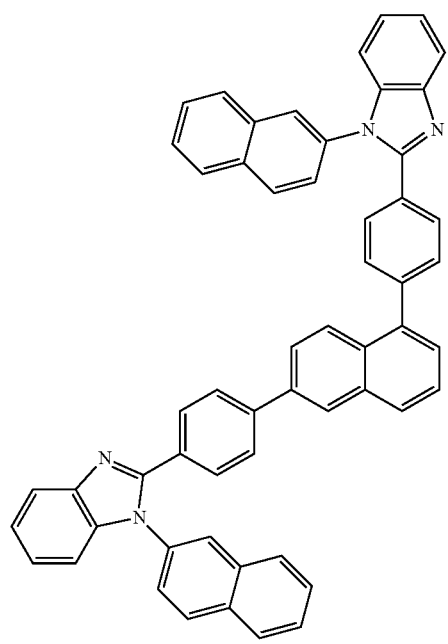
[Formula 6-14]
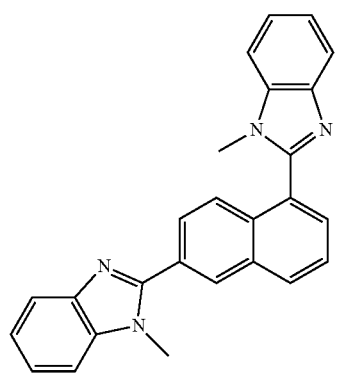
[Formula 7-1]
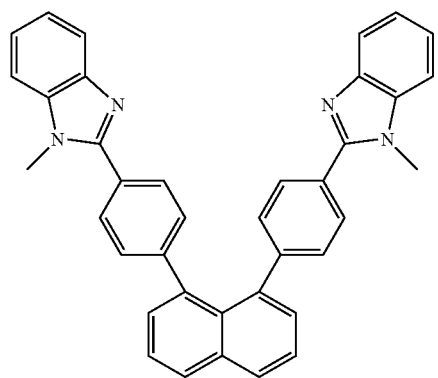
[Formula 7-2]
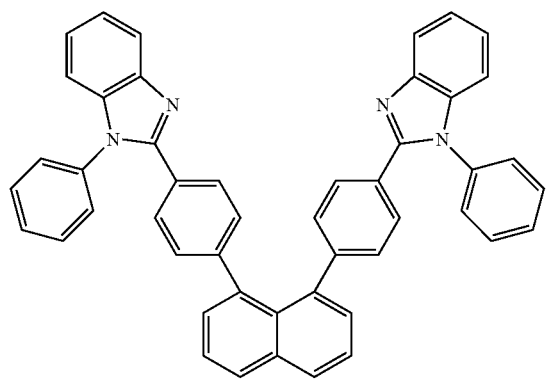
[Formula 7-3]
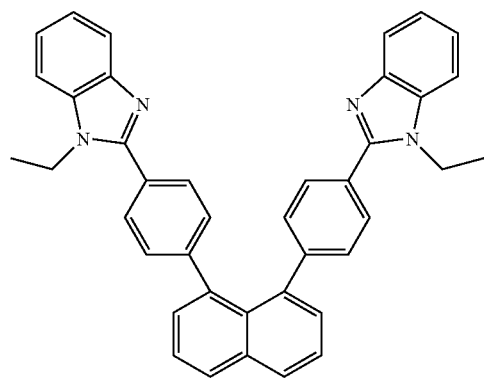
[Formula 7-4]
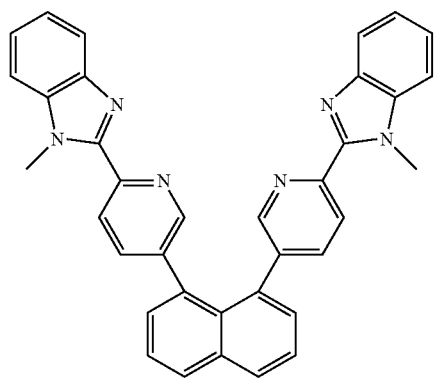

-continued
[Formula 7-5]
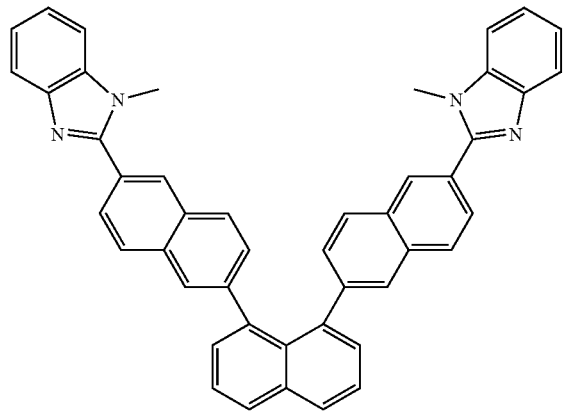
[Formula 7-6]
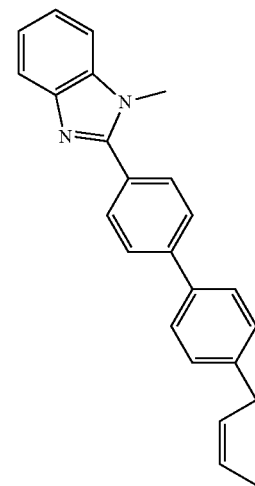
[Formula 7-7]
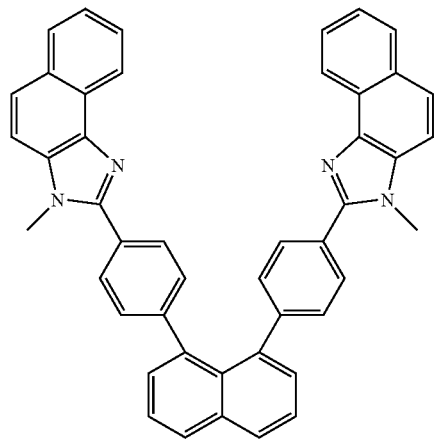
[Formula 7-8]
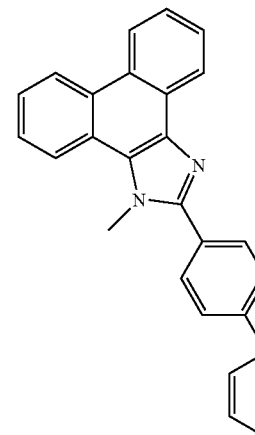
[Formula 7-9]
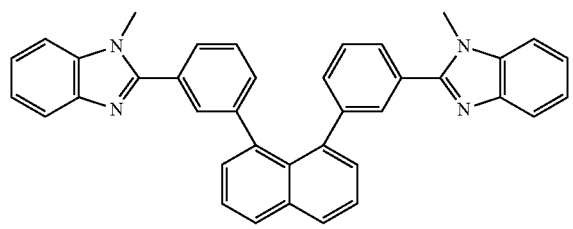
[Formula 7-10]
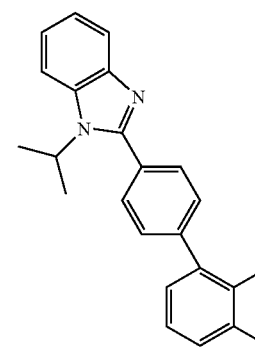

[Formula 7-11]
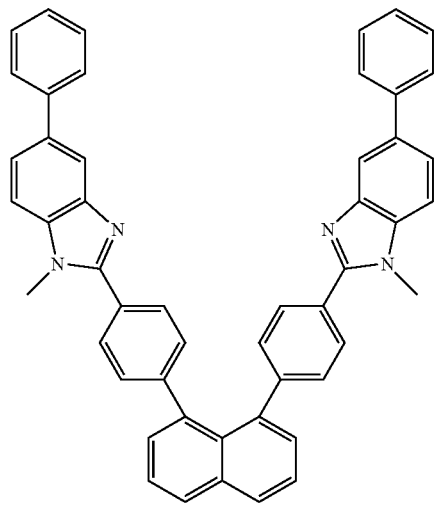
[Formula 7-12]
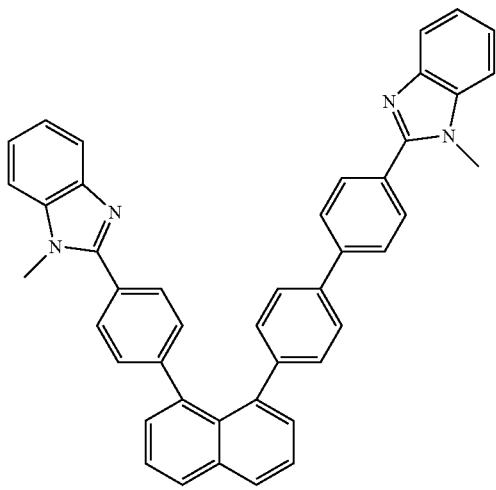
[Formula 7-13]
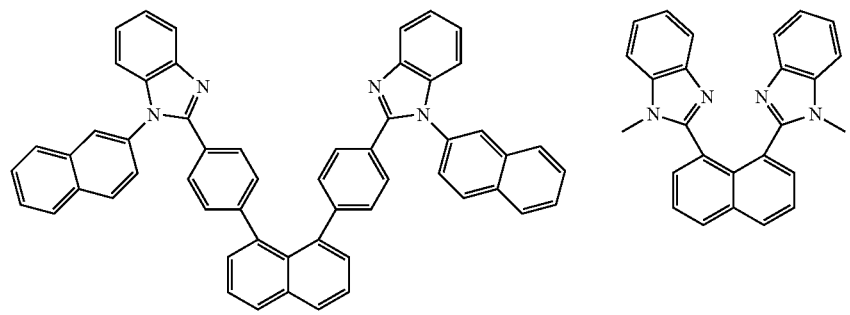
[Formula 7-14]
[Formula 8-1]
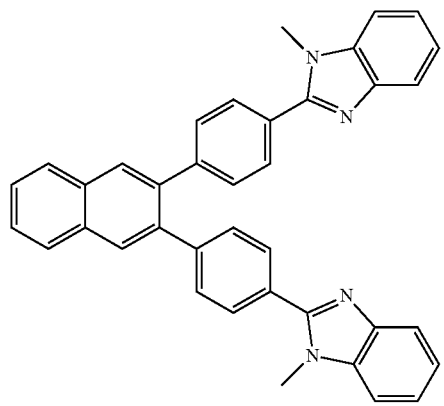
[Formula 8-2]
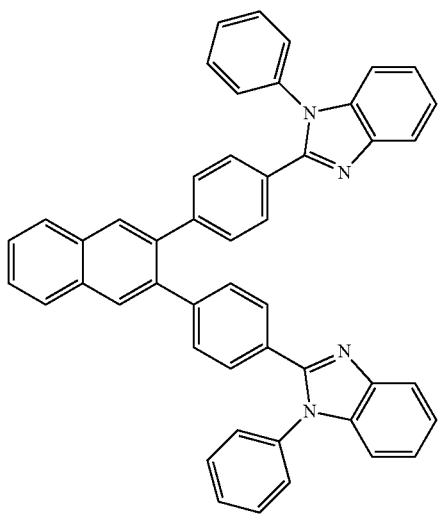

-continued
[Formula 8-3]
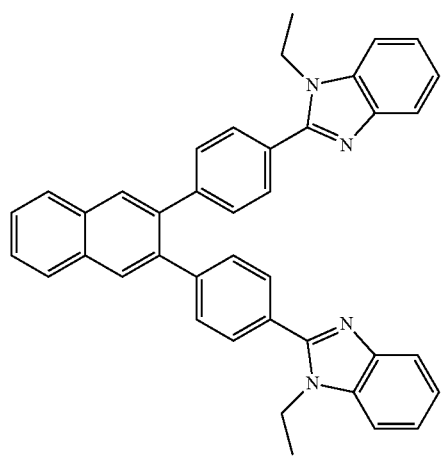
[Formula 8-4]
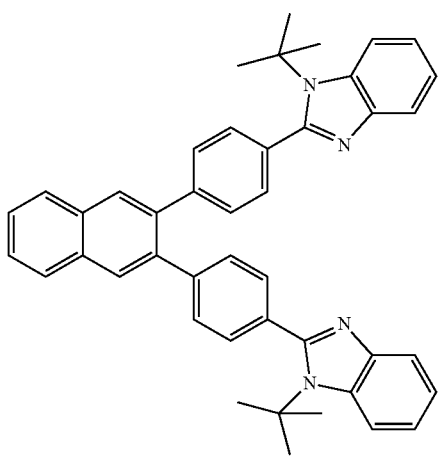
[Formula 8-5]
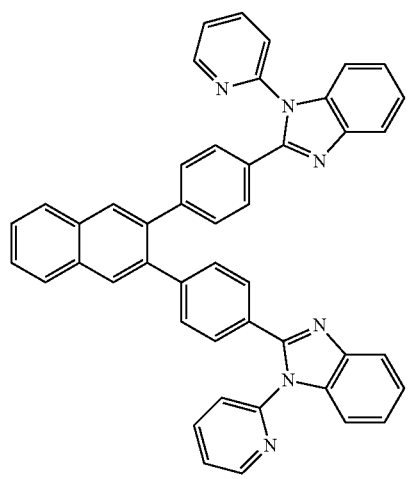
[Formula 8-6]
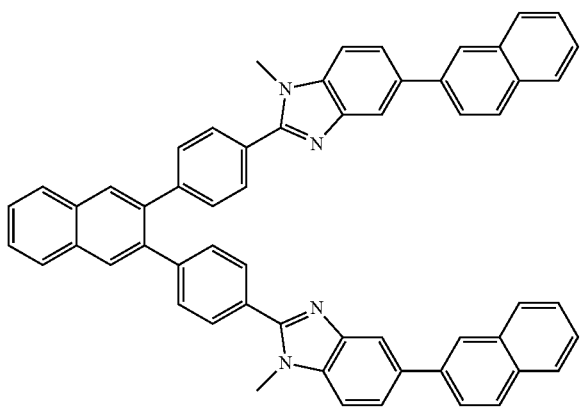
[Formula 8-7]
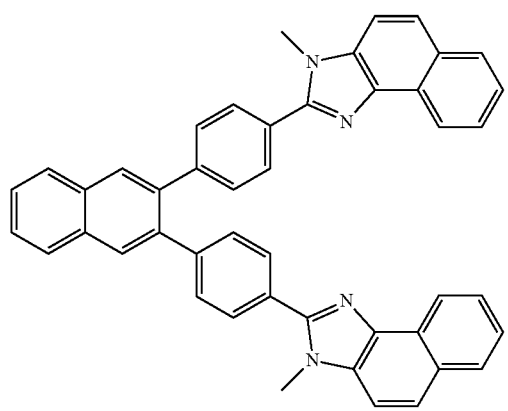
[Formula 8-8]
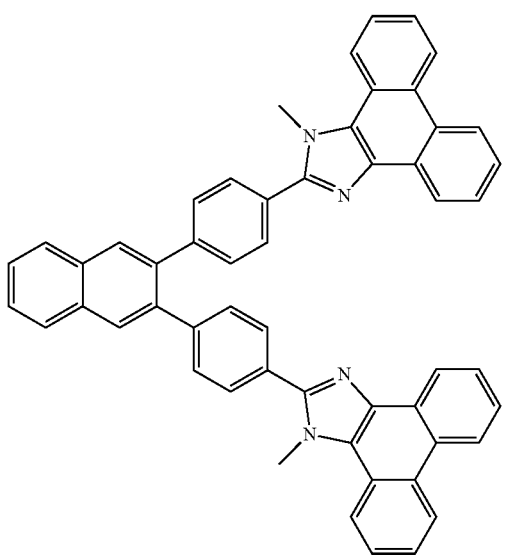

[Formula 8-9]
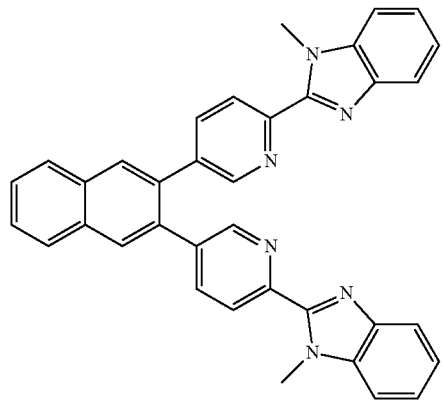
[Formula 8-10]
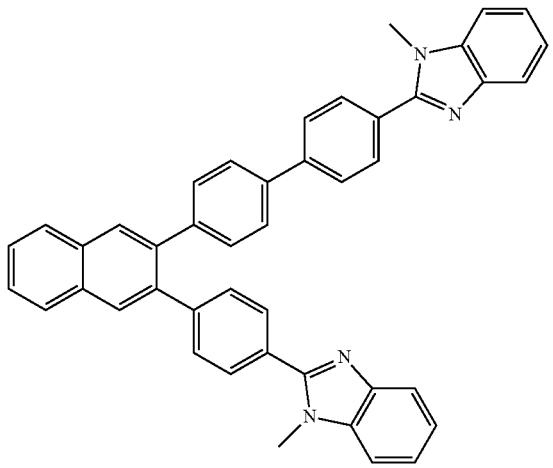
[Formula 8-11]
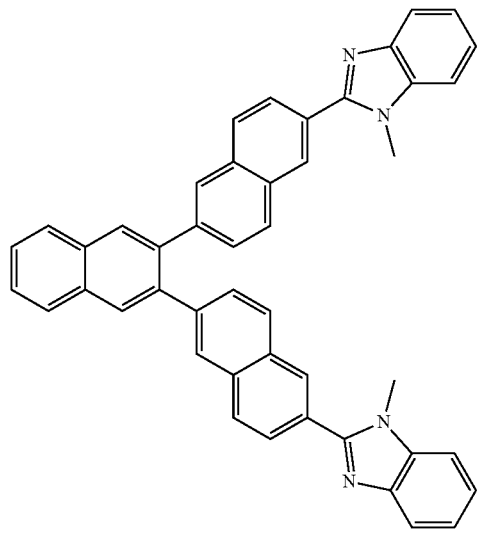
[Formula 8-12]
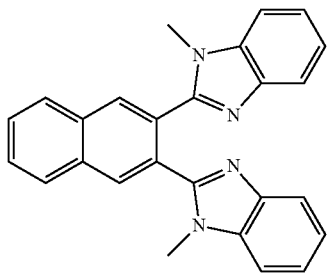
[Formula 8-13]
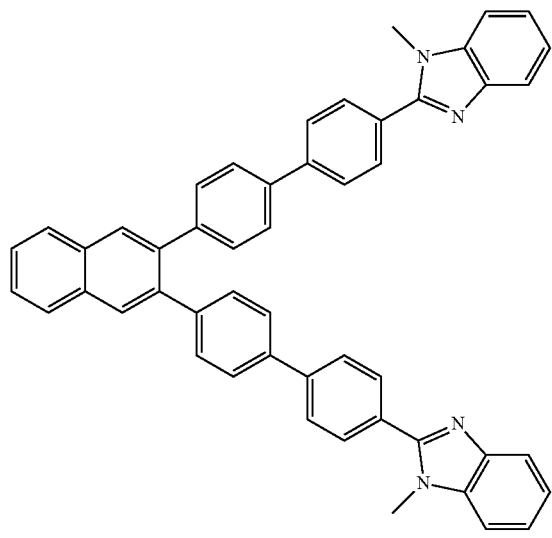
[Formula 8-14]
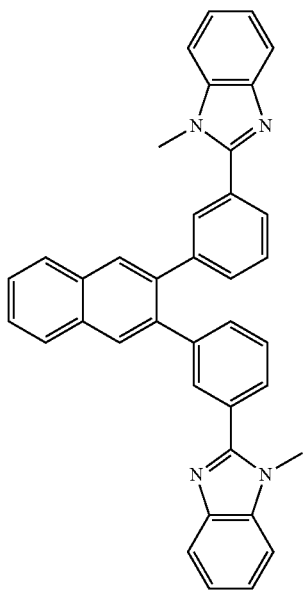

[Formula 9-1]
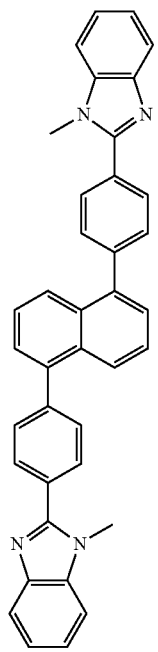
[Formula 9-2]
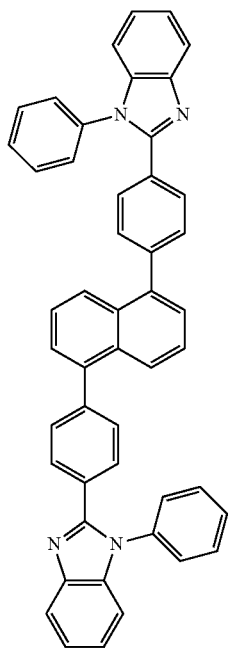
[Formula 9-3]
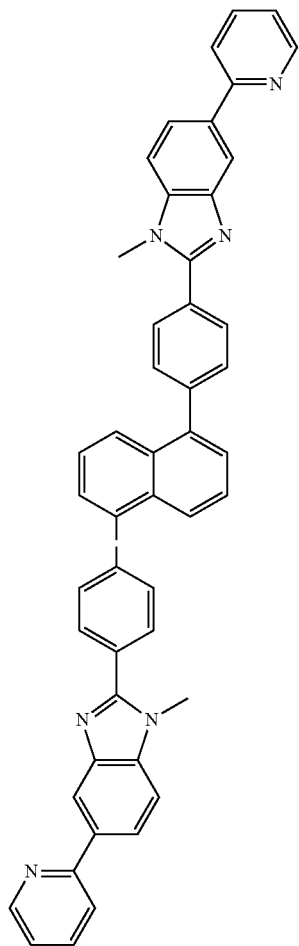
[Formula 9-4]
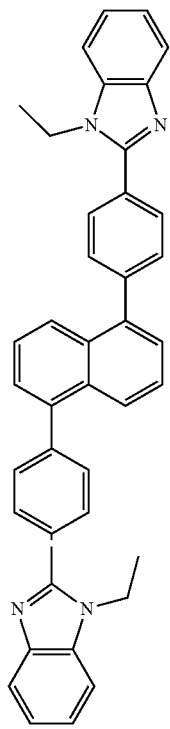

[Formula 9-5]
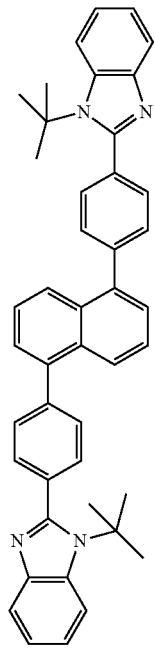
[Formula 9-6]
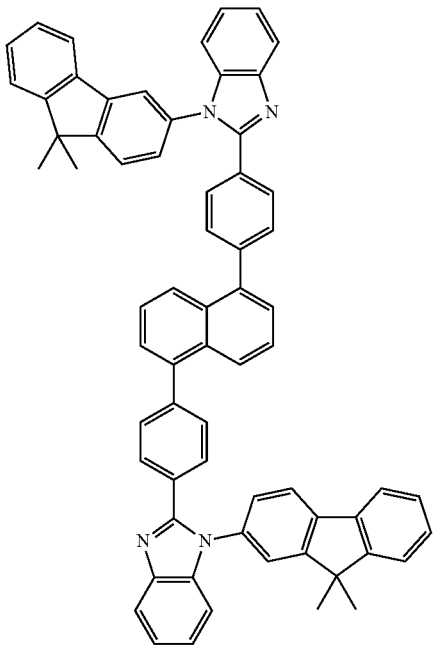
[Formula 9-7]
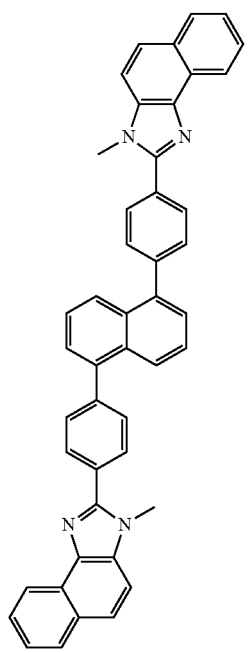
[Formula 9-8]
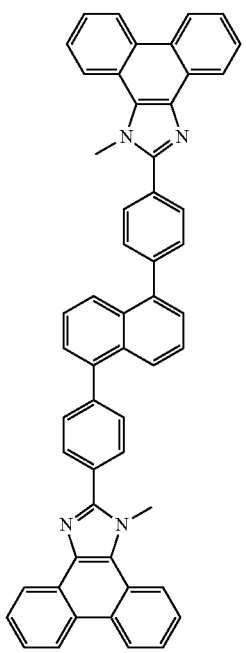

[Formula 9-9]
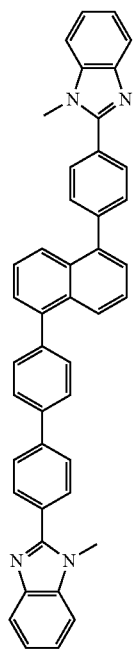
[Formula 9-10]
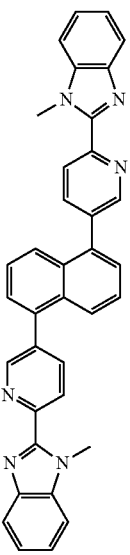
[Formula 9-11]
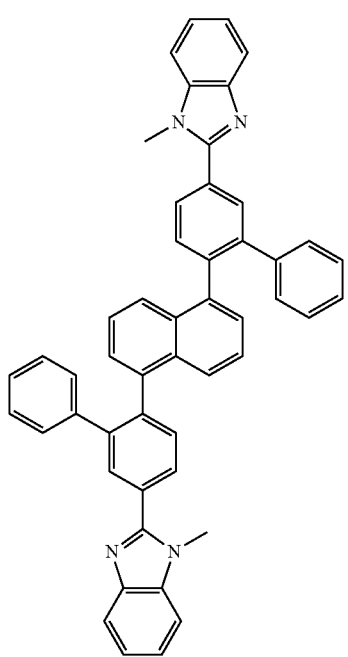
[Formula 9-12]
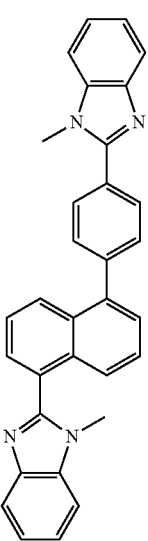

[Formula 9-13]
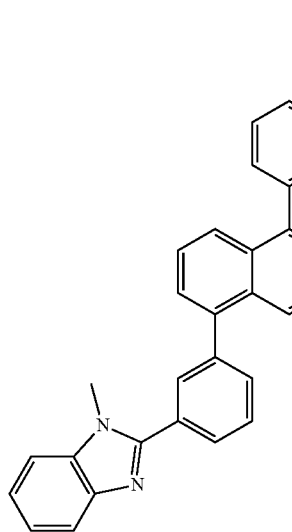
[Formula 9-14]
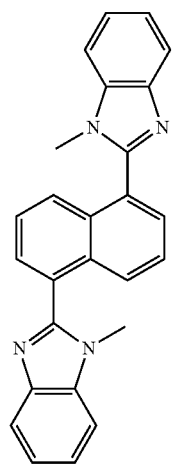
[Formula 10-1]
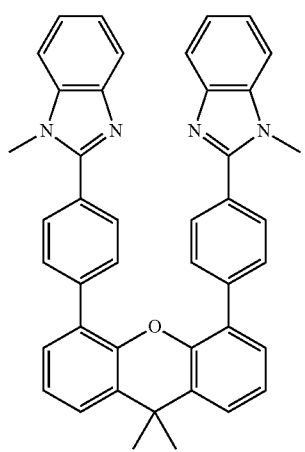
[Formula 10-2]
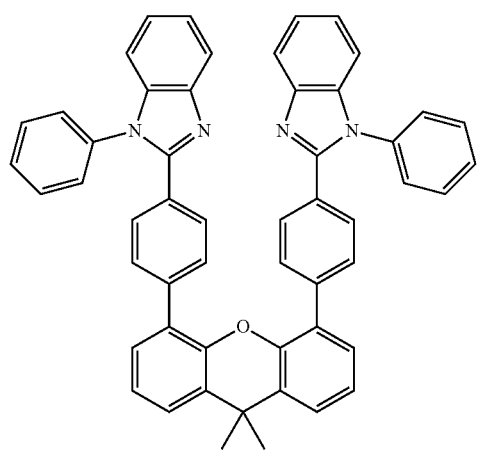
[Formula 10-3]
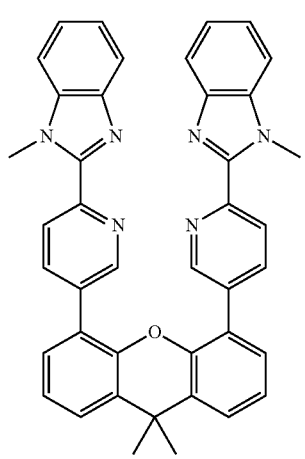

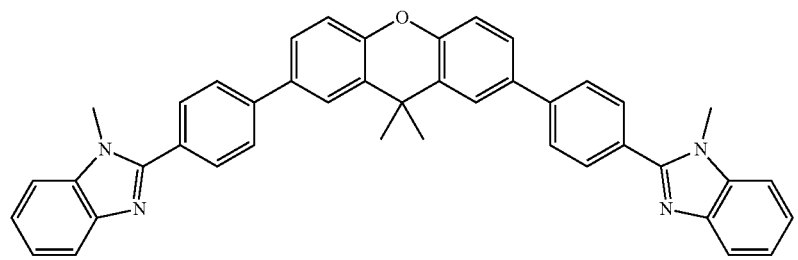
[Formula 10-4]
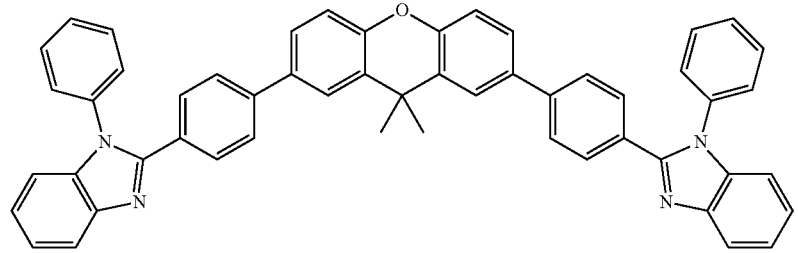
[Formula 10-5]
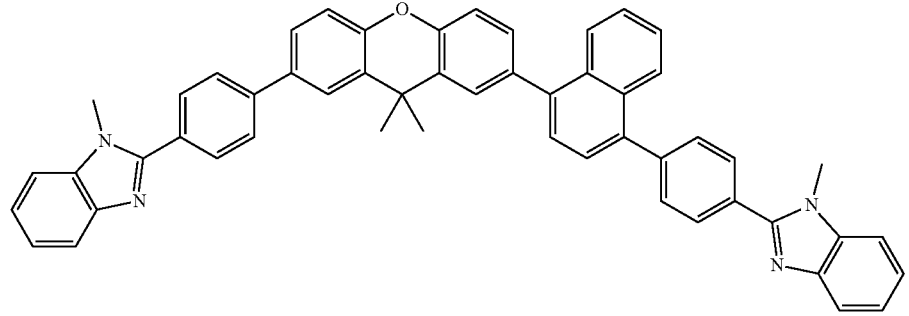
[Formula 10-6]
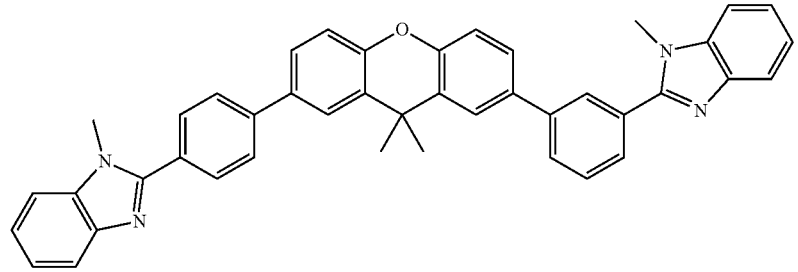
[Formula 10-7]
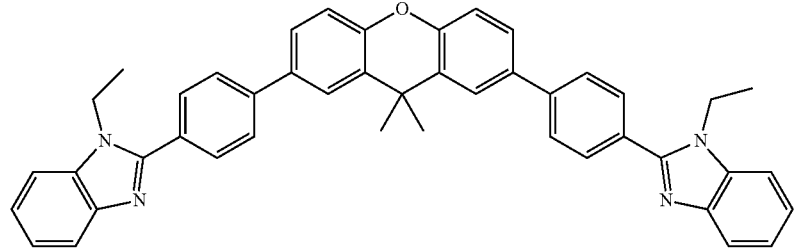
[Formula 10-8]

[Formula 10-9]
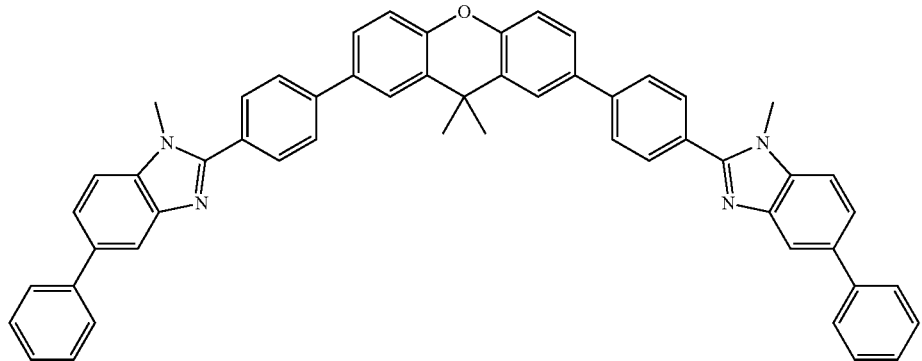
[Formula 10-10]
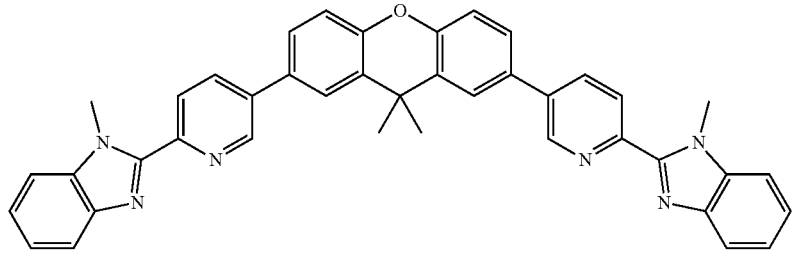
[Formula 10-11]
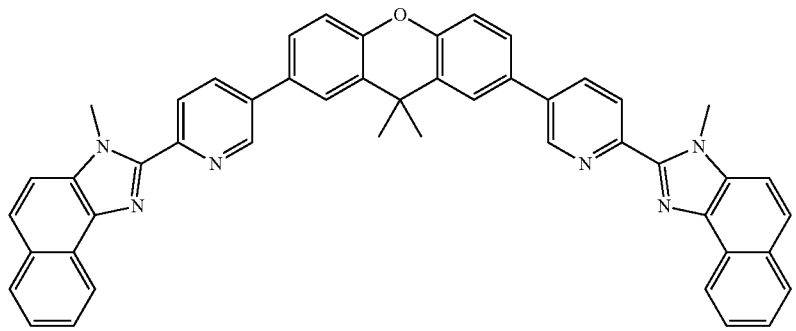
[Formula 10-12]
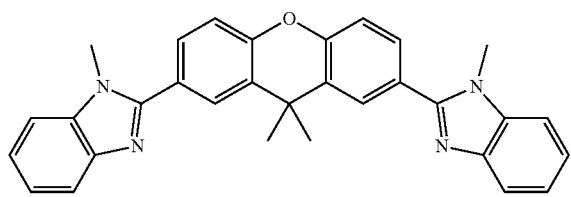
[Formula 10-13]
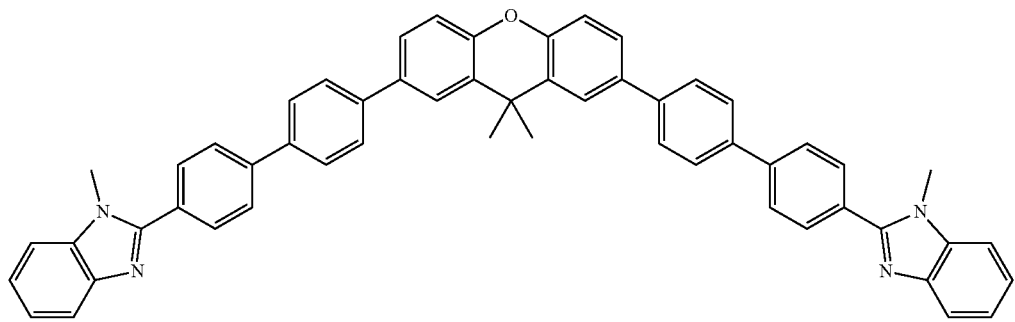

[Formula 10-14]

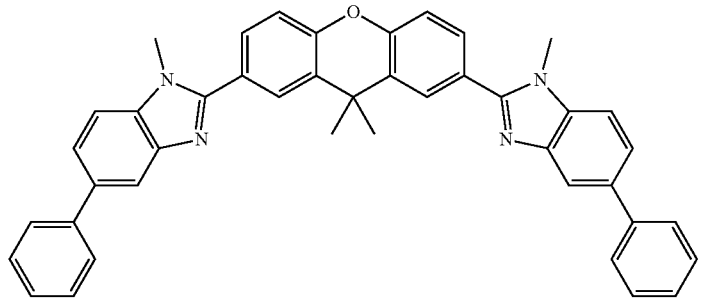

The compound of Formula 1 or 2 may be prepared based on Preparation Examples to be described below.

The present application provides an organic electronic device using the compound of Formula 1 or 2.

In an exemplary embodiment of the present application, the organic electronic device may be composed of a structure including a first electrode, a second electrode, and an organic material layer disposed therebetween. The organic electronic device may be manufactured by a usual method and material of manufacturing an organic electronic device, except that the compound according to the present application is used in the organic material layer of the organic electronic device.

The organic electronic device may be selected from the group consisting of an organic light emitting device, an organic solar cell, an organic photoconductor (OPC) drum, and an organic transistor.

In an exemplary embodiment, the organic material layer of the organic electronic device includes a hole injection layer, or a hole transporting layer, and the hole injection layer or the hole transporting layer includes the nitrogen-containing heterocyclic compound.

In another exemplary embodiment, the organic material layer of the organic electronic device includes a light emitting layer, and the light emitting layer includes the nitrogen-containing heterocyclic compound. As an example, the nitrogen-containing heterocyclic compound may be included as a host of the light emitting layer. As another example, the organic material layer including the nitrogen-containing heterocyclic compound includes the nitrogen-containing heterocyclic compound as a host, and may include another organic compound, a metal, or a metal compound as a dopant.

In another exemplary embodiment, the organic material layer of the organic electronic device includes an electron transporting layer, and the electron transporting layer may include the nitrogen-containing heterocyclic compound.

In another exemplary embodiment, the organic material layer of the organic electronic device includes an electron transporting layer, and the electron transporting layer may include a metal or a metal complex compound along with the nitrogen-containing heterocyclic compound. The metal includes an alkali metal, an alkali earth metal, a rare earth metal, and the like. The alkali metal includes lithium, sodium, and potassium. The alkali earth metal includes magnesium, calcium, and the like. As a specific example, the electron transporting layer may include the nitrogen-containing heterocyclic compound, and a metal such as lithium and calcium, or a metal complex compound.

In another exemplary embodiment, the organic material layer of the organic electronic device includes a charge generating layer, and the charge generating layer may include the nitrogen-containing heterocyclic compound. The charge generating layer may additionally include a metal or a metal complex compound. Examples of the metal are the same as those described above. When the organic material layer includes two or more light emitting units, the charge generating layer may be provided between the light emitting units. The light emitting unit includes a light emitting layer having at least one layer, and may further include an additional organic material layer such as a charge transporting layer, if necessary. Further, the charge generating layer may also be provided between a light emitting layer and any one electrode. Specifically, the charge generating layer may be provided between an anode and a light emitting layer. The charge generating layer may sequentially include an n-type organic material layer such as hexaazatriphenylene and a p-type organic material layer such as NPB on a surface close to a cathode. Specifically, a p-type organic material layer, an n-type organic material layer, and a charge generating layer may be sequentially stacked from the cathode side and provided. In another exemplary embodiment, the organic material layer of the organic electronic device may include a hole injection layer or a hole transporting layer including a compound that includes an aryl amino group, a carbazole group, or a benzocarbazolyl group, in addition to an organic material layer including the nitrogen-containing heterocyclic compound.

Figure 2:
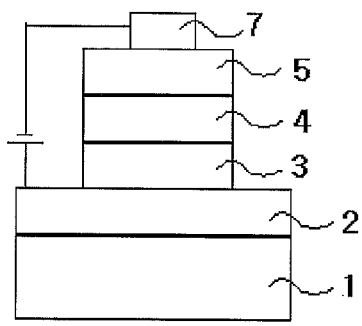
Figure 3:
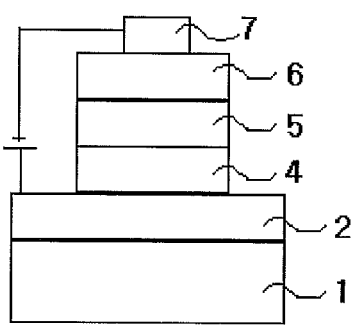
Figure 4:
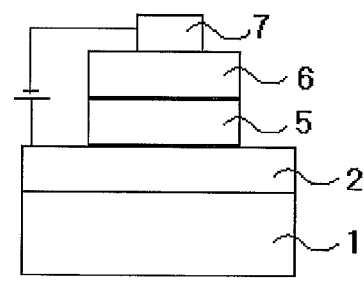
Figure 5:
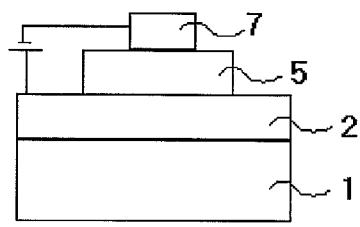

The structure of the organic electronic device according to the present application is illustrated in FIGS. 1 to 5. FIG. 1 illustrates a structure in which an anode 2, a hole injection layer 3, a hole transporting layer 4, a light emitting layer 5, an electron transporting layer 6, and a cathode 7 are stacked on a substrate 1. FIG. 2 illustrates a structure in which the anode 2, the hole injection layer 3, the hole transporting layer 4, the light emitting layer 5, and the cathode 7 are stacked on the substrate 1. FIG. 3 illustrates a structure in which the anode 2, the hole transporting layer 4, the light emitting layer 5, the electron transporting layer 6, and the cathode 7 are stacked on the substrate 1. FIG. 4 illustrates a structure in which the anode 2, the light emitting layer 5, the electron transporting layer 6, and the cathode 7 are stacked on the substrate 1. FIG. 5 illustrates a structure in which the anode 2, the light emitting layer 5, and the cathode 7 are stacked on the substrate 1. FIGS. 1 to 5 are provided only for illustrating the structure of the device, but the scope of the present application is not limited thereto. FIGS. 1 to 5 describe only a structure in which an anode, an organic material layer, and a cathode are sequentially stacked on a substrate, but the present application also includes a structure in which a cathode, an organic material layer, and an anode are sequentially stacked on a substrate.

For example, the organic electronic device according to the present application may be manufactured by depositing a metal or a metal oxide having conductivity, or an alloy thereof on a substrate to form an anode by using a physical vapor deposition (PVD) method such as sputtering or e-beam evaporation, forming an organic material layer including a hole injection layer, a hole transporting layer, a light emitting layer, and an electron transporting layer thereon, and then depositing a material which may be used as a cathode thereon.

In addition to these methods, an organic electronic device may also be manufactured by sequentially depositing an organic material layer from a cathode material, and an anode material on a substrate (International Publication No. 2003/012890). The organic material layer may be a multi-layer structure including the hole injection layer, the hole transporting layer, the light emitting layer, the electron transporting layer and the like, but may be a mono-layer structure without being limited thereto. In addition, the organic material layer may be manufactured with a fewer number of layers by using various polymer materials by a solvent process other than a deposition method, such as, for example, spin coating, dip coating, doctor blading, screen printing, inkjet printing, a thermal transfer method or the like.

It is preferred that as the anode material, materials having a high work function are usually used so as to facilitate the injection of holes into the organic material layer. Specific examples of the anode material which may be used in the present invention include: a metal such as vanadium, chromium, copper, zinc and gold, or an alloy thereof; a metal oxide such as zinc oxide, indium oxide, indium tin oxide (ITO) and indium zinc oxide (IZO); a combination of a metal and an oxide, such as ZnO:Al or SnO$_2$:Sb; a conductive polymer such as poly(3-methylthiophene), poly[3,4-(ethylene-1,2-dioxy)thiophene] (PEDT), polypyrrole and polyaniline; and the like, but are not limited thereto.

It is preferred that as the cathode material, materials having a low work function are usually used so as to facilitate the injection of electrons into the organic material layer. Specific examples of the cathode material include a metal such as magnesium, calcium, sodium, potassium, titanium, indium, yttrium, lithium, gadolinium, aluminum, silver, tin, and lead, or an alloy thereof; a multi-layer structured material such as LiF/Al or LiO$_2$/Al, and the like, but are not limited thereto.

The hole injection material is a material that is capable of well accepting holes from the anode at low voltage, and the highest occupied molecular orbital (HOMO) of the hole injection material is preferably a value between the work function of the anode material and the HOMO of the neighboring organic material layer. Specific examples of the hole injection material include metal porphyrine, oligothiophene, arylamine-based organic materials, hexanitrile hexaazatriphenylene, quinacridone-based organic materials, perylene-based organic materials, antraquinone, and polyaniline-based and polythiophene-based conductive polymers, and the like, but are not limited thereto.

The hole transporting material is suitably a material having high hole mobility, which may accept holes from the anode or the hole injection layer and transfer the holes to the light emitting layer. Specific examples thereof include arylamine-based organic materials, conductive polymers, block copolymers having both conjugated portions and non-conjugated portions, and the like, but are not limited thereto.

The light emitting material is a material that is capable of emitting light in a visible light region by accepting and recombining holes from the hole transporting layer and electrons from the electron transporting layer, respectively, and preferably a material having high quantum efficiency for fluorescence and phosphorescence. Specific examples thereof include 8-hydroxy-quinoline-aluminum complex (Alq$_3$); carbazole-based compounds; dimerized styryl compounds; BAlq; 10-hydroxybenzoquinoline-metal compounds; benzoxazole-based, benzothiazole-based and benzimidazole-based compounds; poly(p-phenylenevinylene) (PPV)-based polymers; spiro compounds; and polyfluorene, rubrene, and the like, but are not limited thereto.

The electron transporting material is suitably a material having high electron mobility, which may accept electrons from the cathode and transfer the electrons to the light emitting layer. Specific examples thereof include Al complexes of 8-hydroxyquinoline; complexes including Alq$_3$; organic radical compounds; hydroxyflavone-metal complexes, and the like, but are not limited thereto.

The organic electronic device according to the present application may be a front side light emission type, a rear side light emission type or a both-side light emission type according to the materials used.

EXAMPLE

Hereinafter, the present invention will be described in more detail through Preparation Examples and Experimental Examples, but the scope of the present application is not limited by the following Preparation Examples and Experimental Examples.

Preparation Example

<Preparation Example 1> Preparation of the Following Compounds A-1 and A-2

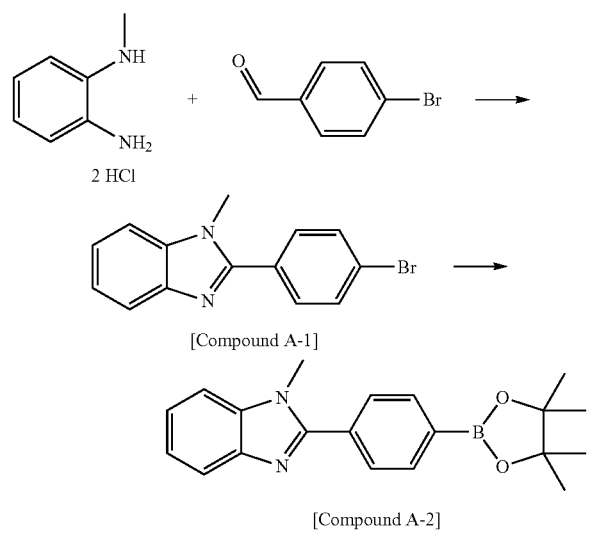

(Preparation Example 1-1) Preparation of Compound A-1

N-methyl-1,2-benzenediamine dihydrochloride (19.5 g, 99.95 mmol) and 4-bromobenzaldehyde (18.5 g, 99.98 mmol) were suspended in 1,4-dioxane (200 mL) and acetic acid (AcOH) (20 mL). The obtained mixture was stirred under reflux for about 6 hours, and cooled to normal temperature. The mixture was diluted with water (100 mL), and then the produced solid was filtered, and washed with water and hexane to prepare Compound A-1 (20.7 g, 72%). MS: $[M+H]^+=288$ (Preparation Example 1-2) Preparation of Compound A-2

In Compound A-3 (11.7 g, 40.7 mmol) prepared in Preparation Example 1-1, bis(pinacolato)diboron (11.4 g, 44.9 mmol) and potassium acetate (KOAc) (12.0 g, 122 mmol) were suspended in dioxane (250 mL). $Pd(dba)_2$ (0.70 g, 3 mol %) and $PCy_3$ (0.69 g, 6 mol %) were added to the suspension. The mixture was stirred under reflux for about 8 hours, and cooled to normal temperature. The mixture was diluted with water (250 mL) and extracted with $CH_2Cl_2$ (3×100 mL). The organic extract dried over magnesium sulfate ($MgSO_4$), and then filtered. The filtrate was concentrated under reduced pressure, and recrystallized with ethyl ether and hexane to prepare Compound A-2 (10.2 g, 75%). MS: $[M+H]^+=335$ <Preparation Example 2> Preparation of the Following Compounds A-3 and A-4

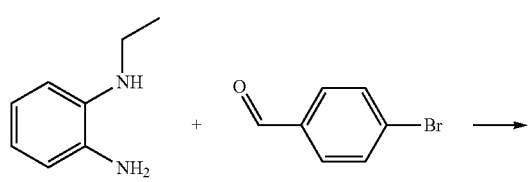

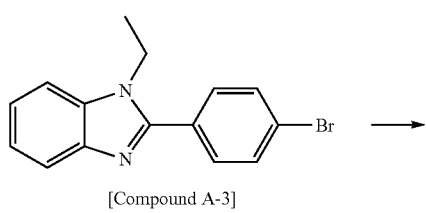

[Compound A-3]

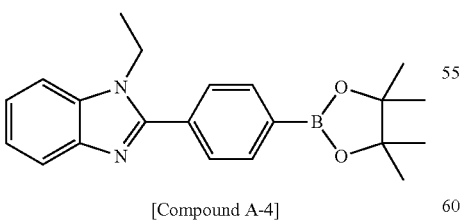

[Compound A-4]

Compound A-4 was prepared in the same manner as in Preparation Example 1, except that N-ethyl-1,2-benzenediamine was used instead of N-methyl-1,2-benzenediamine dihydrochloride in Preparation Example 1. MS: $[M+H]^+=349$ <Preparation Example 3> Preparation of the Following Compounds A-5 and A-6

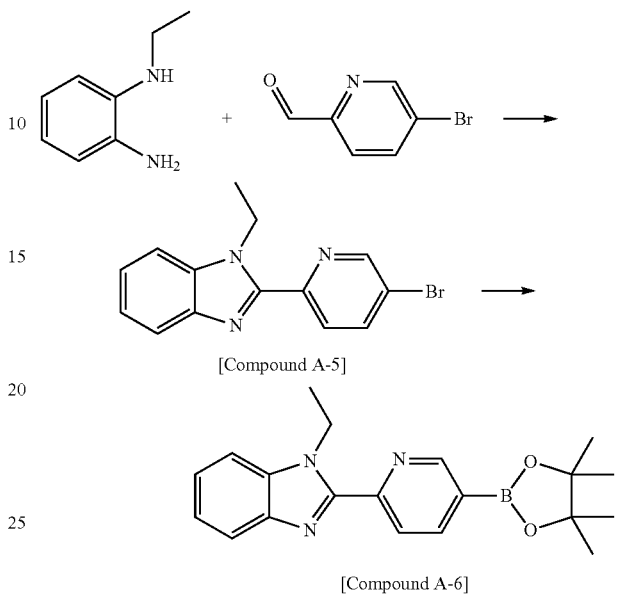

[Compound A-5]

[Compound A-6]

Compound A-6 was prepared in the same manner as in Preparation Example 1, except that 2-formyl-5-bromopyridine was used instead of 4-bromobenzaldehyde in Preparation Example 1. MS: $[M+H]^+=350$ <Preparation Example 4> Preparation of the Following Compounds A-7 and A-8

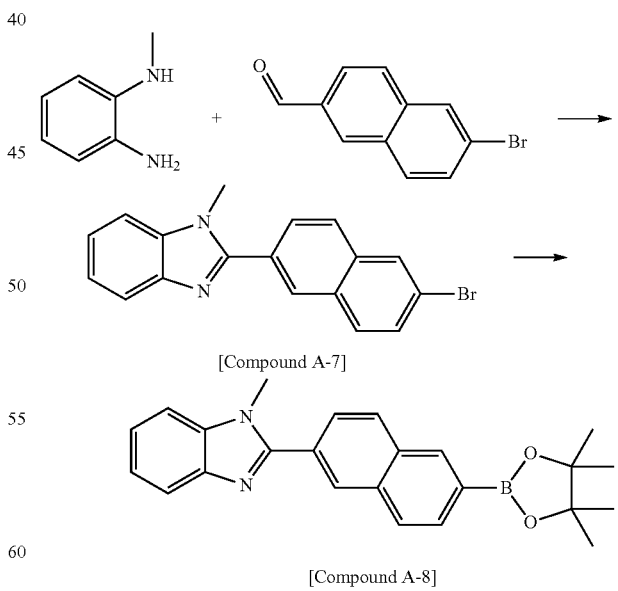

[Compound A-7]

[Compound A-8]

Compound A-8 was prepared in the same manner as in Preparation Example 1, except that 6-bromo-2-naphthaldehyde was used instead of 4-bromobenzaldehyde in Preparation Example 1. MS: $[M+H]^+=385$ <Preparation Example 5> Preparation of the Following Compounds A-9 and A-10

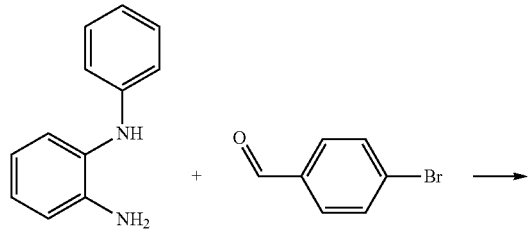

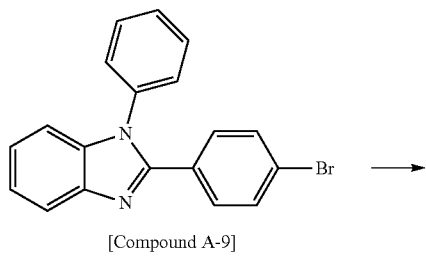

[Compound A-9]

[Compound A-10]

Compound A-10 was prepared in the same manner as in Preparation Example 1, except that N-phenylbenzene-1,2-diamine was used instead of N-methyl-1,2-benzenediamine dihydrochloride in Preparation Example 1. MS: $[M+H]^+= 396$ <Preparation Example 6> Preparation of the Following Compounds A-11 and A-12

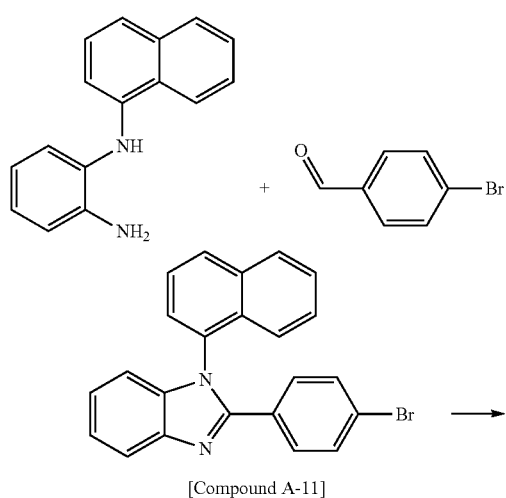

[Compound A-11]

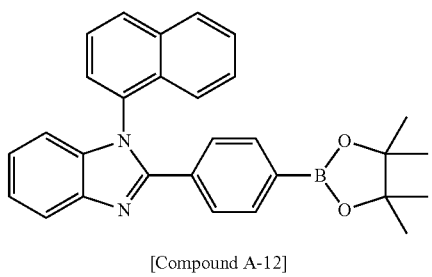

[Compound A-12]

Compound A-12 was prepared in the same manner as in Preparation Example 1, except that N-(naphthalen-1-yl)benzene-1,2-diamine was used instead of N-methyl-1,2-benzenediamine dihydrochloride in Preparation Example 1. MS: $[M+H]^+=446$ <Preparation Example 101> Preparation of Compound of Formula 3-1

[Formula 3-1]

2,7-dibromonaphthalene (2.86 g, 10.0 mmol) and Compound A-2 (7.21 g, 21.0 mmol) were dissolved in tetrahydrofuran (100 mL), a 2 M potassium carbonate aqueous solution (30 mL) was added thereto, tetrakis triphenylphosphino palladium (Pd(PPh$_3$)$_4$) (231 mg, 2 mol %) was put thereinto, and then the mixture was stirred under reflux for 5 hours. The temperature was decreased to normal temperature, and the produced solid was filtered. The filtered solid was recrystallized with chloroform and ethanol and filtered, and then dried to prepare a compound of Formula 3-1 (4.06 g, 75%). MS: $[M+H]^+=541$ <Preparation Example 102> Preparation of Compound of Formula 3-2

<Preparation Example 103> Preparation of Compound of Formula 3-3

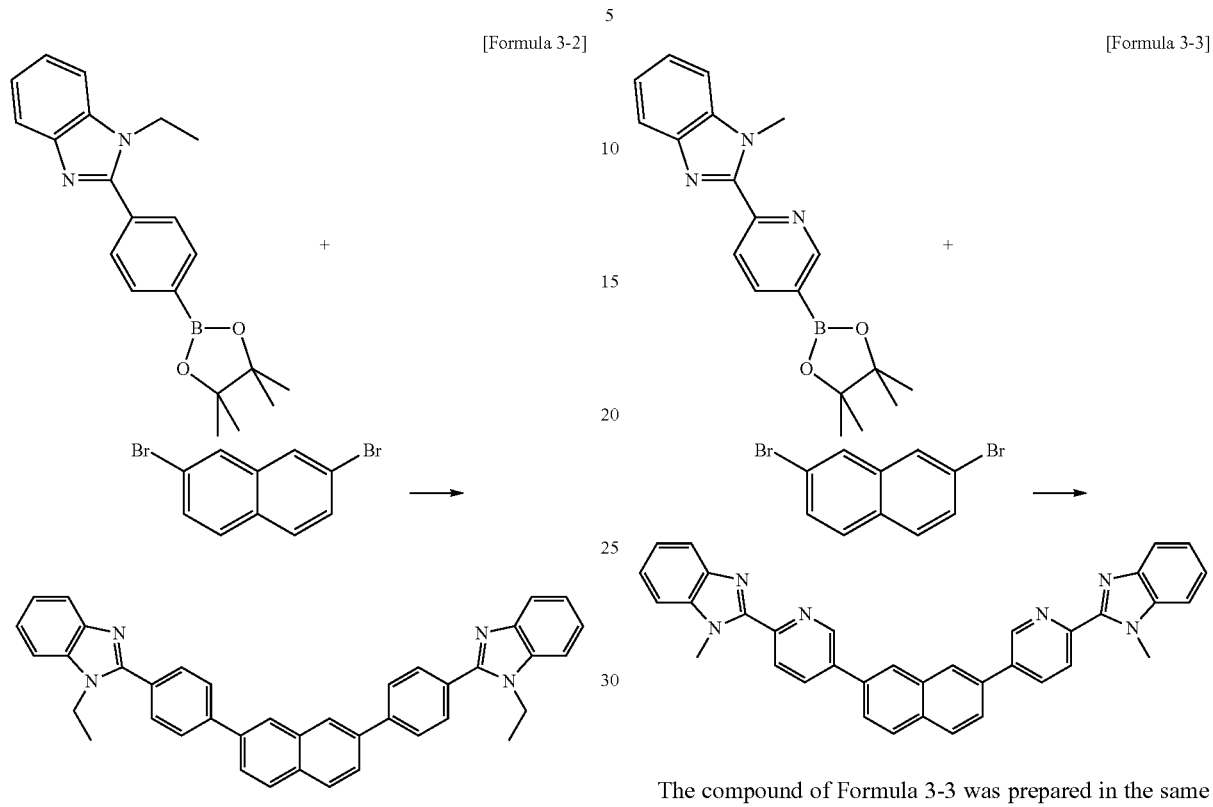

[Formula 3-2]

[Formula 3-3]

The compound of Formula 3-2 was prepared in the same manner as in Preparation Example 101, except that compound A-4 was used instead of Compound A-2 in Preparation Example 101. MS: [M+H]$^+$=569

The compound of Formula 3-3 was prepared in the same manner as in Preparation Example 101, except that Compound A-6 was used instead of Compound A-2 in Preparation Example 101. MS: [M+H]$^+$=543

<Preparation Example 104> Preparation of Compound of Formula 3-4

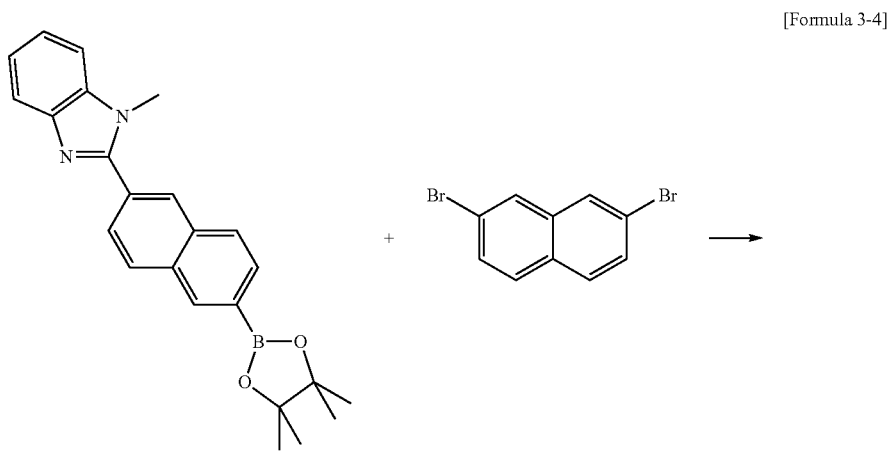

[Formula 3-4]

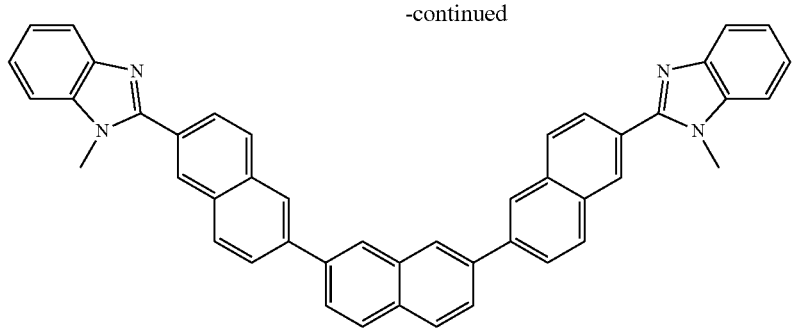
The compound of Formula 3-4 was prepared in the same manner as in Preparation Example 101, except that Compound A-8 was used instead of Compound A-2 in Preparation Example 101. MS: [M+H]$^+$=641
<Preparation Example 105> Preparation of Compound of Formula 4-1
[Formula 4-1]
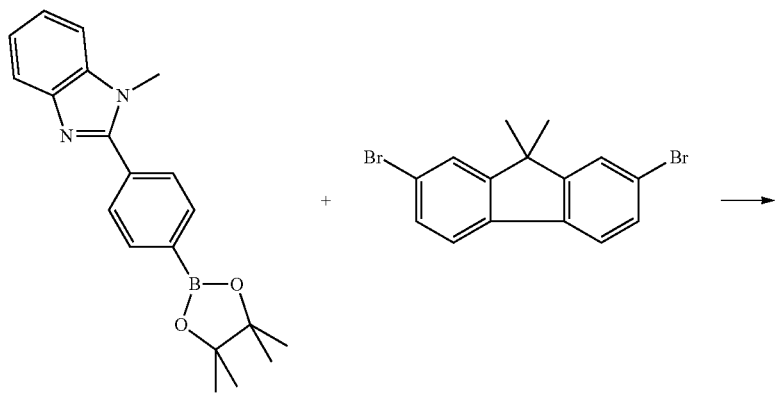
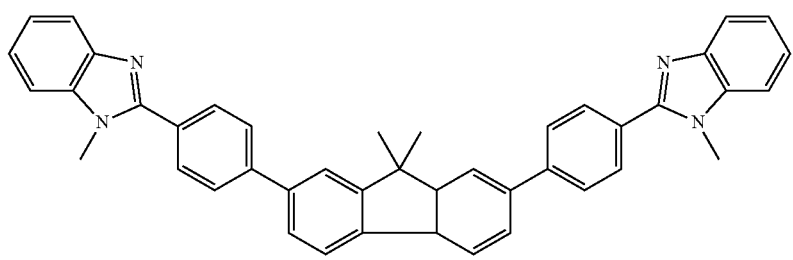

The compound of Formula 4-1 was prepared in the same manner as in Preparation Example 101, except that 2,7-dibromo-9,9-dimethylfluorene was used instead of 2,7-dibromobenzene in Preparation Example 101. MS: [M+H]$^+$=607

<Preparation Example 106> Preparation of Compound of Formula 3-13

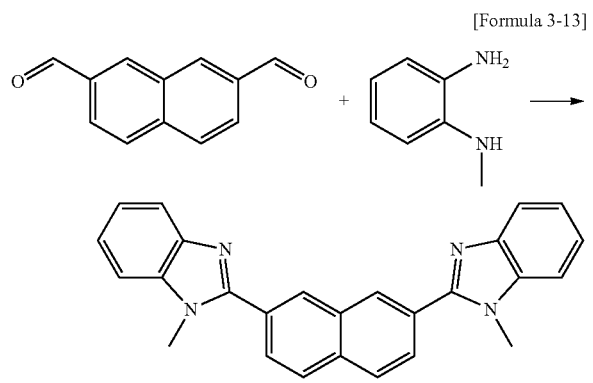

[Formula 3-13]

N-methyl-1,2-benzenediamine dihydrochloride (19.5 g, 99.95 mmol) and 2.7-naphthalenedicabaldehyde (8.767 g, 47.6 mmol) were suspended in 1,4-dioxane (200 mL) and acetic acid (AcOH) (20 mL). The obtained mixture was stirred under reflux for about 6 hours, and cooled to normal temperature. The mixture was diluted with water (100 mL), and then the produced solid was filtered and washed with water and hexane. The filtered solid was recrystallized with chloroform and ethanol and filtered, and then dried to prepare a compound of Formula 3-13 (15.16 g, 82%). MS: [M+H]$^+$=388

<Preparation Example 107> Preparation of Compound of Formula 3-14

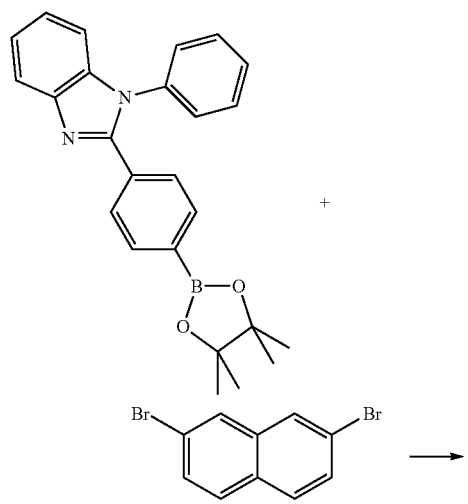

[Formula 3-14]

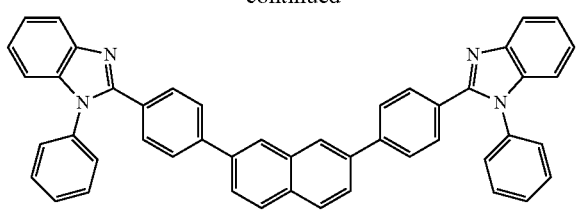

The compound of Formula 3-14 was prepared in the same manner as in Preparation Example 101, except that Compound A-10 was used instead of Compound A-2 in Preparation Example 101. MS: [M+H]$^+$=664

<Preparation Example 108> Preparation of Compound of Formula 5-2

[Formula 5-2]

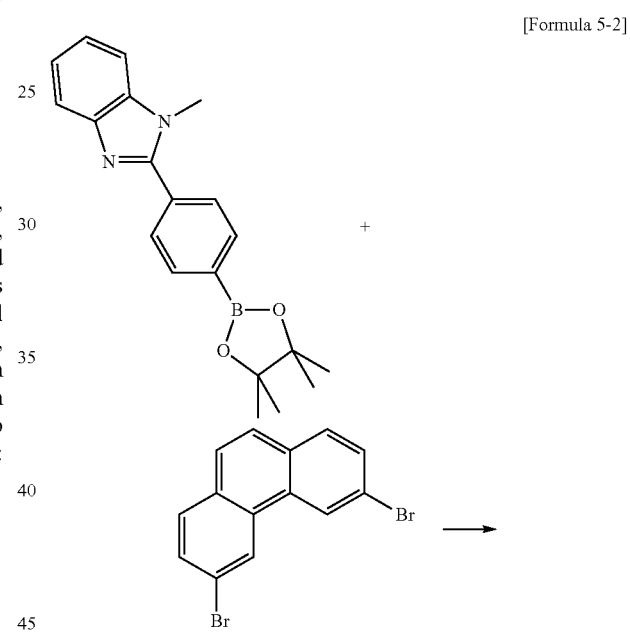

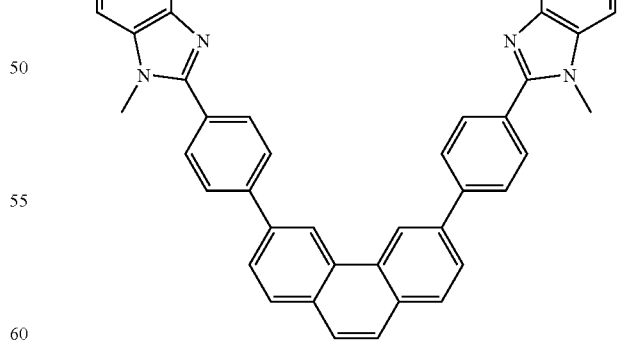

The compound of Formula 5-2 was prepared in the same manner as in Preparation Example 101, except that the compound 3,6-dibromophenanthrene was used instead of the compound 2,7-dibromonaphthalene in Preparation Example 101. MS: [M+H]$^+$=590

<Preparation Example 109> Preparation of Compound of Formula 5-3
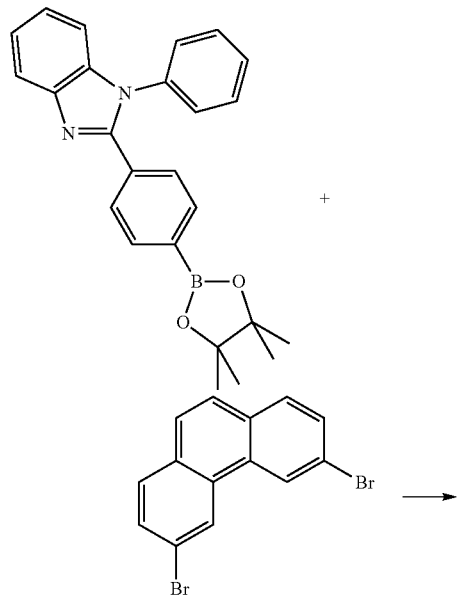
+
[Formula 5-3]
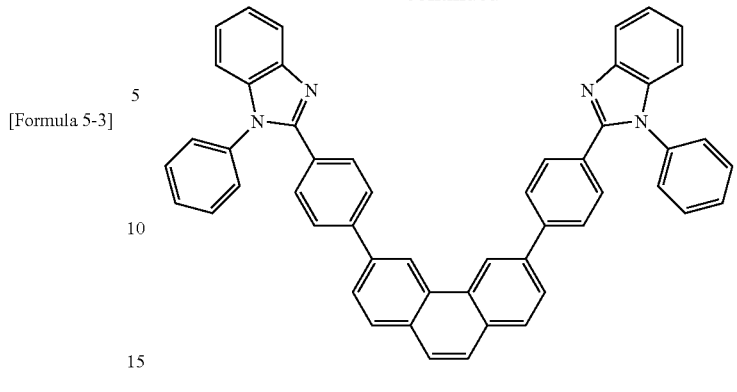
The compound of Formula 5-3 was prepared in the same manner as in Preparation Example 101, except that Compound A-10 was used instead of Compound A-2 in Preparation Example 109. MS: $[M+H]^+=714$
<Preparation Example 110> Preparation of Compound of Formula 3-15
[Formula 3-15]
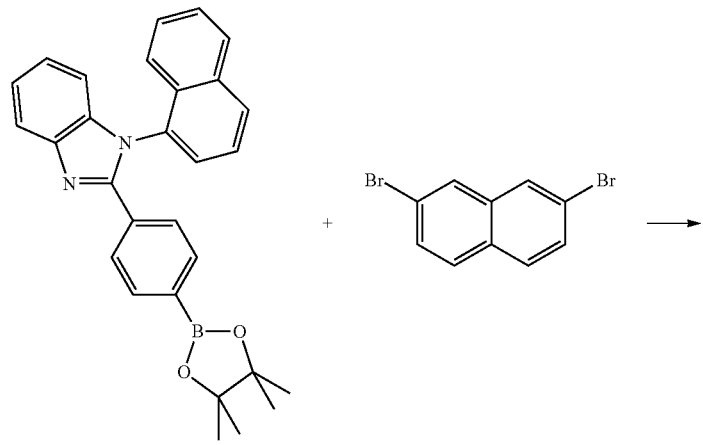
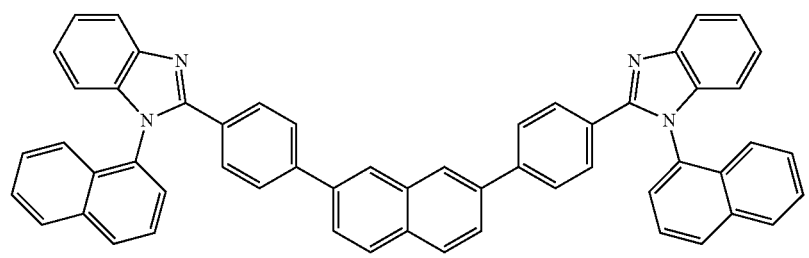

The compound of Formula 3-14 was prepared in the same manner as in Preparation Example 101, except that Compound A-12 was used instead of Compound A-2 in Preparation Example 101. MS: [M+H]$^+$=764

<Preparation Example 111> Preparation of Compound of Formula 6-1

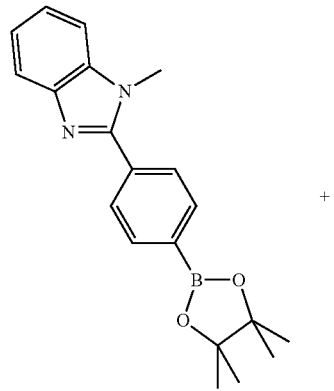

+

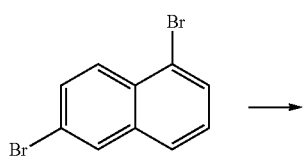

→

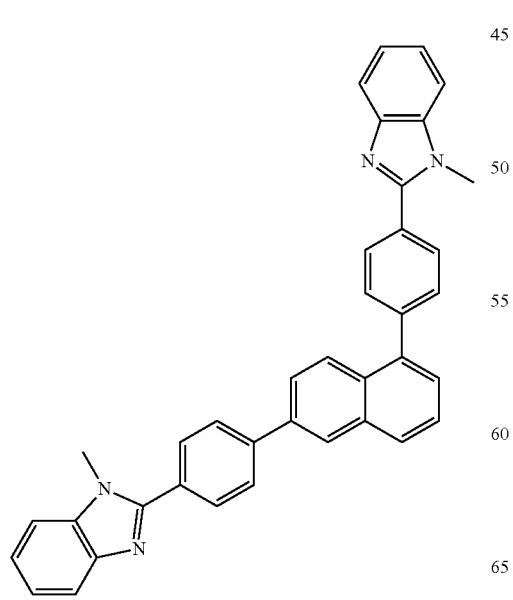

[Formula 6-1]

The compound of Formula 6-1 was prepared in the same manner as in Preparation Example 101, except that the compound 1,6-dibromophenanthrene was used instead of the compound 2,7-dibromonaphthalene in Preparation Example 101. MS: [M+H]$^+$=540

<Preparation Example 112> Preparation of Compound of Formula 7-1

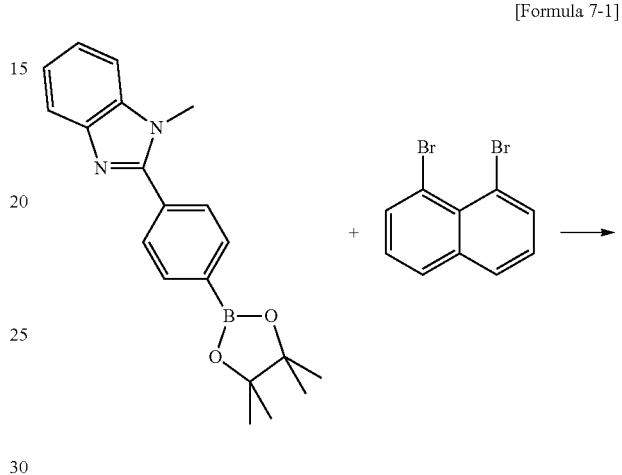

[Formula 7-1]

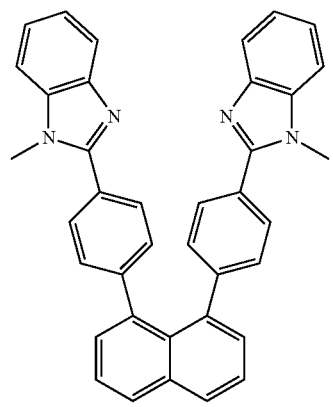

The compound of Formula 7-1 was prepared in the same manner as in Preparation Example 101, except that the compound 1,8-dibromonaphthalene was used instead of the compound 2,7-dibromonaphthalene in Preparation Example 101. MS: [M+H]$^+$=540

<Preparation Example 113> Preparation of Compound of Formula 8-1

<Preparation Example 114> Preparation of Compound of Formula 9-1

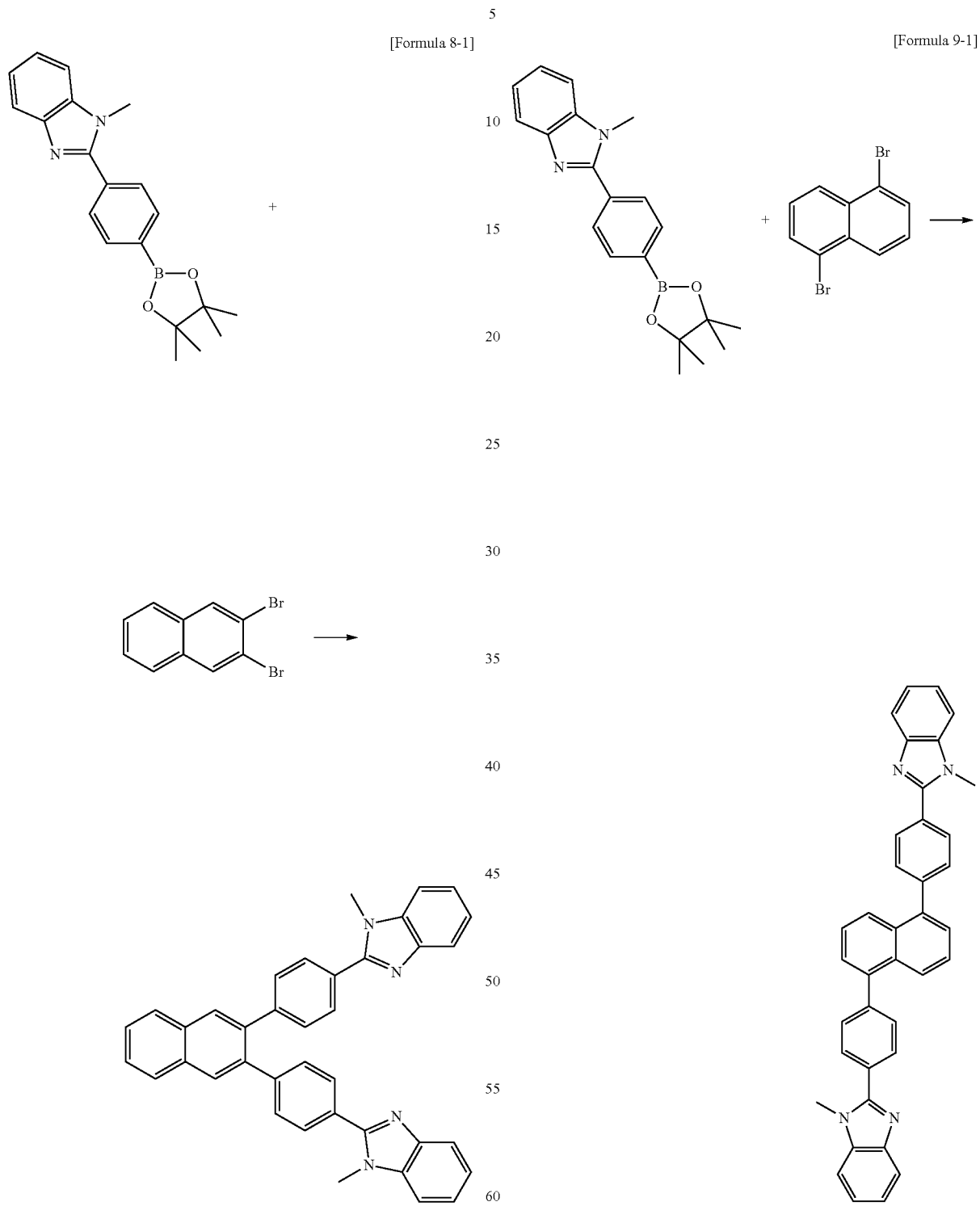

[Formula 8-1]

[Formula 9-1]

The compound of Formula 8-1 was prepared in the same manner as in Preparation Example 101, except that the compound 1,2-dibromonaphthalene was used instead of the compound 2,7-dibromonaphthalene in Preparation Example 101. MS: [M+H]$^+$=540

The compound of Formula 9-1 was prepared in the same manner as in Preparation Example 101, except that the compound 1,5-dibromonaphthalene was used instead of the compound 2,7-dibromonaphthalene in Preparation Example 101. MS: [M+H]$^+$=540

<Preparation Example 115> Preparation of Compound of Formula 10-4

[Formula 10-4]

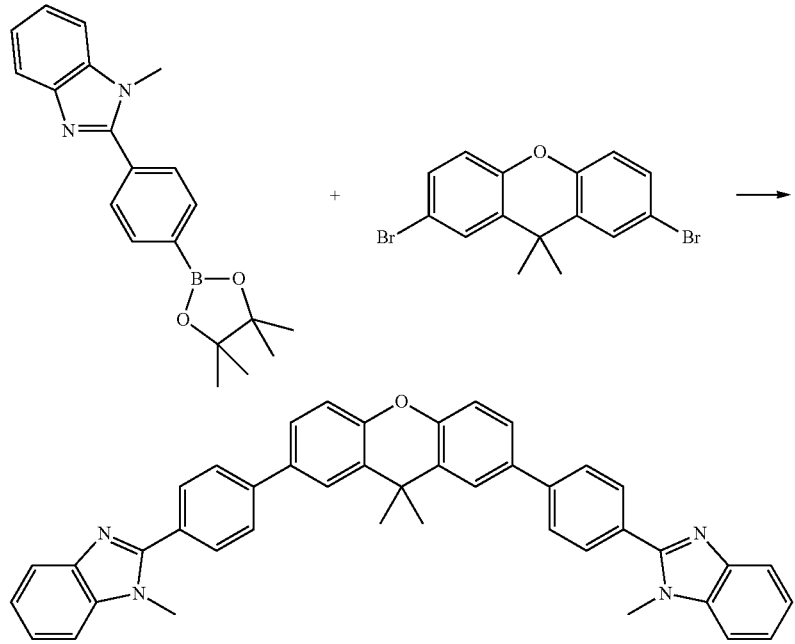

The compound of Formula 10-4 was prepared in the same manner as in Preparation Example 101, except that the compound 2,7-dibromo-9,9-dimethyl-9H-xanthene was used instead of the compound 2,7-dibromonaphthalene in Preparation Example 101. MS: [M+H]$^+$=622

Experimental Example

Experimental Example 1-1-1

A glass substrate on which a thin film of indium tin oxide (ITO) was coated to a thickness of 500 Å was placed into distilled water in which a detergent was dissolved, and washed using ultrasonic waves. At this time, a product manufactured by Fischer Co. was used as the detergent, and distilled water, which had been twice filtered by a filter manufactured by Millipore Co., was used as the distilled water. After the ITO was washed for 30 minutes, ultrasonic washing was repeated twice by using distilled water for 10 minutes. After the washing using distilled water was completed, ultrasonic washing was conducted using a solvent of isopropyl alcohol, acetone, and methanol, and the resultant product was dried and then transported to a plasma washing machine. In addition, the substrate was washed by using an oxygen plasma for 5 minutes, and then was transported to a vacuum deposition machine.

Hexanitrile hexaazatriphenylene (HAT) of the following Formula was vacuum deposited to a thickness of 50 Å by heating, on a transparent ITO electrode, which was thus prepared, so as to form a hole injection layer.

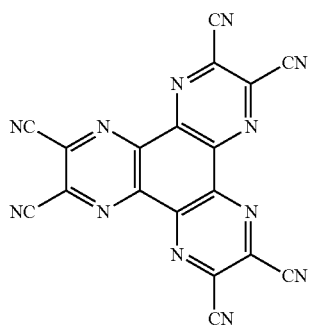

[HAT]

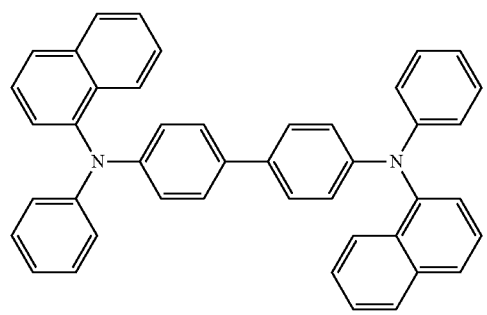

[NPB]

A hole transporting layer was formed by vacuum depositing 4,4'-bis[N-(1-naphthyl)-N-phenylamino]biphenyl (NPB) (1,700 Å) of the above Formula on the hole injection layer.

Subsequently, a light emitting layer was formed by vacuum depositing BH and GD shown below at a weight ratio of 20:1 in a film thickness of 230 Å on the hole transporting layer.

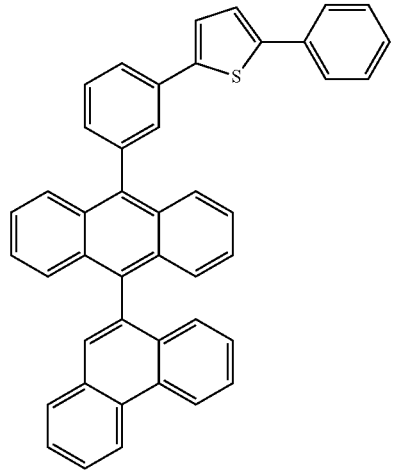

[BH]

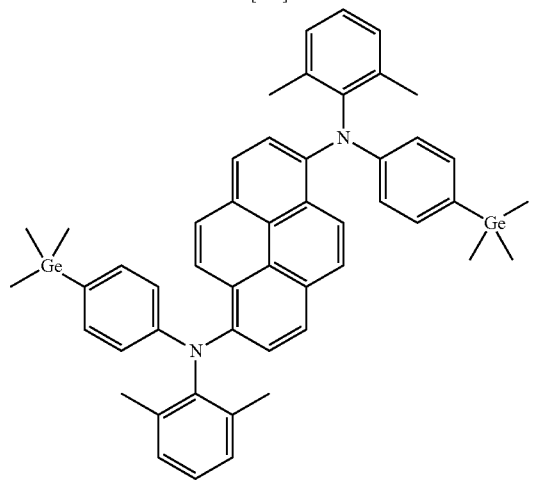

[GD]

The electron injection and transporting layers were formed by vacuum depositing the compound of Formula 3-1, prepared in Preparation Example 101 on the light emitting layer in a thickness of 200 Å.

On the electron injection and transporting layers, lithium fluoride (LiF) in a thickness of 15 Å and aluminum in a thickness of 1,000 Å were sequentially deposited to form a cathode.

In the above process, the deposition rate of the organic material as maintained at 0.4 to 0.7 Å/sec, the deposition rate of lithium fluoride of the cathode was maintained at 0.3 Å/sec, the deposition rate of aluminum was maintained at 2 Å % sec, and the degree of vacuum during the deposition was maintained at $2 \times 10^{-7}$ to $5 \times 10^{-8}$ torr to manufacture an organic light emitting device.

Experimental Example 2-1-1

An organic light emitting device was manufactured in the same manner as in Experimental Example 1-1-1, except that a compound of the following Formula ET-A was used instead of the compound of Formula 3-1 in Experimental Example 1-1-1.

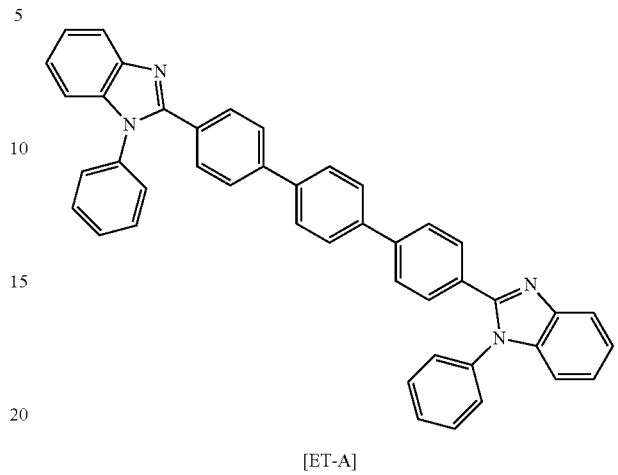

[ET-A]

Experimental Examples 1-1-2 to 1-1-16 and 2-2-1

An organic light emitting device was manufactured in the same manner as in Experimental Example 1-1-1, except that each compound shown in Table 1 was used instead of the compound of Formula 3-1 in Experimental Example 1-1-1. When current (10 mA/cm$^2$) was applied to the organic light emitting devices manufactured by Experimental Examples 1-1-2 to 1-1-16 and 2-2-1, the results shown in Table 1 were obtained.

TABLE 1

| | Compound | Voltage (V) | Efficiency (cd/A) | Color coordinate (x, y) |
|---|---|---|---|---|
| Experimental Example 1-1-1 | 3-1 | 4.02 | 6.90 | (0.137, 0.107) |
| Experimental Example 1-1-2 | 3-2 | 4.07 | 6.98 | (0.138, 0.106) |
| Experimental Example 1-1-3 | 3-3 | 4.32 | 6.35 | (0.136, 0.109) |
| Experimental Example 1-1-4 | 3-4 | 4.23 | 6.52 | (0.137, 0.108) |
| Experimental Example 1-1-5 | 3-13 | 4.11 | 6.83 | (0.137, 0.106) |
| Experimental Example 1-1-6 | 3-14 | 5.07 | 5.66 | (0.138, 0.107) |
| Experimental Example 1-1-7 | 4-1 | 4.05 | 6.87 | (0.137, 0.108) |
| Experimental Example 1-1-8 | 5-2 | 4.09 | 6.88 | (0.137, 0.106) |
| Experimental Example 1-1-9 | 5-3 | 4.73 | 6.12 | (0.136, 0.107) |
| Experimental Example 1-1-10 | 3-15 | 4.79 | 5.92 | (0.136, 0.107) |
| Experimental Example 1-1-12 | 6-1 | 4.09 | 6.87 | (0.137, 0.108) |
| Experimental Example 1-1-13 | 7-1 | 4.05 | 6.92 | (0.136, 0.107) |
| Experimental Example 1-1-14 | 8-1 | 4.19 | 6.88 | (0.136, 0.108) |
| Experimental Example 1-1-15 | 9-1 | 4.28 | 6.81 | (0.137, 0.108) |
| Experimental Example 1-1-16 | 10-4 | 4.12 | 6.91 | (0.138, 0.106) |
| Experimental Example 2-1-1 | ET-A | 5.89 | 4.86 | (0.137, 0.107) |

In the case of a device manufactured by using the compound represented by Formula 1 of the present invention, it can be confirmed that the device exhibited a high current efficiency and a low driving voltage, and this is because the compound of Formula 1 in the device serves an excellent role in electron transport along with electron injection.

Experimental Example 3-1-1

A glass substrate on which a thin film of indium tin oxide (ITO) was coated to a thickness of 500 Å was placed into distilled water in which a detergent was dissolved, and washed using ultrasonic waves. At this time, a product manufactured by Fischer Co. was used as the detergent, and distilled water, which had been twice filtered by a filter manufactured by Millipore Co., was used as the distilled water. After the ITO was washed for 30 minutes, ultrasonic washing was repeated twice by using distilled water for 10 minutes. After the washing using distilled water was completed, ultrasonic washing was conducted using a solvent of isopropyl alcohol, acetone, and methanol, and the resultant product was dried and then transported to a plasma washing machine. Furthermore, the substrate was washed by using an oxygen plasma for 5 minutes, and then was transported to a vacuum deposition machine.

Hexanitrile hexaazatriphenylene (HAT) of the following Formula was vacuum deposited to a thickness of 50 Å by heating, on a transparent ITO electrode, which was thus prepared, so as to form a hole injection layer.

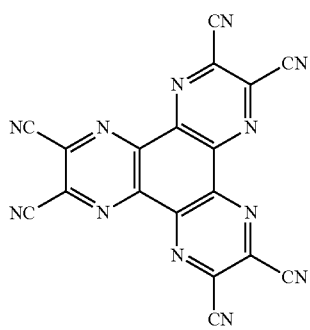

[HAT]

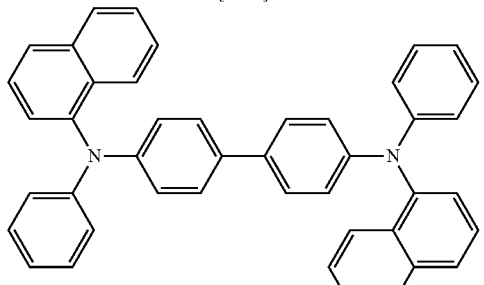

[NPB]

A hole transporting layer was formed by vacuum depositing 4,4'-bis[N-(1-naphthyl)-N-phenylamino]biphenyl (NPB) (1,700 Å) of the above Formula on the hole injection layer.

Subsequently, a light emitting layer was formed by vacuum depositing BH and GD shown below at a weight ratio of 20:1 in a film thickness of 230 Å on the hole transporting layer.

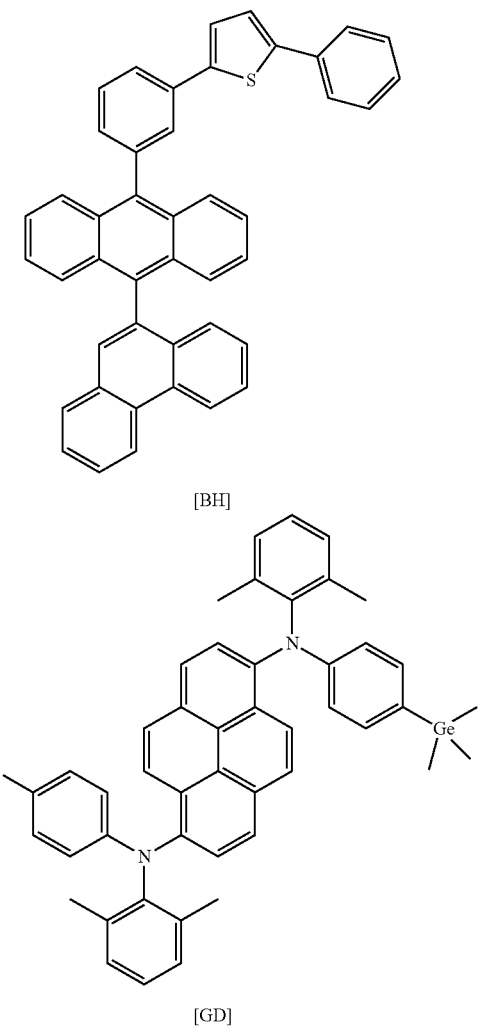

[BH]

[GD]

The electron injection and transporting layers were formed by vacuum depositing HBL shown below in a thickness of 100 Å on the light emitting layer, and then vacuum depositing the compound of Formula 3-1 prepared in Preparation Example 101 and lithium at a weight ratio of 100:1 in a thickness of 100 Å.

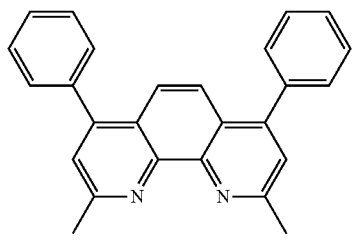

[HBL]

On the electron injection and transporting layers, aluminum was deposited in a thickness of 1,000 Å to form a cathode.

In the above process, the deposition rate of the organic material was maintained at 0.4 to 0.7 Å/sec, the deposition rate of aluminum of the cathode was maintained at 2 Å/sec, and the degree of vacuum during the deposition was maintained at $2\times10^{-7}$ to $5\times10^{-8}$ torr to manufacture an organic light emitting device.

Experimental Examples 3-1-2 to 3-1-5

An organic light emitting device was manufactured in the same manner as in Experimental Example 3-1-1, except that each compound shown in Table 2 was used instead of the compound of Formula 3-1 in Experimental Example 3-1-1.

Experimental Example 4-1-1

An organic light emitting device was manufactured in the same manner as in Experimental Example 3-1-1, except that a compound of ET-A was used instead of the compound of Formula 3-1 in Experimental Example 3-1-1.

When current (10 mA/cm$^2$) was applied to the organic light emitting devices manufactured by Experimental Examples 3-1-1 to 3-1-5 and 4-1-1, the results shown in Table 2 were obtained.

TABLE 2

| | Compound | Voltage (V) | Efficiency (cd/A) | Color coordinate (x, y) |
|---|---|---|---|---|
| Experimental Example 3-1-1 | 3-1 | 3.89 | 7.12 | (0.137, 0.107) |
| Experimental Example 3-1-2 | 4-1 | 3.97 | 7.15 | (0.137, 0.108) |
| Experimental Example 3-1-3 | 6-1 | 4.01 | 7.02 | (0.137, 0.108) |
| Experimental Example 3-1-4 | 7-1 | 3.95 | 7.05 | (0.136, 0.107) |
| Experimental Example 3-1-5 | 10-4 | 4.02 | 6.99 | (0.138, 0.106) |
| Experimental Example 4-1-1 | ET-A | 5.56 | 4.99 | (0.137, 0.107) |

The invention claimed is:

1. A nitrogen-containing heterocyclic compound represented by the following Formula 1:

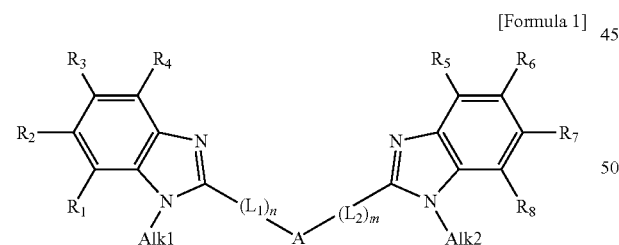

[Formula 1]

in Formula 1, $R_1$ to $R_8$ are the same as or different from each other, and are each independently hydrogen; deuterium; a halogen group; a nitrile group; a nitro group; a hydroxy group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted alkylamine group; a substituted or unsubstituted aralkylamine group; a substituted or unsubstituted arylamine group; a substituted or unsubstituted heteroarylamine group; a substituted or unsubstituted aryl group; a substituted or unsubstituted fluorenyl group; a substituted or unsubstituted carbazole group; or a substituted or unsubstituted heterocyclic group comprising one or more of N, O, and S atoms, or two or more adjacent groups of $R_1$ to $R_8$ form a monocyclic or polycyclic ring, Alk1 and Alk2 are the same as or different from each other, and are each independently a substituted or unsubstituted alkyl group; or a substituted or unsubstituted cycloalkyl group;

$L_1$ and $L_2$ are the same as or different from each other, and are each independently oxygen; sulfur; substituted or unsubstituted phosphorus; a substituted or unsubstituted arylene group; a substituted or unsubstituted fluorenylene group; a substituted or unsubstituted carbazolylene group; or a substituted or unsubstituted heteroarylene group comprising one or more of N, O, and S atoms, n is an integer from 1 to 3, m is an integer from 1 to 3, and when n and m are each present as two or more, the substituents in the parenthesis are each independently the same as or different from each other, A is selected from the following structures,

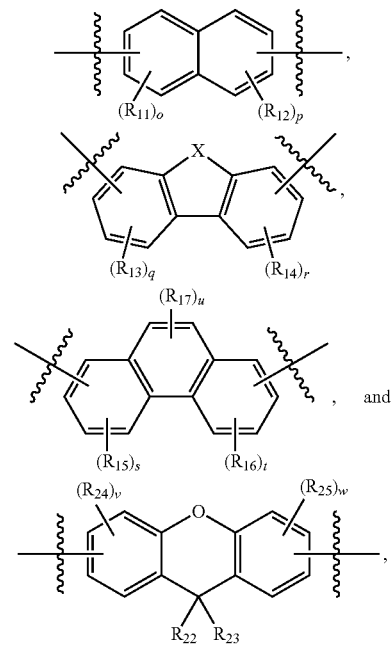

o, p, q, r, s, t, v, and w are each an integer from 0 to 3, and u is an integer from 0 to 2, X is —O—, —S—, or —C($R_{20}$)($R_{21}$)—, $R_{11}$ to $R_{17}$, $R_{20}$, $R_{21}$, $R_{24}$, and $R_{25}$ are the same as or different from each other, and are each independently hydrogen; deuterium; a halogen group; a nitrile group; a nitro group; a hydroxy group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted alkylamine group; a substituted or unsubstituted aralkylamine group; a substituted or unsubstituted arylamine group; a substituted or unsubstituted heteroarylamine group; a substituted or unsubstituted aryl group; a substituted or unsubstituted fluorenyl group; a substituted or unsubstituted carbazole group; or a substituted or unsubstituted heterocyclic group comprising one or more of N, O, and S atoms, and $R_{22}$ and $R_{23}$ are the same as or different from each other, and are each independently hydrogen; or a substituted or unsubstituted alkyl group.

2. The nitrogen-containing heterocyclic compound of claim 1, wherein A is represented by a group selected from the following Formulas:

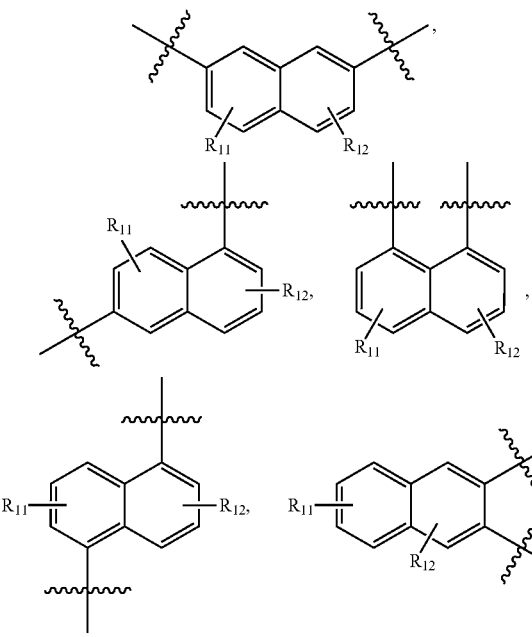

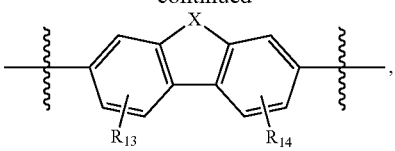

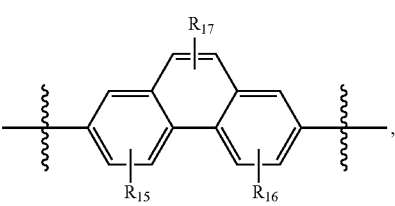

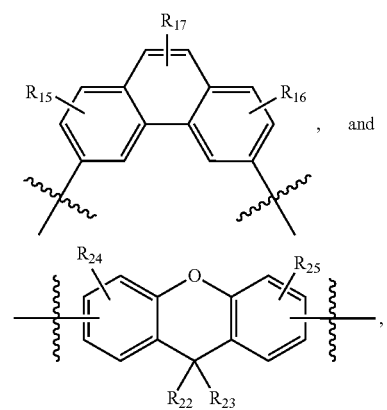

in the formulas, $R_{11}$ to $R_{17}$ and $R_{22}$ to $R_{25}$ are the same as those defined in claim 1.

3. The nitrogen-containing heterocyclic compound of claim 1, wherein Formula 1 comprises a compound represented by any one of the following Formulas 1-1 to 1-5:

[Formula 1-1]

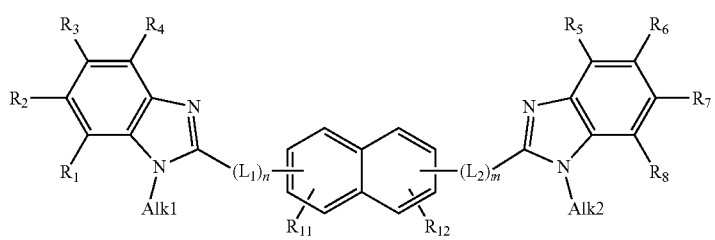

[Formula 1-2]

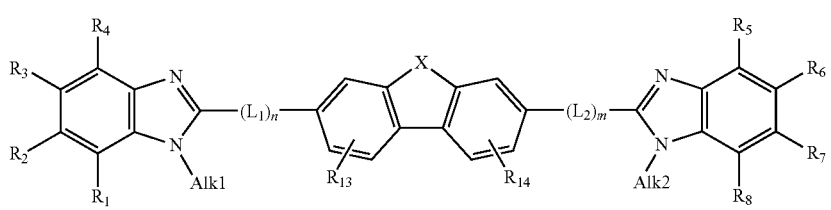

[Formula 1-3]
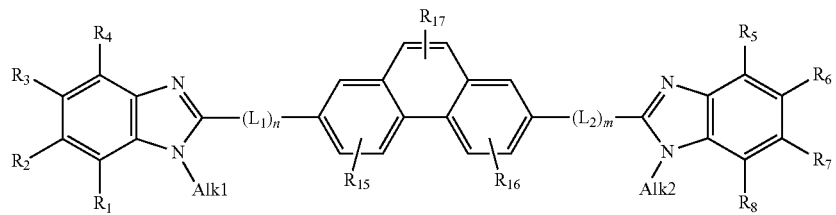
[Formula 1-4]
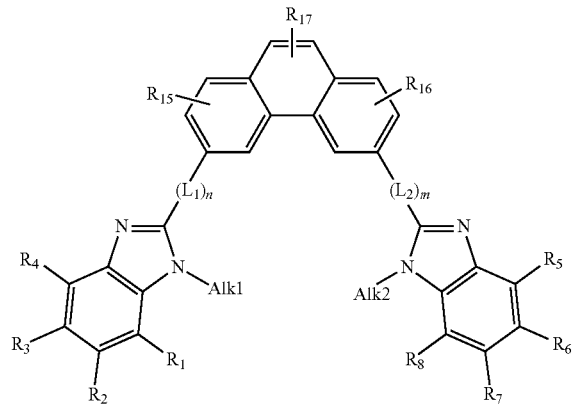
[Formula 1-5]
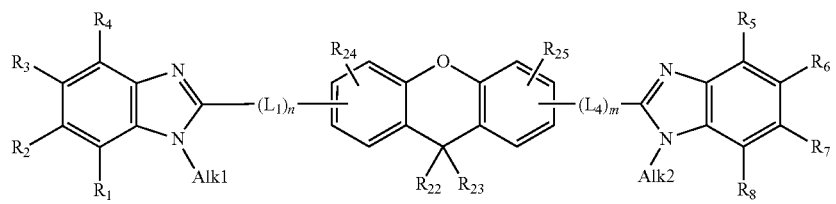
in Formulas 1-1 to 1-5,
$R_1$ to $R_8$, $R_{11}$ to $R_{17}$, $R_{22}$ to $R_{25}$, $L_1$, $L_2$, Alk1, Alk2, n, m, and X are the same as those defined in claim 1.
4. The nitrogen-containing heterocyclic compound of claim 1, wherein the nitrogen-containing heterocyclic compound represented by Formula 1 is selected from the following compounds:
[Formula 3-1]
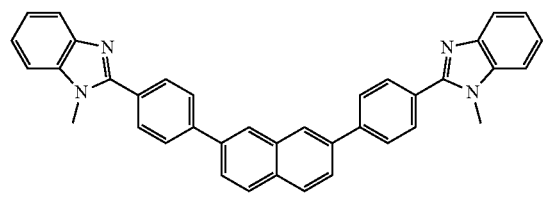
[Formula 3-2]
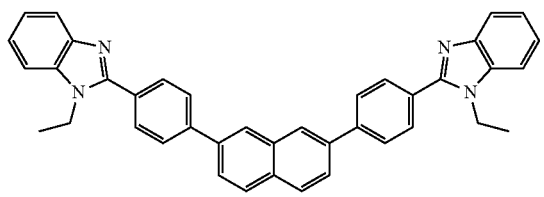
[Formula 3-3]
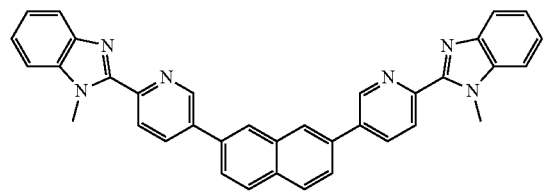
[Formula 3-4]
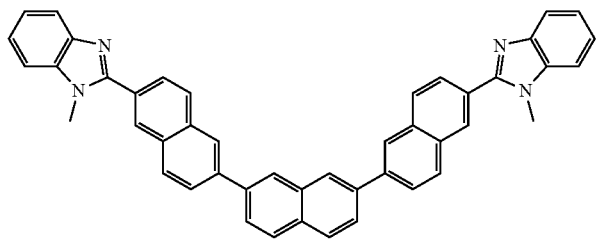

-continued
[Formula 3-5]
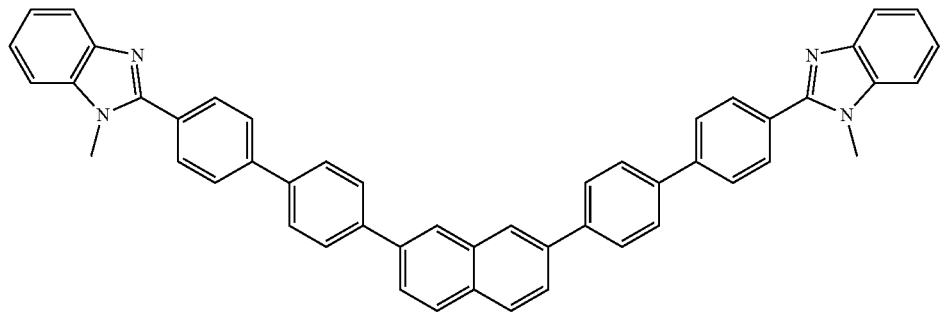
[Formula 3-6]
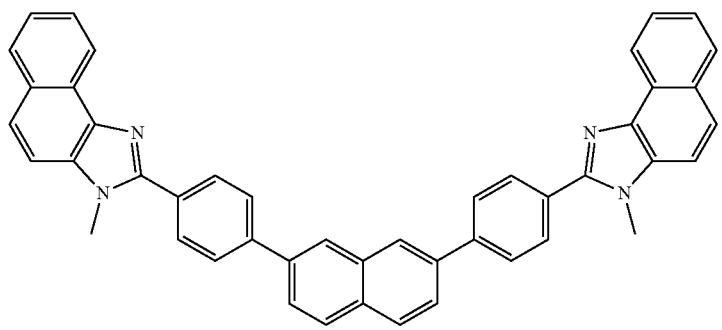
[Formula 3-7]
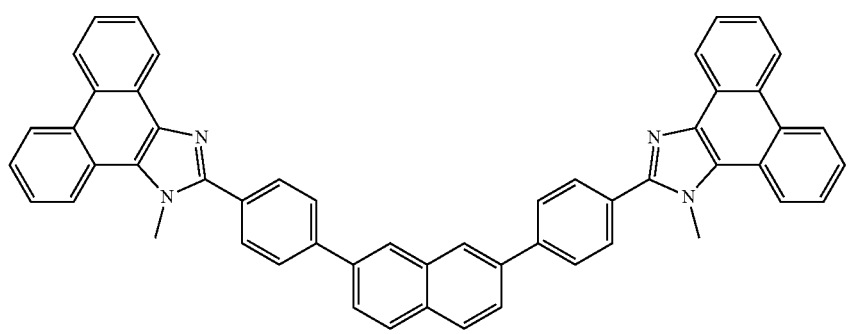
[Formula 3-8]
[Formula 3-9]
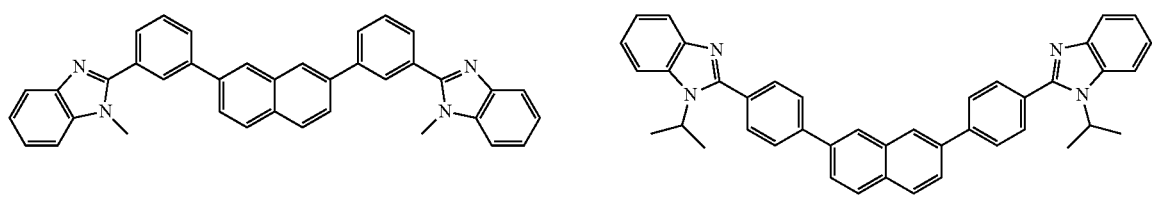
[Formula 3-10]
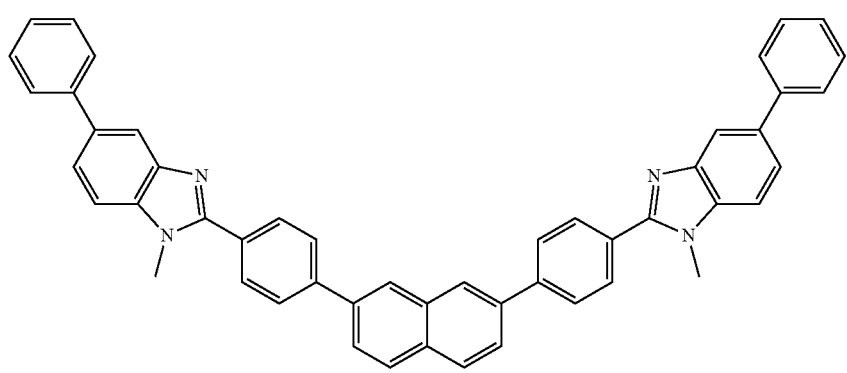

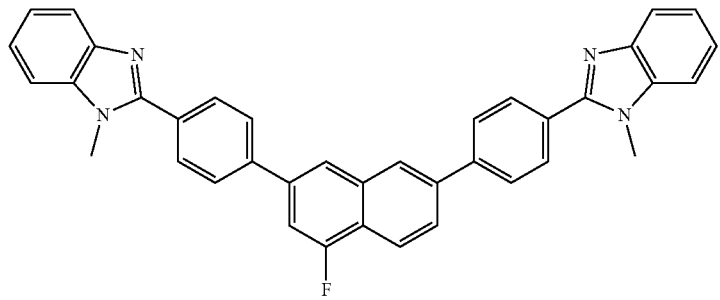
[Formula 3-11]
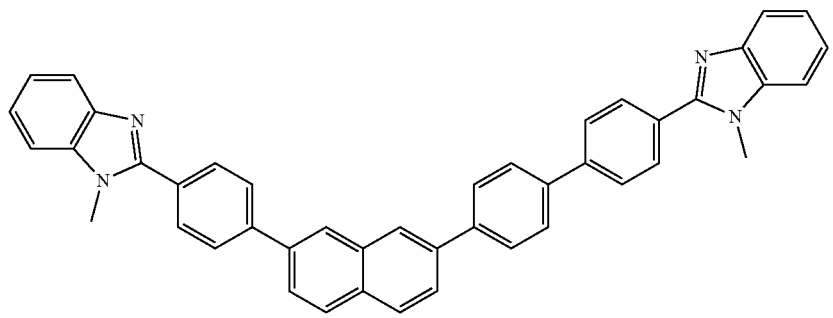
[Formula 3-12]
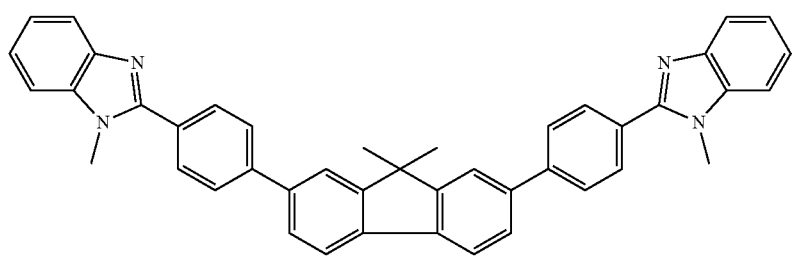
[Formula 4-1]
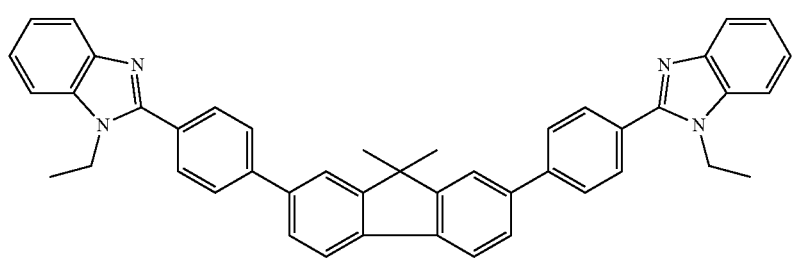
[Formula 4-2]
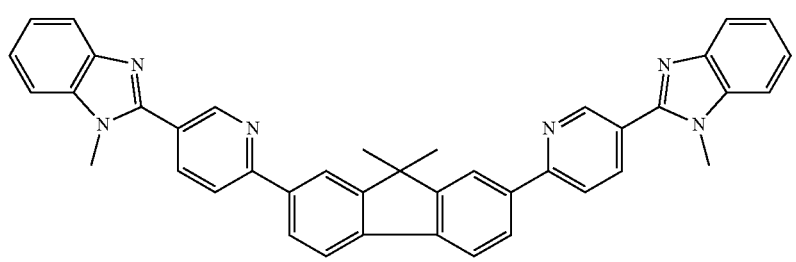
[Formula 4-3]
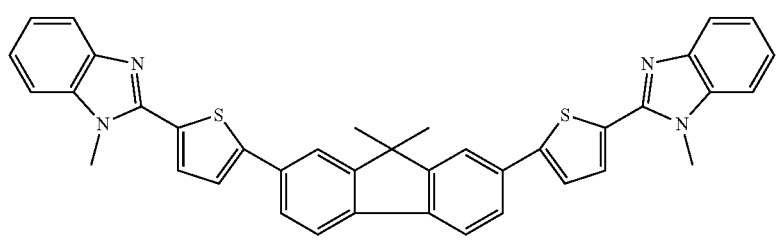
[Formula 4-4]

-continued
[Formula 4-5]
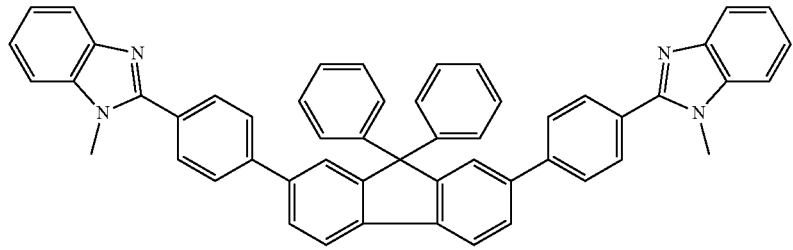
[Formula 4-6]
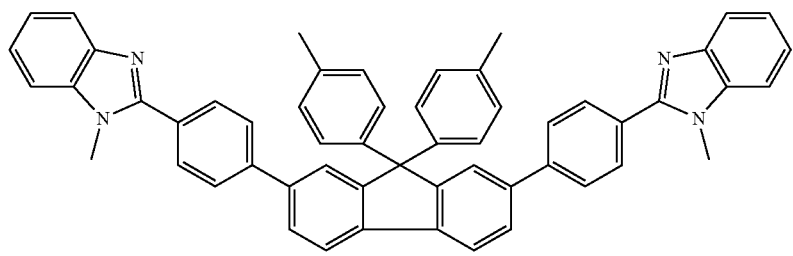
[Formula 4-7]
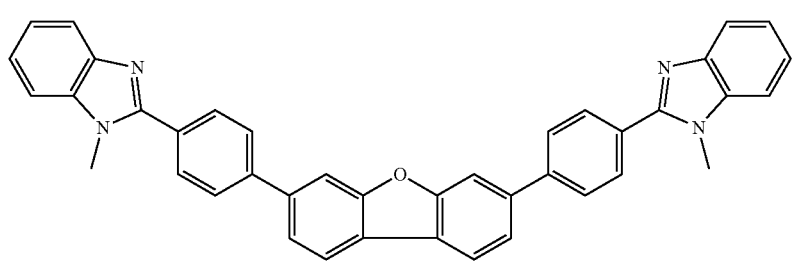
[Formula 4-8]
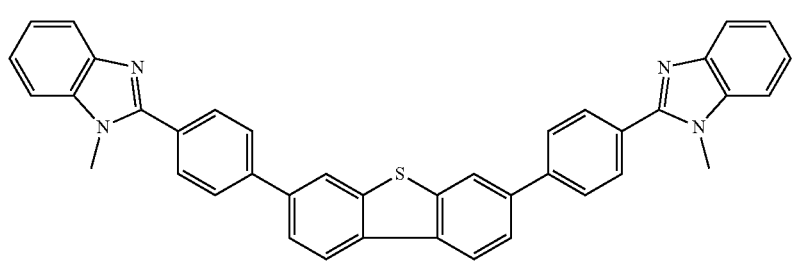
[Formula 4-10]
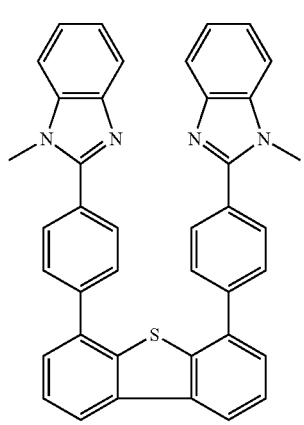

-continued
[Formula 4-11]
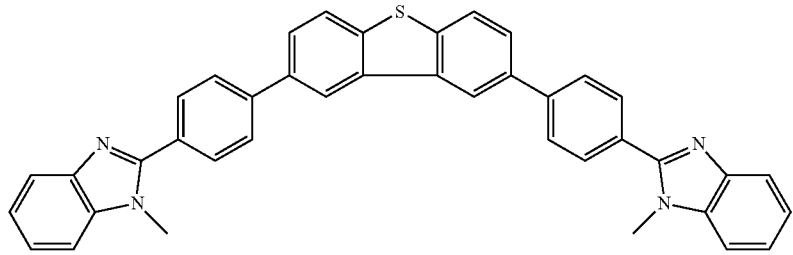
[Formula 4-12]
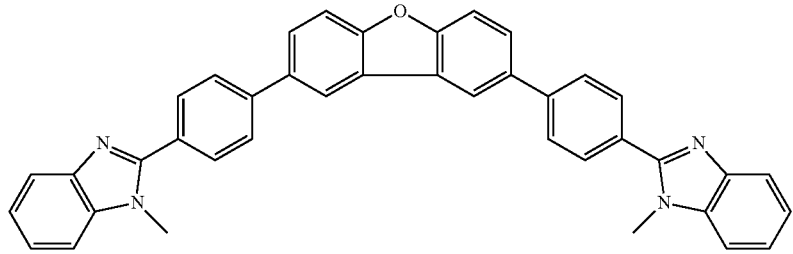
[Formula 4-13]
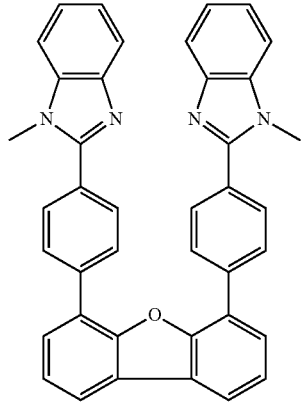
[Formula 5-1]
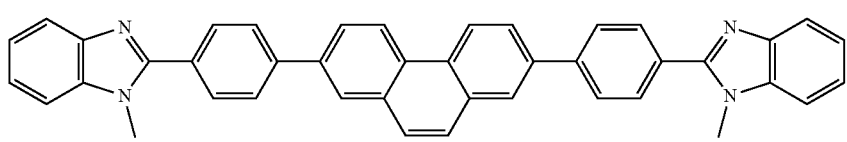
[Formula 5-2]
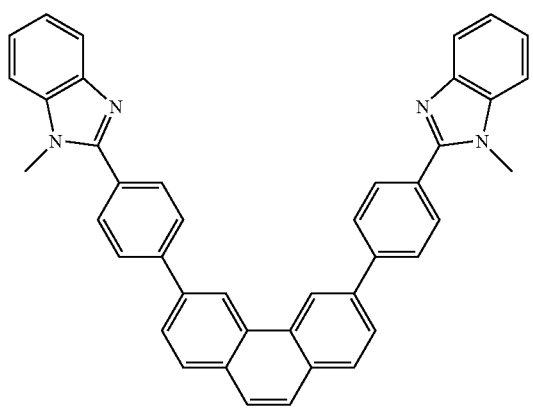
[Formula 6-1]
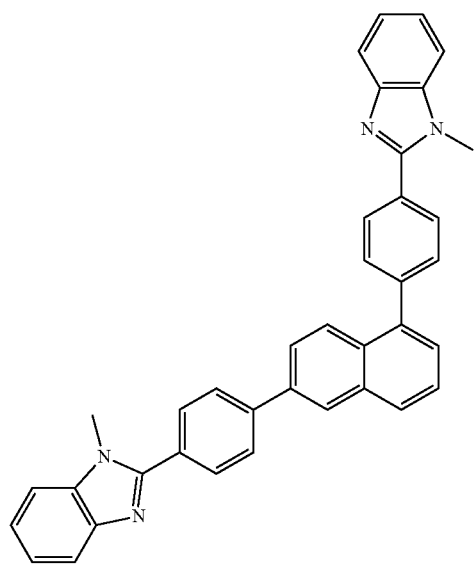

[Formula 6-3]
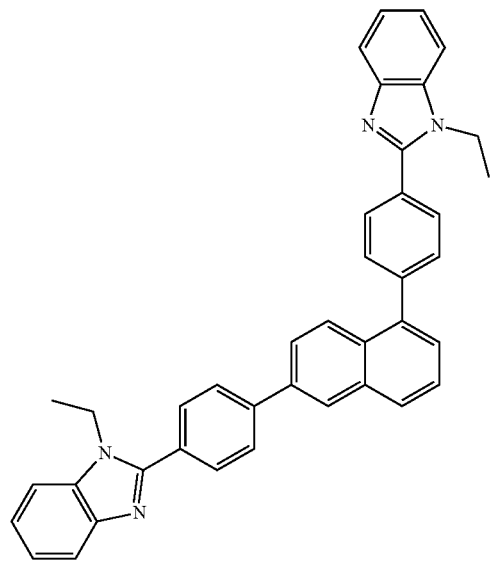
[Formula 6-4]
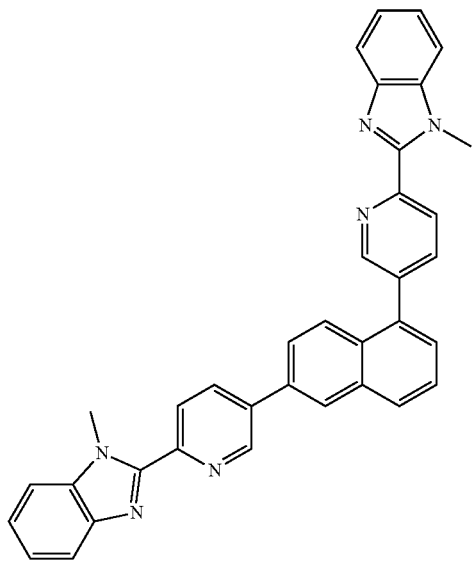
[Formula 6-5]
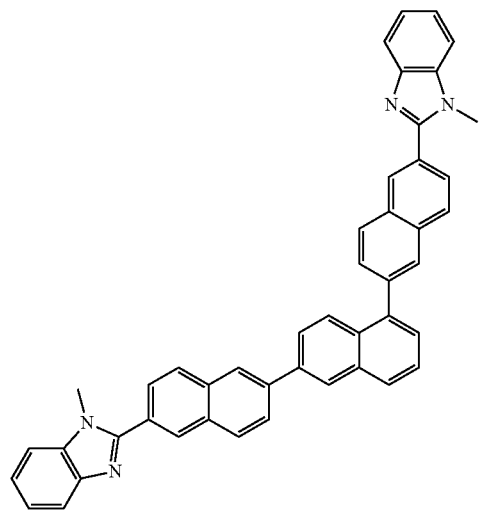
[Formula 6-6]
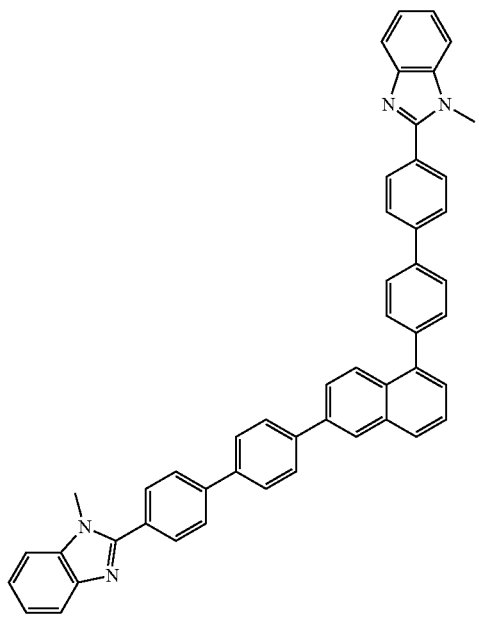

[Formula 6-7]
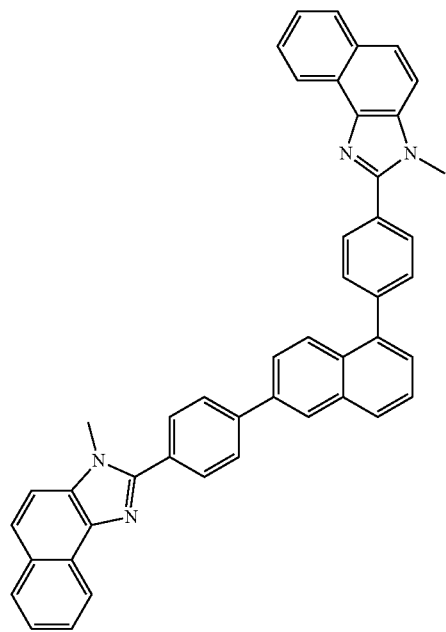
[Formula 6-8]
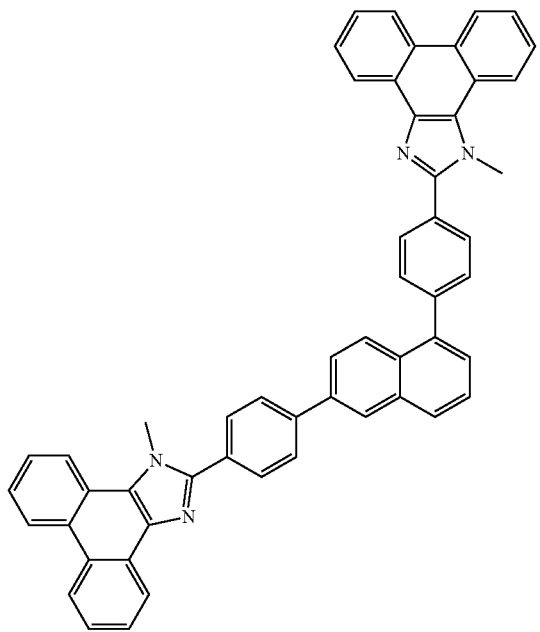
[Formula 6-9]
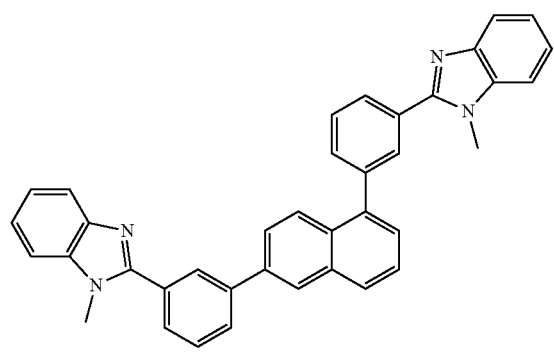
[Formula 6-10]
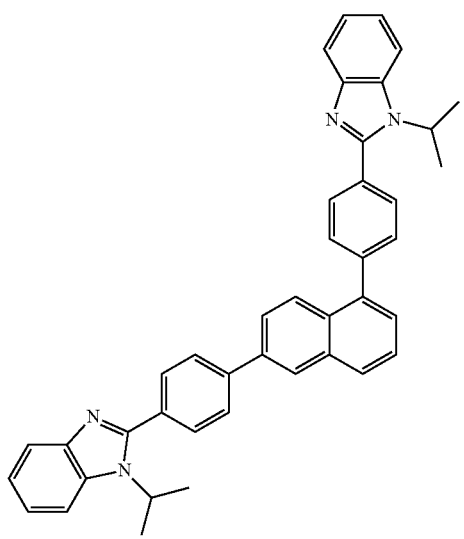

-continued
[Formula 6-11]
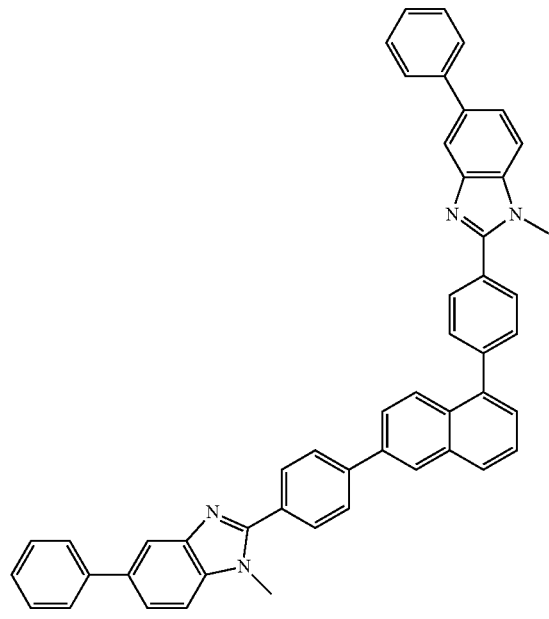
[Formula 6-12]
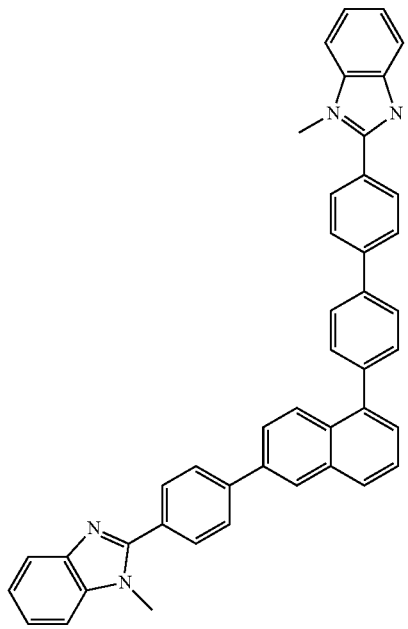
[Formula 7-1]
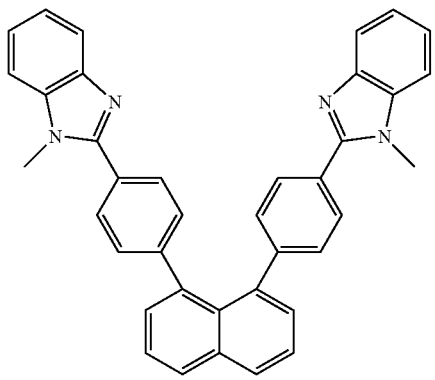
[Formula 7-3]
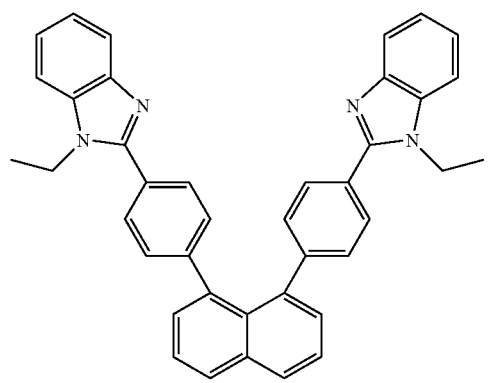
[Formula 7-4]
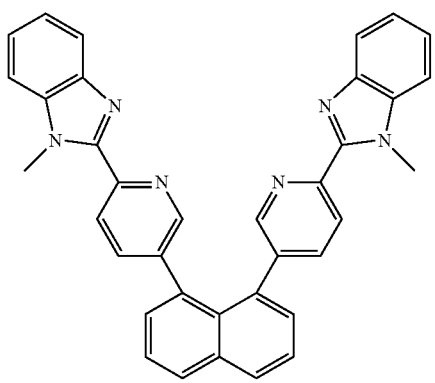

[Formula 7-5]
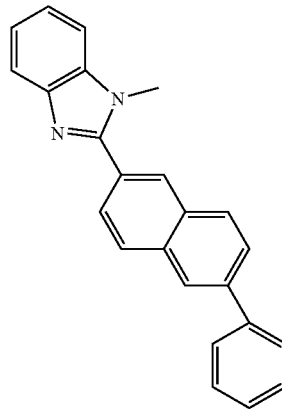
[Formula 7-6]
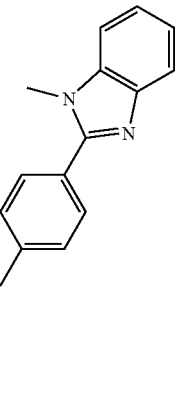
[Formula 7-7]
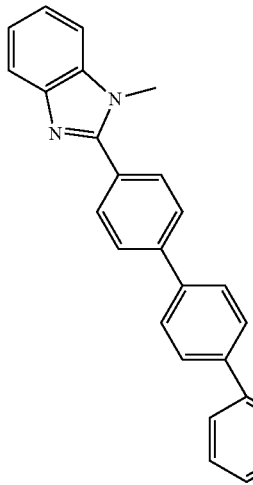
[Formula 7-8]
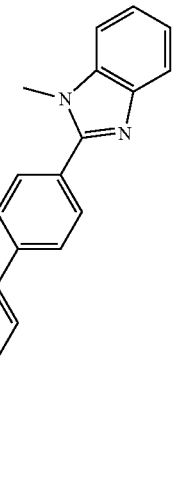
[Formula 7-9]
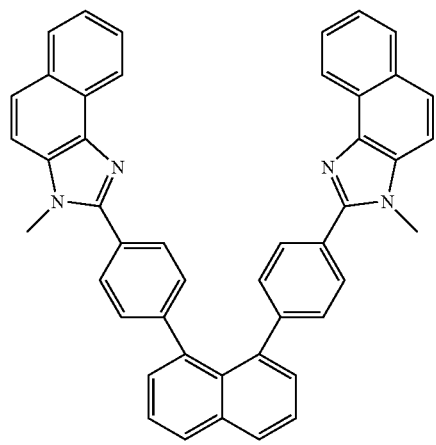
[Formula 7-10]
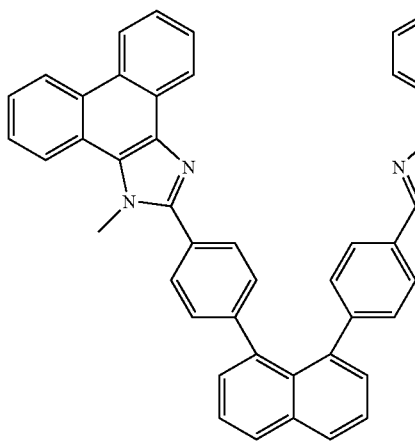

-continued
[Formula 7-11]
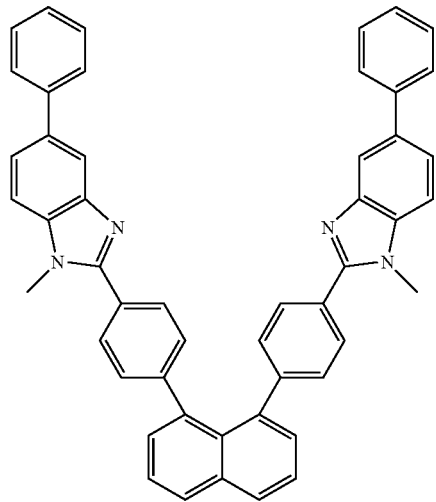
[Formula 7-12]
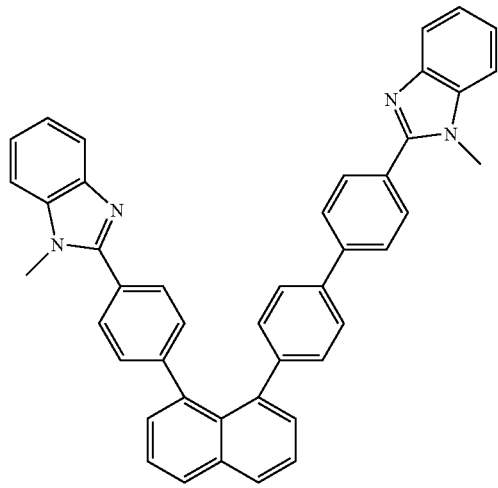
[Formula 8-1]
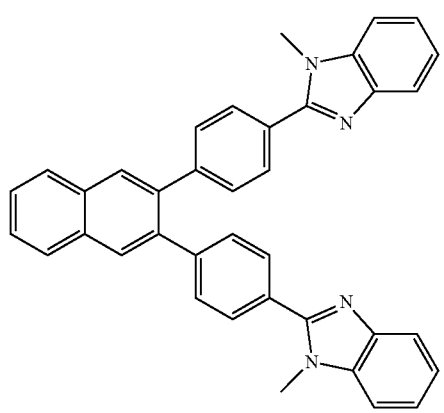
[Formula 8-3]
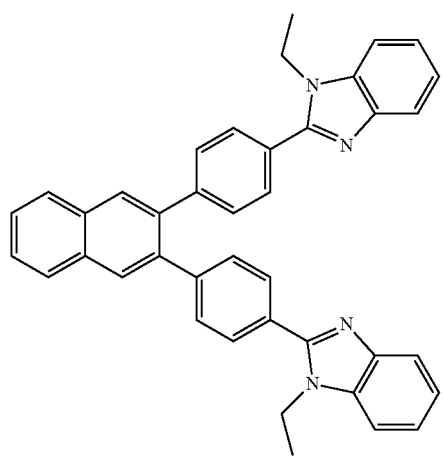
[Formula 8-4]
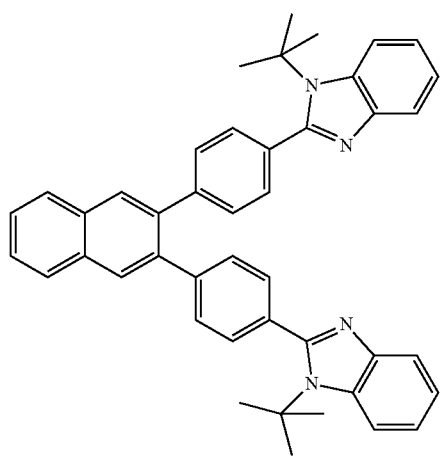

-continued
[Formula 8-6]
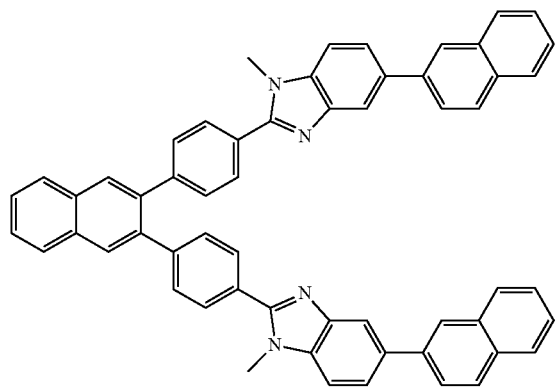
[Formula 8-7]
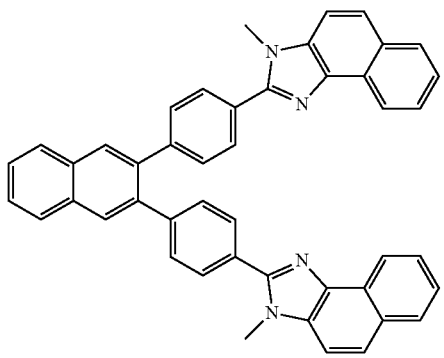
[Formula 8-8]
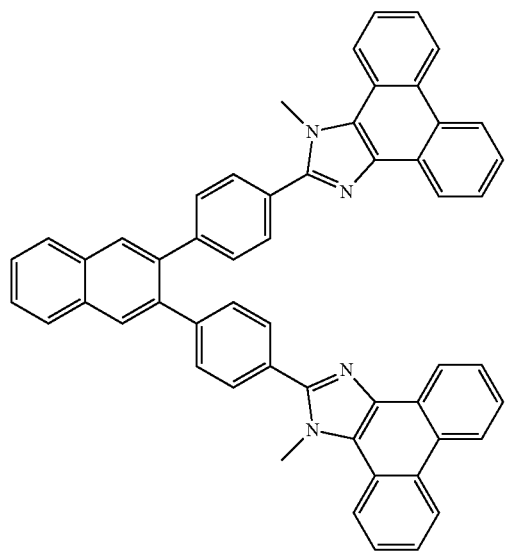
[Formula 8-9]
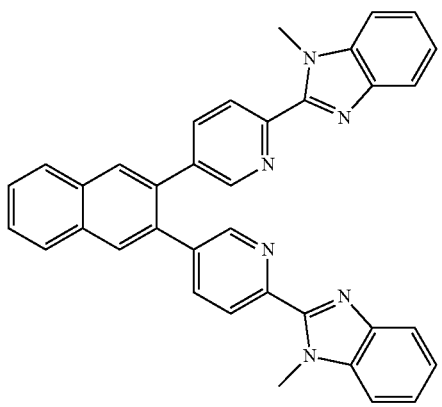
[Formula 8-10]
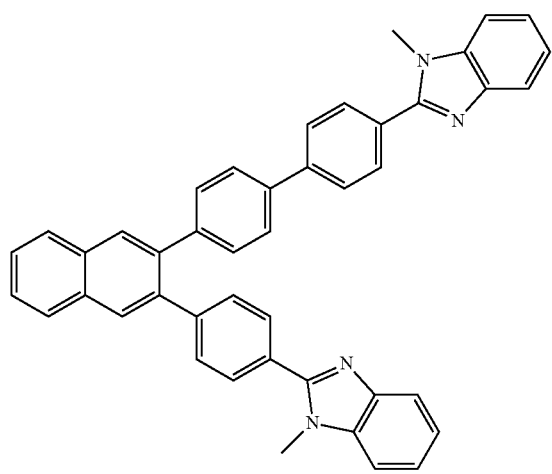
[Formula 8-11]
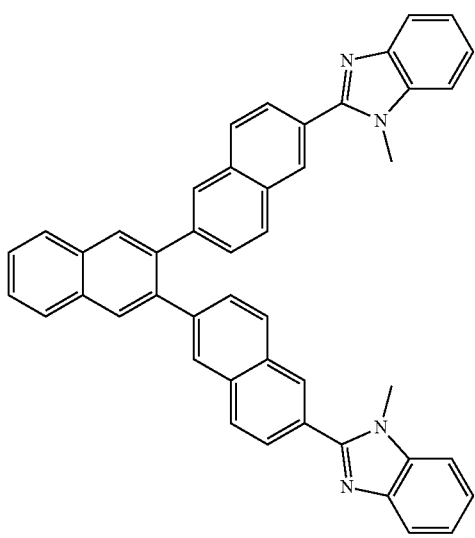

[Formula 8-13]
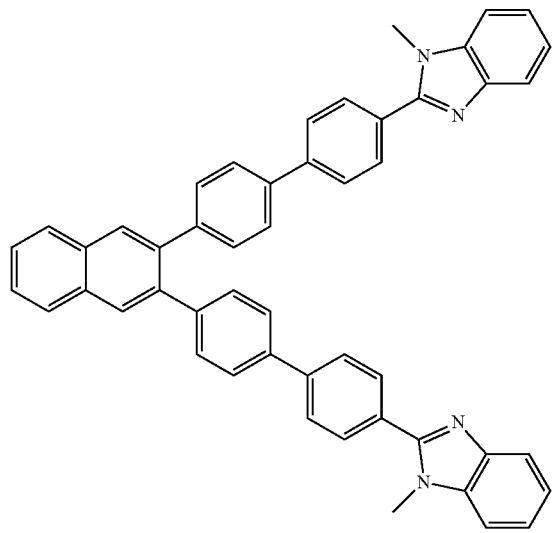
[Formula 8-14]
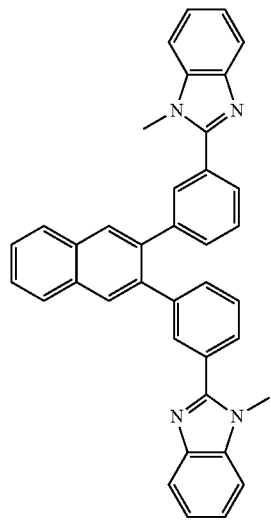
[Formula 9-1]
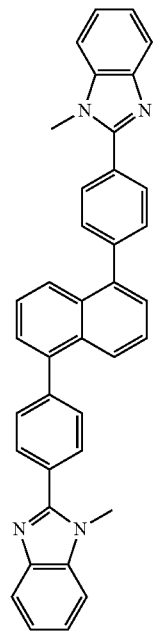

[Formula 9-3]
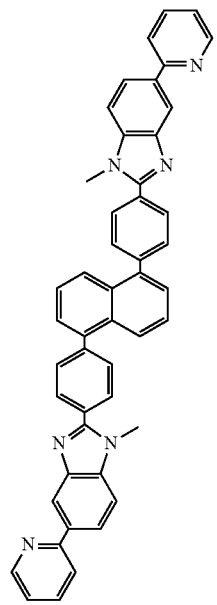
[Formula 9-4]
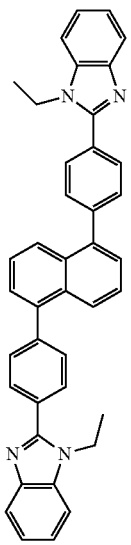
[Formula 9-5]
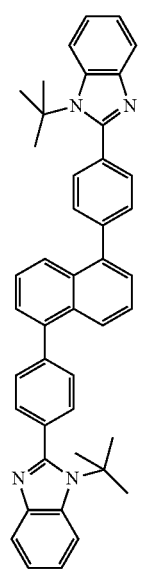
[Formula 9-7]
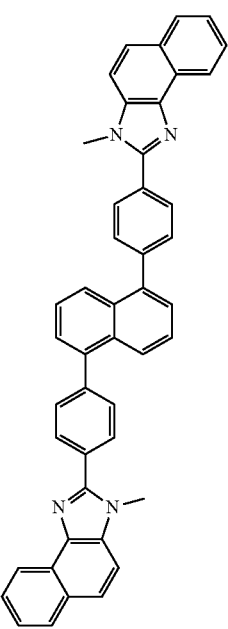

-continued
[Formula 9-8]
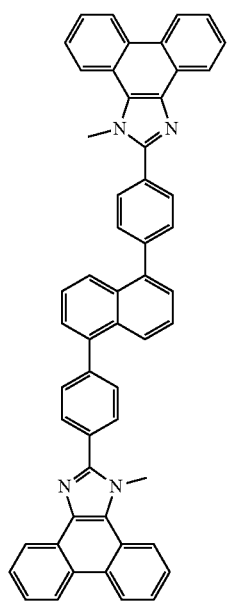
[Formula 9-9]
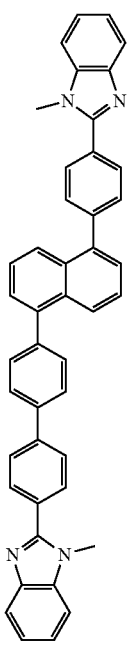
[Formula 9-10]
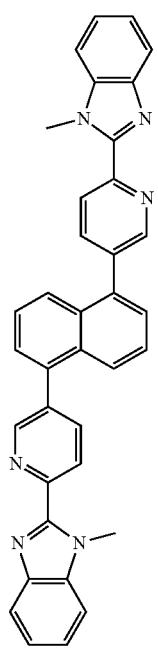
[Formula 9-11]
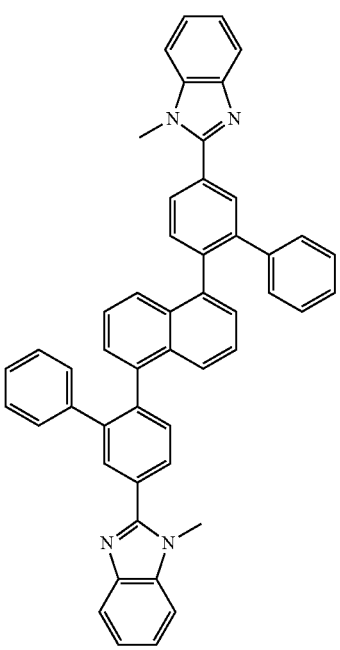

-continued
[Formula 9-13]
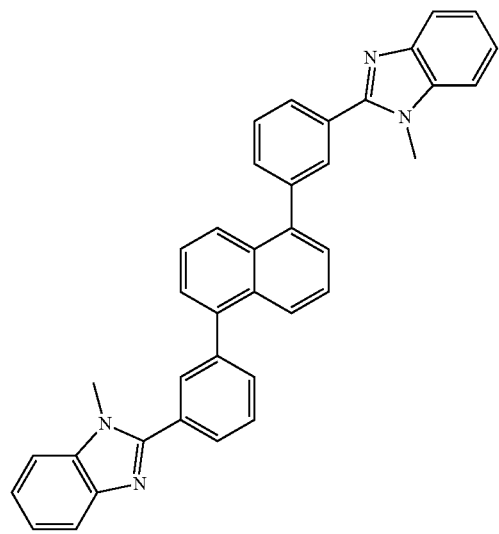
[Formula 10-1]
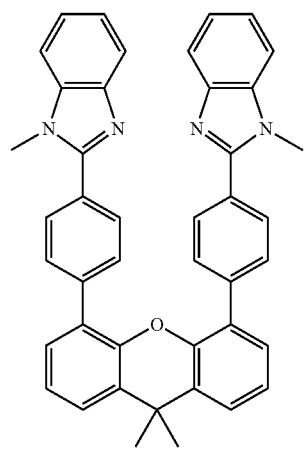
[Formula 10-3]
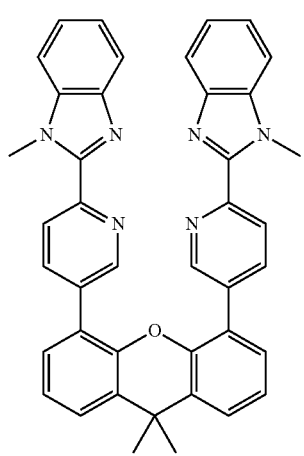

-continued
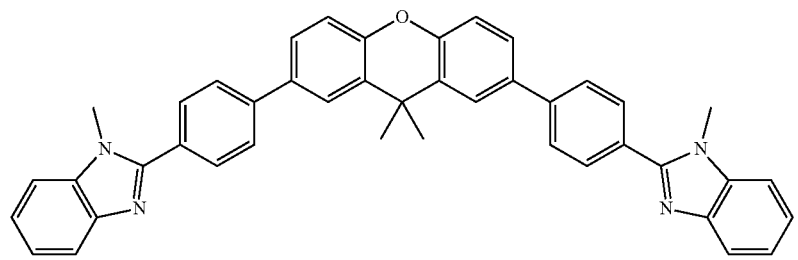
[Formula 10-4]
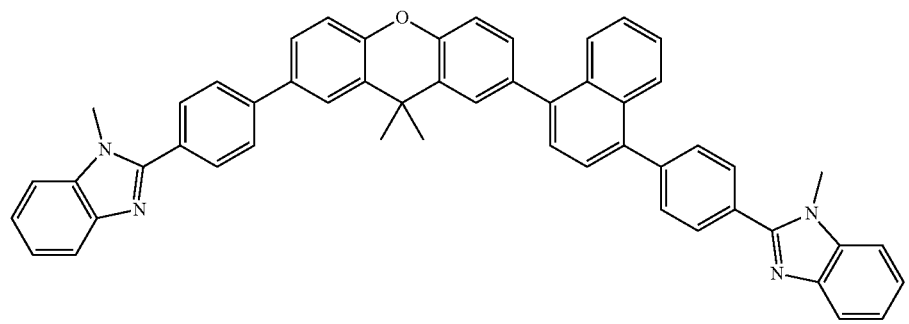
[Formula 10-6]
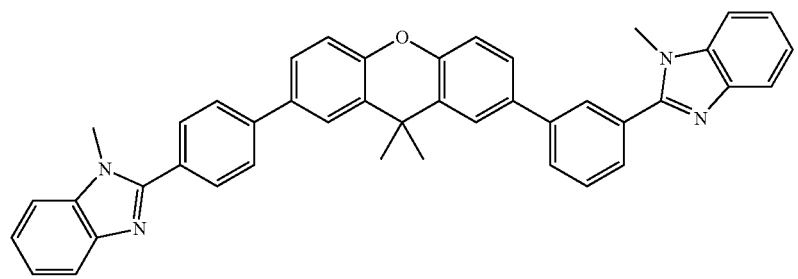
[Formula 10-7]
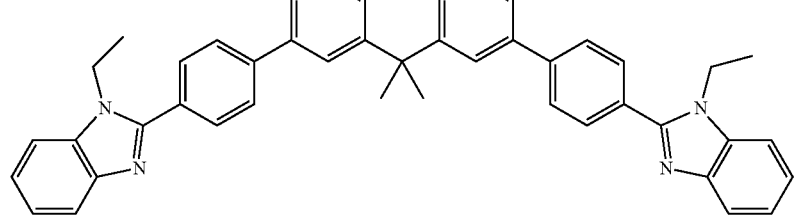
[Formula 10-8]
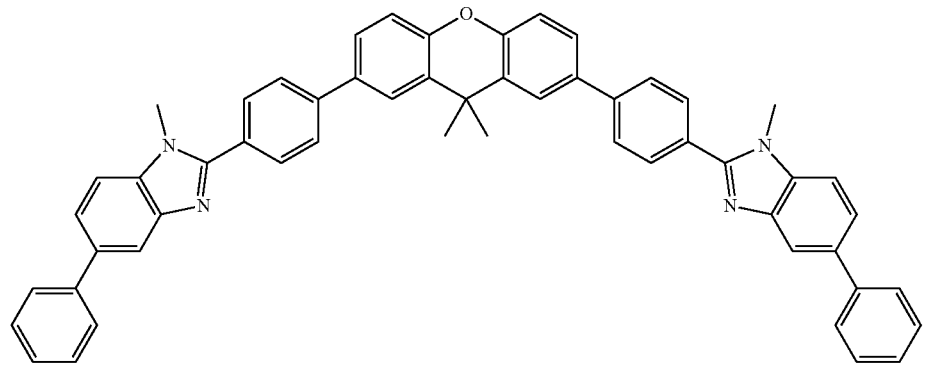
[Formula 10-9]

[Formula 10-10]

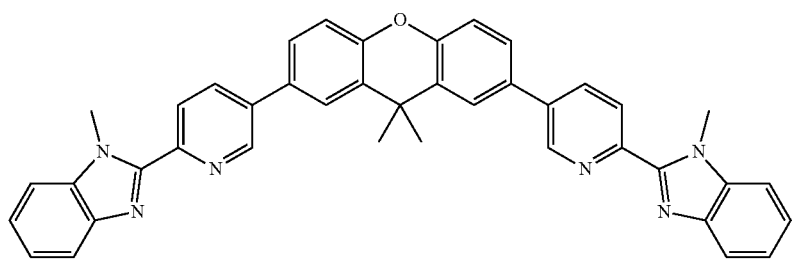

[Formula 10-11]

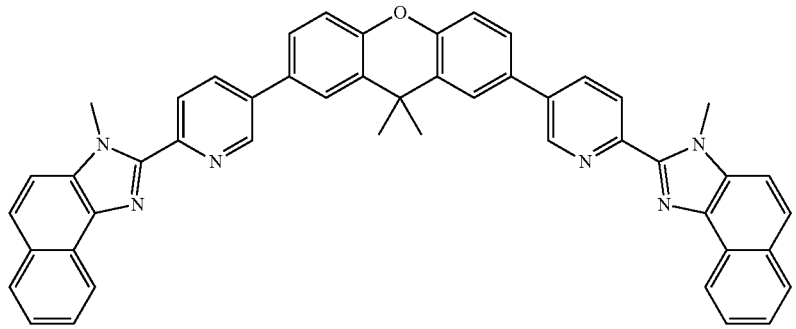

[Formula 10-13]

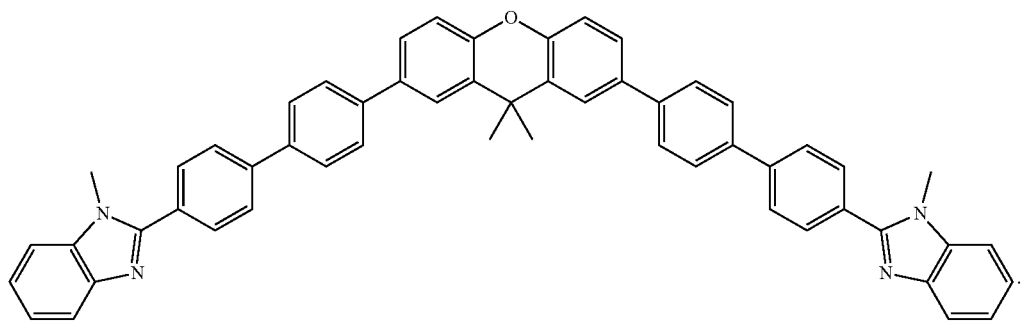

5. A nitrogen-containing heterocyclic compound represented by the following Formula 2:

[Formula 2]

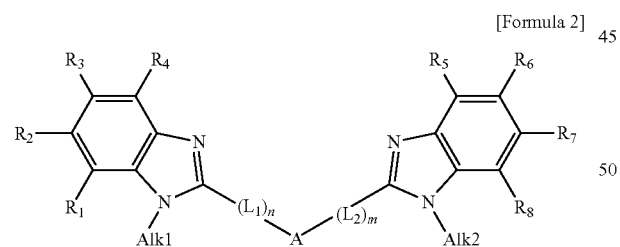

in Formula 2, $R_1$ to $R_8$ are the same as or different from each other, and are each independently hydrogen; deuterium; a halogen group; a nitrile group; a nitro group; a hydroxy group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted alkylamine group; a substituted or unsubstituted aralkylamine group; a substituted or unsubstituted arylamine group; a substituted or unsubstituted heteroarylamine group; a substituted or unsubstituted aryl group; a substituted or unsubstituted fluorenyl group; a substituted or unsubstituted carbazole group; or a substituted or unsubstituted heterocyclic group comprising one or more of N, O, and S atoms, or two or more adjacent groups of $R_1$ to $R_8$ form a monocyclic or polycyclic ring, Ar1 and Ar2 are the same as or different from each other, and are each independently a substituted or unsubstituted aryl group; or a substituted or unsubstituted heterocyclic group;

$L_3$ and $L_4$ are the same as or different from each other, and are each independently oxygen; sulfur; substituted or unsubstituted nitrogen; substituted or unsubstituted phosphorus; a substituted or unsubstituted arylene group; a substituted or unsubstituted fluorenylene group; a substituted or unsubstituted carbazolylene group; or a substituted or unsubstituted heteroarylene group comprising one or more of N, O, and S atoms, n is an integer from 1 to 3, m is an integer from 1 to 3, and when n and m are each present as two or more, the substituents in the parenthesis are each independently the same as or different from each other, A is selected from the following structures,

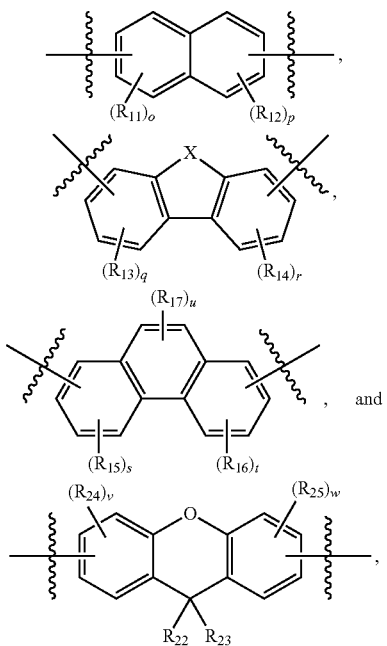

o, p, q, r, s, t, v, and w are each an integer from 0 to 3, and u is an integer from 0 to 2, X is —O—, —S—, or —C($R_{20}$)($R_{21}$)—, $R_{11}$ to $R_{17}$, $R_{20}$, $R_{21}$, $R_{24}$, and $R_{25}$ are the same as or different from each other, and are each independently hydrogen; deuterium; a halogen group; a nitrile group; a nitro group; a hydroxy group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted alkylamine group; a substituted or unsubstituted aralkylamine group; a substituted or unsubstituted arylamine group; a substituted or unsubstituted heteroarylamine group; a substituted or unsubstituted aryl group; a substituted or unsubstituted fluorenyl group; a substituted or unsubstituted carbazole group; or a substituted or unsubstituted heterocyclic group comprising one or more of N, O, and S atoms, and $R_{22}$ and $R_{23}$ are the same as or different from each other, and are each independently hydrogen; or a substituted or unsubstituted alkyl group.

6. The nitrogen-containing heterocyclic compound of claim 5, wherein A is represented by a group selected from the following Formulas:

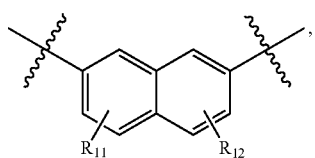

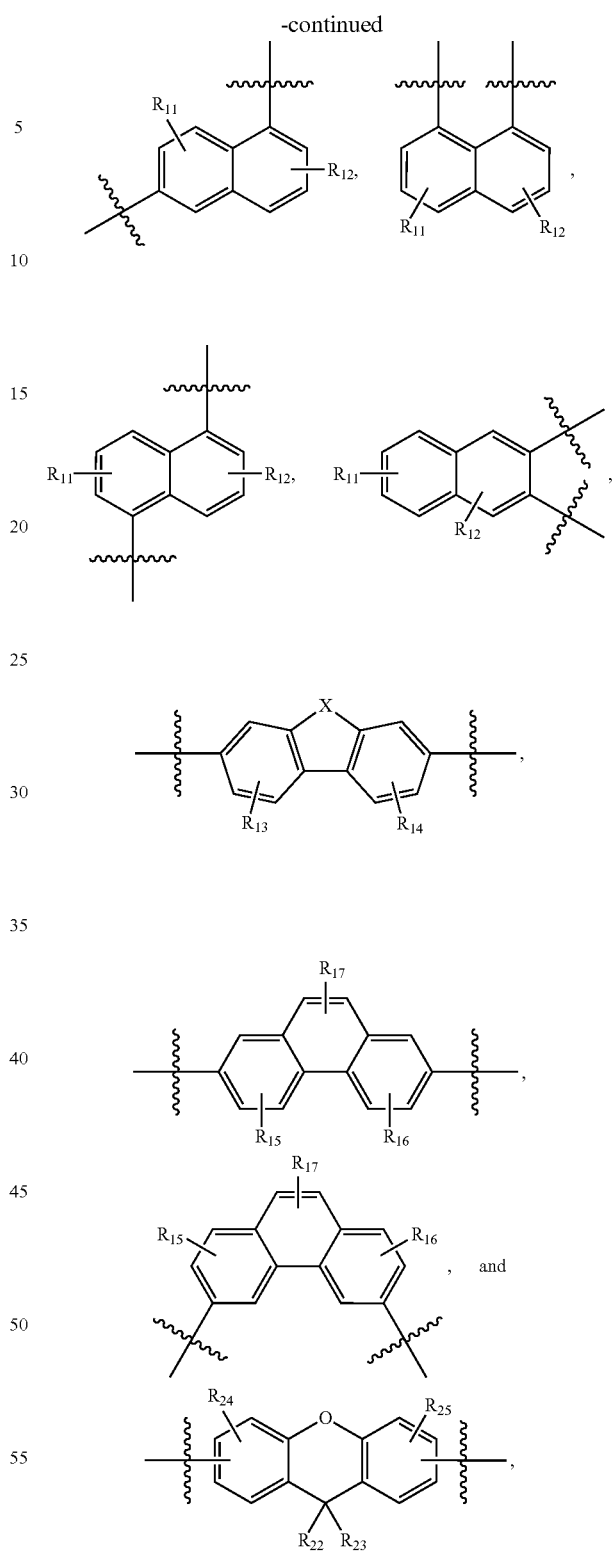

in the formulas, $R_{11}$ to $R_{17}$ and $R_{22}$ to $R_{25}$ are the same as those defined in claim 5.

7. The nitrogen-containing heterocyclic compound of claim 5, wherein Formula 2 comprises a compound represented by any one of the following Formulas 2-1 to 2-5:

[Formula 2-1]
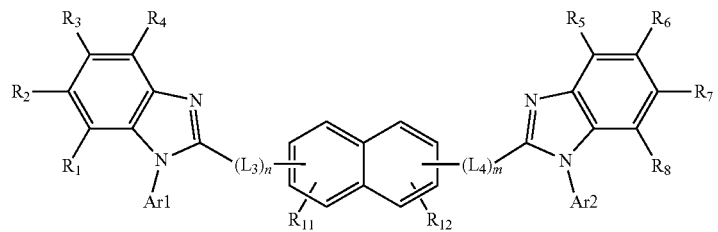
[Formula 2-2]
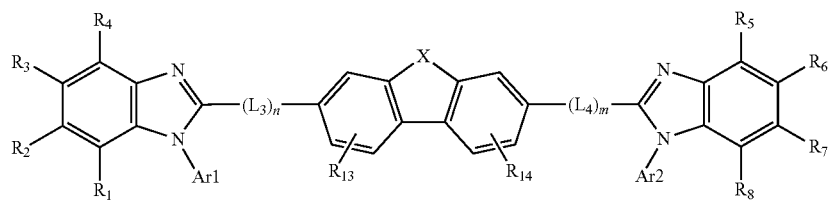
[Formula 2-3]
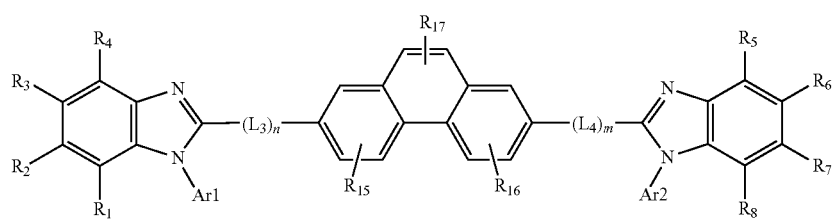
[Formula 2-4]
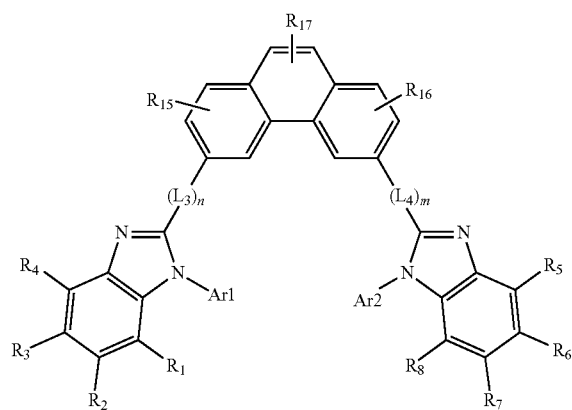
[Formula 2-5]
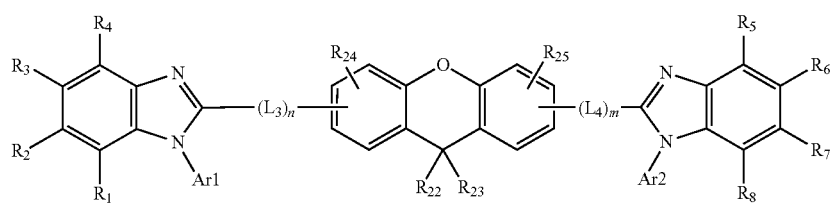

in Formulas 2-1 to 2-5,
$R_1$ to $R_8$, $R_{11}$ to $R_{17}$, $R_{22}$ to $R_{25}$, $L_3$, $L_4$, Ar1, Ar2, n, m, and X are the same as those defined in claim 5.
8. The nitrogen-containing heterocyclic compound of claim 5, wherein the nitrogen-containing heterocyclic compound represented by Formula 2 is selected from the following compounds:
[Formula 3-14]
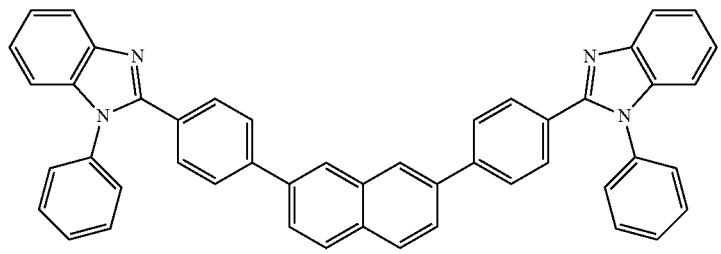
[Formula 3-15]
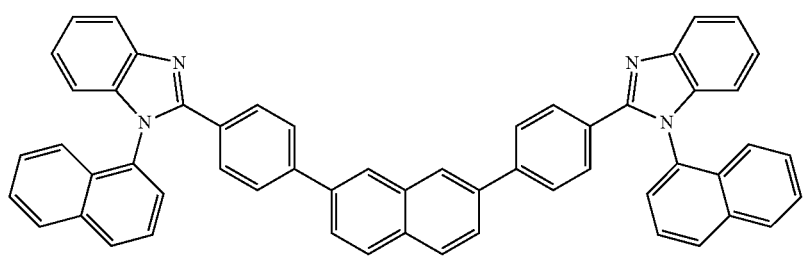
[Formula 4-9]
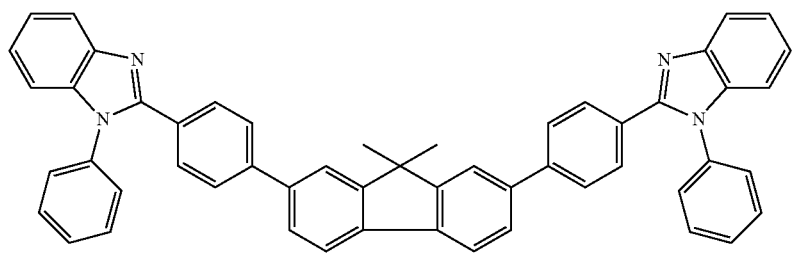
[Formula 5-3]
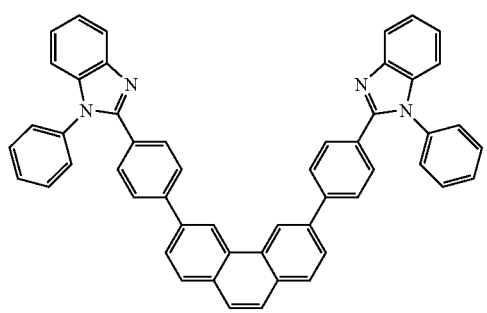
[Formula 6-2]
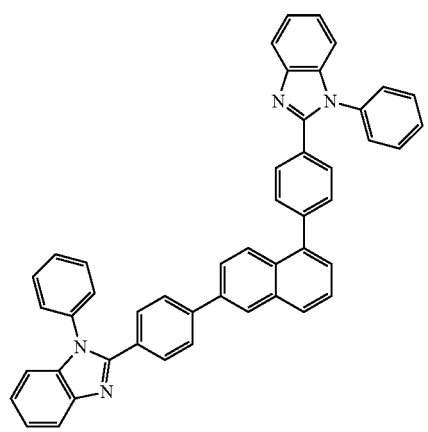

[Formula 6-13]
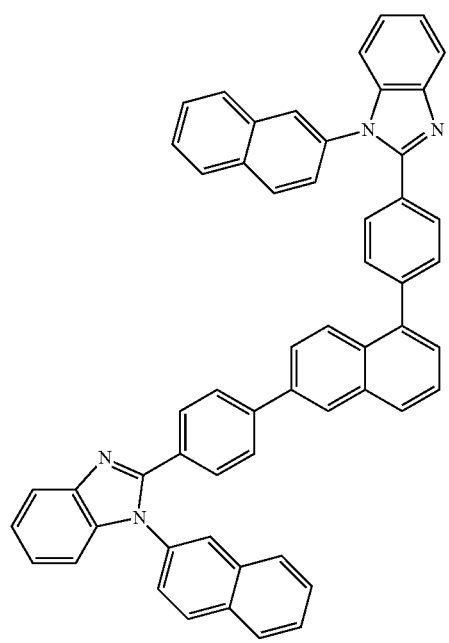
[Formula 7-2]
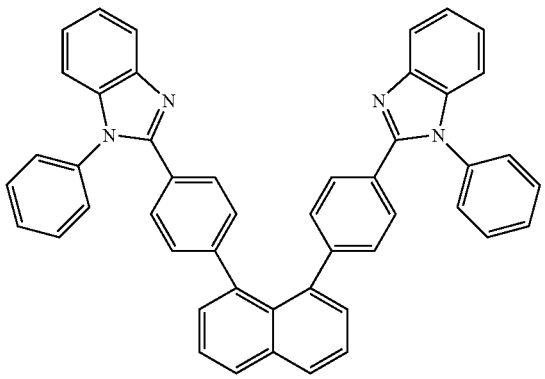
[Formula 7-13]
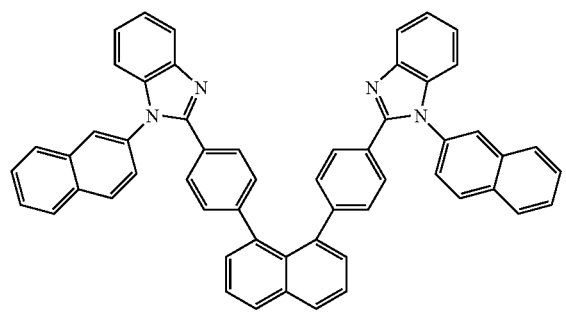
[Formula 8-2]
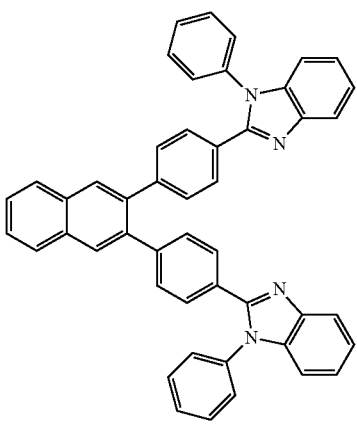

125

-continued

[Formula 8-5]

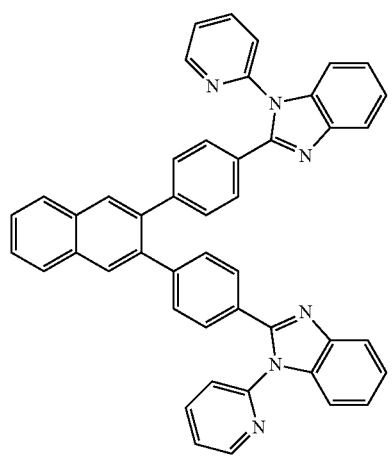

[Formula 9-2]

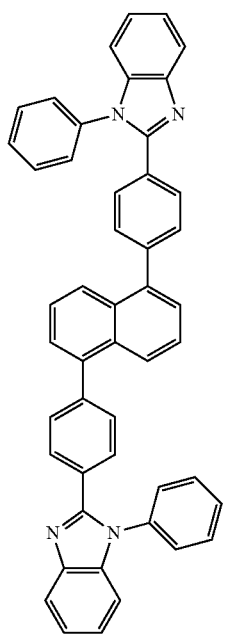

[Formula 9-6]

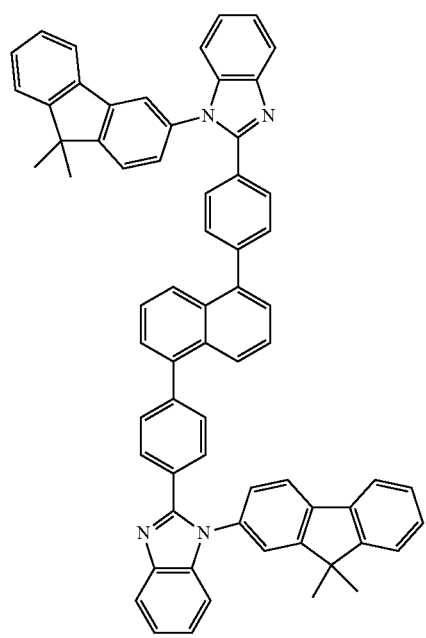

126

[Formula 10-2]

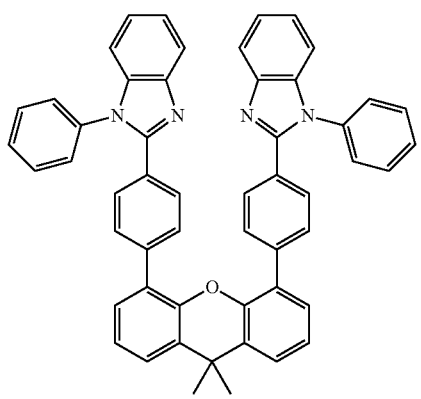

[Formula 10-5]

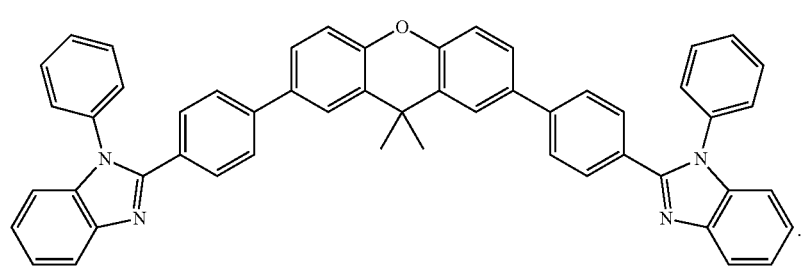

9. An organic electronic device comprising: a first electrode; a second electrode; and organic material layer having one or more layers disposed between the first electrode and the second electrode, wherein one or more layers of the organic material layer comprise the nitrogen-containing heterocyclic compound of claim 1.

10. The organic electronic device of claim 9, wherein the organic material layer comprises a hole injection layer, or a hole transporting layer, and the hole injection layer or the hole transporting layer comprises the nitrogen-containing heterocyclic compound.

11. The organic electronic device of claim 9, wherein the organic material layer comprises a light emitting layer, and the light emitting layer comprises the nitrogen-containing heterocyclic compound as a host of the light emitting layer.

12. The organic electronic device of claim 9, wherein the organic material layer comprises an electron transporting layer, and the electron transporting layer comprises the nitrogen-containing heterocyclic compound.

13. The organic electronic device of claim 9, wherein the organic material layer comprises a hole injection layer or a hole transporting layer comprising a compound that comprises an aryl amino group, a carbazole group, or a benzocarbazolyl group, in addition to an organic material layer comprising the nitrogen-containing heterocyclic compound.

14. The organic electronic device of claim 9, wherein the organic material layer comprising the nitrogen-containing heterocyclic compound comprises the nitrogen-containing heterocyclic compound as a host, and comprises another organic compound, a metal, or a metal compound as a dopant.

15. The organic electronic device of claim 12, wherein the electron transporting layer further comprises a metal or a metal complex.

16. The organic electronic device of claim 9, wherein the organic material layer comprises a charge generating layer, and the charge generating layer comprises the nitrogen-containing heterocyclic compound.

17. The organic electronic device of claim 16, wherein the charge generating layer further comprises a metal or a metal complex.

18. The organic electronic device of claim 9, wherein the organic electronic device is selected from the group consisting of an organic light emitting device, an organic solar cell, an organic photoconductor (OPC) drum, and an organic transistor.

19. An organic electronic device comprising: a first electrode; a second electrode; and organic material layer having one or more layers disposed between the first electrode and the second electrode, wherein one or more layers of the organic material layer comprise the nitrogen-containing heterocyclic compound of claim 5.

20. The organic electronic device of claim 19, wherein the organic material layer comprises an electron transporting layer, and the electron transporting layer comprises the nitrogen-containing heterocyclic compound.

* * * * *